United States Patent [19]
Caldwell et al.

[11] Patent Number: 6,083,602
[45] Date of Patent: Jul. 4, 2000

[54] INCONTINENT GARMENTS

[75] Inventors: J. Michael Caldwell, Cardiff; Peter Ellman, Olivenhain, both of Calif.

[73] Assignee: Nextec Applications, Inc., Vista, Calif.

[21] Appl. No.: 08/487,683

[22] Filed: Jun. 7, 1995

Related U.S. Application Data

[63] Continuation-in-part of application No. 08/472,568, Jun. 7, 1995, Pat. No. 5,874,164, which is a continuation-in-part of application No. 08/442,983, May 17, 1995, Pat. No. 5,869,172, which is a continuation-in-part of application No. 08/407,191, Mar. 17, 1995, Pat. No. 5,876,792, which is a continuation-in-part of application No. 08/017,855, Feb. 16, 1993, Pat. No. 5,418,051, which is a continuation of application No. 07/680,645, Apr. 2, 1991, Pat. No. 5,209,965, which is a continuation of application No. 07/319,778, Mar. 10, 1989, Pat. No. 5,004,643, which is a continuation-in-part of application No. 07/167,630, Mar. 14, 1988, abandoned, application No. 07/167,643, Mar. 14, 1988, abandoned, application No. 07/167,797, Mar. 14, 1988, abandoned, and application No. 07/167,869, Mar. 14, 1988, abandoned.

[51] Int. Cl.$^7$ ..................................................... B32B 3/14
[52] U.S. Cl. .............................. 428/77; 428/78; 428/138; 604/378; 604/381; 604/385.1
[58] Field of Search ................................ 2/83, 114, 901; 128/849, 888; 424/402, 404, 78, 138; 428/260, 272, 274, 290, 306.6, 308.4, 311.1, 311.5, 311.7, 315.5, 907, 77; 523/103, 122; 602/48, 50; 604/367, 372, 378, 381, 385.1

[56] References Cited

U.S. PATENT DOCUMENTS

| | | |
|---|---|---|
| 162,332 | 4/1875 | Allen . |
| 1,281,728 | 10/1918 | Weinheim . |
| 2,117,432 | 5/1938 | Linscott . |
| 2,575,577 | 11/1951 | Beauchamp . |
| 2,626,941 | 1/1953 | Ilabeck . |
| 2,673,823 | 3/1954 | Biefeld . |
| 2,759,900 | 8/1956 | Caldwell et al. . |
| 2,773,050 | 12/1956 | Caldwell et al. . |
| 2,839,479 | 6/1958 | Caldwell et al. . |
| 2,893,962 | 7/1959 | Bartell . |
| 2,956,884 | 10/1960 | Caldwell et al. . |
| 2,976,182 | 3/1961 | Caldwell et al. . |
| 3,026,293 | 3/1962 | Caldwell et al. . |
| 3,165,423 | 1/1965 | Caldwell et al. . |
| 3,184,421 | 5/1965 | Caldwell et al. . |
| 3,265,529 | 8/1966 | Caldwell et al. . |
| 3,326,713 | 6/1967 | Smith et al. . |
| 3,328,661 | 6/1967 | Grebe . |
| 3,356,628 | 12/1967 | Smith et al. . |
| 3,360,394 | 12/1967 | Griffin et al. . |
| 3,393,186 | 7/1968 | Groves . |
| 3,398,182 | 8/1968 | Guenthner et al. . |
| 3,436,366 | 4/1969 | Modic . |
| 3,594,213 | 7/1971 | Rudman . |
| 3,639,155 | 2/1972 | Hartieim et al. . |
| 3,896,251 | 7/1975 | Landucci . |
| 4,013,615 | 3/1977 | Ohashi et al. . |
| 4,032,502 | 6/1977 | Lee et al. . |
| 4,108,825 | 8/1978 | Hayes . |
| 4,110,392 | 8/1978 | Yamazaki . |
| 4,112,179 | 9/1978 | Maccalous et al. . |
| 4,162,243 | 7/1979 | Lee et al. . |
| 4,162,356 | 7/1979 | Grenoble . |
| 4,216,252 | 8/1980 | Moeller . |
| 4,216,290 | 8/1980 | De Beul et al. . |
| 4,250,075 | 2/1981 | Monroe et al. . |
| 4,287,261 | 9/1981 | West et al. . |
| 4,293,611 | 10/1981 | Martin . |
| 4,297,265 | 10/1981 | Olsen . |
| 4,311,760 | 1/1982 | Kalinowski et al. . |
| 4,329,274 | 5/1982 | Faltynek . |
| 4,369,231 | 1/1983 | West et al. . |
| 4,370,365 | 1/1983 | Takamizawa et al. . |
| 4,426,476 | 1/1984 | Chang . |
| 4,427,801 | 1/1984 | Sweet . |
| 4,442,060 | 4/1984 | Bouverot et al. . |
| 4,454,191 | 6/1984 | von Blücher et al. . |
| 4,472,470 | 9/1984 | Modic . |
| 4,478,895 | 10/1984 | Makami et al. . |
| 4,500,584 | 2/1985 | Modic . |
| 4,500,659 | 2/1985 | Kroupa et al. . |
| 4,504,549 | 3/1985 | Pines et al. . |
| 4,539,930 | 9/1985 | Stuck et al. . |

(List continued on next page.)

FOREIGN PATENT DOCUMENTS

| | | |
|---|---|---|
| 57-149559 | 9/1982 | Japan . |
| 422469 | 9/1974 | Russian Federation . |
| 89/08553 | 9/1989 | WIPO . |
| 89/08554 | 9/1989 | WIPO . |
| 89/08555 | 9/1989 | WIPO . |

OTHER PUBLICATIONS

Owen, M.J., "The Surface Activity of Silicones: A Short Review", *Ind. Eng. Chem. Prod. Res. Dev.* vol. 19, p. 97 (1980).

"Silicones", *Encyl. of Polymer Sci. and Engineering*, 2nd ed., Wiley, New York, v. 15 (1985–1990).

Floyd, D.T., "Organo–Modified Silicone Copolymers for Cosmetic Use", *Cosmetic and Pharmaceutical Applications of Polymers*, p. 49–72, Plenum Press (New York) (1991).

Caldwell et al., "Vapor–Permeable, Water–Resistant Fabrics," *American Dyestuff Reporter*, No. 3, pp. 25–29 (Jan. 30, 1967).

"Uvinul: UV Inhibitors for Cosmetics, Plastics, Coatings and Textiles," BASF Corp., Rensselaer, N.Y. (No Date).

"ProNectin™F" brochure, Protein Polymer Technologies, Inc. (1991).

*Primary Examiner*—Christopher Raimund
*Attorney, Agent, or Firm*—Karl Stauss; Jones & Askew, LLP

[57] ABSTRACT

The present invention includes novel barrier webs that have certain desirable physical qualities such as water resistance, increased durability, improved barrier qualities and the like. The present invention further comprises a barrier web comprising a web that has been treated with a curable shear thinned thixotropic polymer composition, the fabric being adapted to be substantially impermeable to liquids, permeable to gases and impermeable to microorganisms. The barrier webs of the present invention are either impermeable to all microorganisms or are impermeable to microorganisms of certain sizes. The present invention also includes fabrics that are capable of either selective binding certain microorganisms, particles or molecules depending upon what binding partners are incorporated into the polymer before application to the fabric.

5 Claims, 10 Drawing Sheets

U.S. PATENT DOCUMENTS

| | | |
|---|---|---|
| 4,548,859 | 10/1985 | Kline et al. . |
| 4,555,811 | 12/1985 | Shimalla . |
| 4,560,611 | 12/1985 | Naka et al. . |
| 4,562,219 | 12/1985 | Frye . |
| 4,585,830 | 4/1986 | Sweet . |
| 4,588,614 | 5/1986 | Lauchenauer . |
| 4,600,436 | 7/1986 | Travor et al. . |
| 4,619,864 | 10/1986 | Hendrix et al. . |
| 4,666,765 | 5/1987 | Caldwell et al. . |
| 4,684,570 | 8/1987 | Malaney . |
| 4,753,978 | 6/1988 | Jensen . |
| 4,758,239 | 7/1988 | Yeo et al. . |
| 4,785,047 | 11/1988 | Jensen . |
| 4,828,556 | 5/1989 | Braun et al. . |
| 4,894,105 | 1/1990 | Dyksterhouse et al. . |
| 4,919,739 | 4/1990 | Dyksterhouse et al. . |
| 5,019,062 | 5/1991 | Ryan et al. . |
| 5,128,198 | 7/1992 | Dyksterhouse et al. . |
| 5,322,727 | 6/1994 | Yankus et al. . |

INCONTINENT GARMENTS

CROSS-REFERENCE TO RELATED PATENT APPLICATIONS

This application is a continuation-in-part of U.S. patent application Ser. No. 08/472,568 filed on Jun. 7, 1995, now U.S. Pat. No. 5,874,164, which is a continuation-in-part of U.S. patent application Ser. No. 08/442,983 filed on May 17, 1995, now U.S. Pat. No. 5,869,172, which is incorporated herein by reference, which is a continuation-in-part of U.S. patent application Ser. No. 08/407,191 filed on Mar. 17, 1995, now U.S. Pat. No. 5,876,792, which is a continuation-in-part of U.S. patent application Ser. No. 08/017,855 filed Feb. 16, 1993, which issued as U.S. Pat. No. 5,418,051, which is a continuation of U.S. patent application No. 07/680,645 filed on Apr. 2, 1991, which issued as U.S. Pat. No. 5,209,965, which is a continuation of U.S. patent application Ser. No. 07/319,778 filed Mar. 10, 1989, which issued as U.S. Pat. No. 5,004,643, which is a continuation-in-part of Ser. No. 07/167,630 filed on Mar. 14, 1988, abandoned, and a continuation-in-part of U.S. patent application Ser. No. 07/167,643 filed on Mar. 14, 1988, abandoned and a continuation-in-part of U.S. patent application Ser. No. 07/167,797 filed on Mar. 14, 1988, abandoned, and a continuation-in-part of U.S. patent application Ser. No. 07/167,869 filed on Mar. 14, 1988, abandoned, and all of which are incorporated herein by reference.

FIELD OF THE INVENTION

The present invention relates to barrier fabrics. More particularly, the present invention relates to barrier fabrics that are substantially impermeable to water, substantially permeable to gases and impermeable or selectively impermeable or permeable to particles such as microorganisms, cells, molecules, and the like. The present invention also includes articles and clothing made from the barrier fabrics described herein including career hospital garments, incontinent briefs and the like.

BACKGROUND OF THE INVENTION

Barrier fabrics are generally characterized by being impervious to penetration by liquids. There is a class of barrier fabrics which, additionally, are vapor permeable to provide what is termed breathability. Barrier fabrics are especially useful in the medical career apparel garments. The barrier fabrics in the prior art can be generally classified as disposable and reuseable. Disposable fabrics are typically constructed from nonwovens made from light weight synthetic fibers or synthetic fibers blended with natural fibers. Performance of disposable nonwoven fabrics in terms of liquid repellency and flame retardancy are quite acceptable. Reusable fabrics are normally woven and may be constructed from cotton or cotton/polyester blends of a high thread count to provide a physical barrier to prevent or reduce the spread of infectious materials and vectors.

While reusable woven fabrics generally offer more comfort in terms of drapeability, breathability, transmission of heat and water vapor, stiffness, etc., and improved (reduced) cost per use, they lack the liquid repellency the market has come to expect on the basis of experience with the disposables, especially after repeated launderings and/or steam (autoclave) sterilizations.

Woven reusable surgical barrier fabrics must meet or exceed the current criteria for National Fire Protection Association (NFPA-99) and the Association of Operating Room Nurses (AORN) "Recommended Practices-Aseptic Barrier Material for Surgical Gowns and Drapes" used in constructing operating room wearing apparel, draping and gowning materials. To be effective, the fabric must be resistant to blood and aqueous fluid (resist liquid penetration); abrasion resistant to withstand continued reprocessing; lint free to reduce the number of particles and to reduce the dissemination of particles into the wound; drapeable; sufficiently porous to eliminate heat buildup; and flame resistant.

Reusable fabrics should withstand multiple laundering and, where necessary, sterilization (autoclaving) cycles; be non-abrasive and free of toxic ingredients and non-fast dyes; be resistant to tears and punctures; provide an effective barrier to microbes, preferably be bacteriostatic in their own right; and the reusable material should maintain its integrity over its expected useful life.

None of the fabrics or the fabrics taught in the prior art has the physical characteristics of (1) being substantially resistant or impermeable to liquids, such as water, (2) being permeable to gases, and (3) impermeable to microorganisms. In addition, none of the fabrics taught in the prior art teach or suggest fabrics that are capable of selectively removing or retaining microorganisms or other particles or molecules from the surrounding milieu.

In the prior art, it has been proposed to treat porous webs, especially fabrics, with silicone resins and also with fluorochemicals. Conventional treatments of webs fall into the general categories of (i) surface coatings and (ii) saturations or impregnations.

For example, U.S. Pat. Nos. 3,436,366; 3,639,155; 4,472,470; 4,500,584; and 4,666,765 disclose silicone coated fabrics. Silicone coatings are known to exhibit relative inertness to extreme temperatures of both heat and cold and to be relatively resistant to ozone and ultraviolet light. Also, a silicone coating can selectively exhibit strength enhancement, flame retardancy and/or resistance to soiling. Fluorochemical treatment of webs is known to impart properties, such as soil resistance, grease resistance, and the like.

Prior art fluorochemical and silicone fabric treatment evidently can protect only that side of the fabric upon which they are disposed. Such treatments significantly alter the hand, or tactile feel, of the treated side. Prior silicone fabric coatings typically degrade the tactile finish, or hand, of the fabric and give the coated fabric side a rubberized finish which is not appealing for many fabric uses, particularly garments.

U.S. Pat. No. 4,454,191 describes a waterproof and moisture-conducting fabric coated with a hydrophilic polymer. The polymer is a compressed foam of an acrylic resin modified with polyvinyl chloride or polyurethane and serves as a sort of "sponge", soaking up excess moisture vapor. Other microporous polymeric coatings have been used in prior art attempts to make a garment breathable, yet waterproof.

Various polyorganosiloxane compositions are taught in the prior art that can be used for making coatings that impart water-repellency to fabrics. Typical of such teachings is the process described in U.S. Pat. No. 4,370,365 which describes a water repellent agent comprising, in addition to an organohydrogenpolysiloxane, either one or a combination of linear organopolysiloxanes containing alkene groups, and a resinous organopolysiloxane containing tetrafunctional and monofunctional siloxane units. The resultant mixture is catalyzed for curing and dispersed into an aqueous emulsion. The fabric is dipped in the emulsion and heated. The resultant product is said to have a good "hand" and to possess waterproofness.

This type of treatment for rendering fabrics water repellent without affecting their "feel" is common and well known in the art. However, it has not been shown that polyorganosiloxanes have been coated on fabrics in such a way that both high levels of resistance to water by the fibers/filaments and high levels of permeability to water vapor are achieved. As used herein, the term "high levels of permeability to water vapor" has reference to a value of at least about 500 gms/m$^2$/day, as measured by ASTM E96-80B. Also, as used herein, the term "high level of waterproofness" is defined by selective testing methodologies discussed later in this specification. These methodologies particularly deal with water resistance of fabrics and their component fibers.

Porous webs have been further shown to be surface coated in, for example, U.S. Pat. Nos. 4,478,895; 4,112,179; 4,297,265; 2,893,962; 4,504,549; 3,360,394; 4,293,611; 4,472,470; and 4,666,765. These surface coatings impart various characteristics to the surface of a web, but do not substantially impregnate the web fibers. Such coatings remain on the surface and do not provide a film over the individual internal fibers and/or yarn bundles of the web. In addition, such coatings on the web surface tend to wash away quickly.

Prior art treatments of webs by saturation or impregnation also suffer from limitations. Saturation, such as accomplished by padbath immersion, or the like, is capable of producing variable concentrations of a given saturant chemical.

To treat a flexible web, by heavy saturation or impregnation with a polymer material, such as a silicone resin, the prior art has suggested immersion of the flexible web, or fabric, in a padbath, or the like, using a low viscosity liquid silicone resin so that the low viscosity liquid can flow readily into, and be adsorbed or absorbed therewithin. The silicone resin treated product is typically a rubberized web, or fabric, that is very heavily impregnated with silicone. Such a treated web is substantially devoid of its original tactile and visual properties, and instead has the characteristic rubbery properties of a cured silicone polymer.

U.S. Pat. No. 2,673,823 teaches impregnating a polymer into the interstices of a fabric and thus fully filling the interstices. This patent provides no control of the saturation of the fabric. It teaches full saturation of the interstices of the fabric.

The prior art application of liquid or paste compositions to textiles for purposes of saturation and/or impregnation is typically accomplished by an immersion process. Particularly for flexible webs, including fabric, an immersion application of a liquid or paste composition to the web is achieved, for example, by the so-called padding process wherein a fabric material is passed first through a bath and subsequently through squeeze rollers in the process sometimes called single-dip, single-nip padding. Alternatively, for example, the fabric can be passed between squeeze rollers, the bottom one of which carries the liquid or paste composition in a process sometimes called double-dip or double-nip padding.

Prior art treatment of webs that force a composition into the spaces of the web while maintaining some breathability have relied on using low viscosity compositions or solvents to aid in the flow of the composition. U.S. Pat. No. 3,594,213 describes a process for impregnating or coating fabrics with liquified compositions to create a breathable fabric. This patent imparts no energy into the composition to liquify it while forcing it into the spaces of the web. The composition is substantially liquified before placement onto and into the web. U.S. Pat. No. 4,588,614 teaches a method for incorporating an active agent into a porous substrate. This patent utilizes a solvent to aid in the incorporation of the active agent into the web.

Prior art apparatus for the coating of webs, including fabrics, generally deposits a coating onto the fabric at a desired thickness. Coating at a predetermined thickness can be achieved by deposition of coating material or by the scraping of a coating upon the fabric by knives. Flexible webs are generally urged between oppositely disposed surfaces, one of which would be a doctoring blade or drag knife. The blade or knife smooth the coating and maintain the thickness of the coating to a desired thickness. For example, it is possible to apply a relatively thick silicone liquid elastomer coating to a rough web, typically of fiberglass, in order to make architectural fabric as is taught in U.S. Pat. No. 4,666,765. In this example, the drag knives are set to a thickness of about 2 to 10 mils thicker than the web thickness. This setting, depending on the coating speed, can yield a base coat thickness of approximately 3 to 12 mils thicker than the web thickness.

Various types of coatings, and various coating thicknesses, are possible. However, a general principle of coating machinery is that the coating material is swept, or dragged, along the surface of the fabric. No special attention is normally given to any pressured forcing of the coating into the fabric, therein making the coating also serve as an impregnant. Of course, some coating will be urged into surface regions of the fabric by the coating process. Generally, however, application of high transversely exerted (against a fiber or web surface) forces at the location of the coating deposition and/or smoothing is not desired in the prior art processes because it is the goal of the prior art coating processes to leave a definite thickness of coating material upon a surface of the fabric, and not to scrape the fabric clean of surface-located coating material.

One prior art silicone resin composition is taught by U.S. Pat. Nos. 4,472,470 and 4,500,584, and includes a vinyl terminated polysiloxane, typically one having a viscosity of up to about 2,000,000 centipoises at 25° C., and a resinous organosiloxane polymer. The composition further includes a platinum catalyst, and an organohydrogenpolysiloxane crosslinking agent, and is typically liquid. Such composition is curable at temperatures ranging from room temperature to 100° C. or higher depending upon such variables as the amount of platinum catalyst present in the composition, and the time and the temperature allowed for curing.

Such compositions may additionally include fillers, including finely divided inorganic fillers. Silicone resin compositions that are free of any fillers are generally transparent or translucent, whereas silicone resin compositions containing fillers are translucent or opaque depending upon the particular filler employed. Cured silicone resin compositions are variously more resinous, or hard, dependent upon such variables as the ratio of resinous copolymer to vinyl terminated polysiloxane, the viscosity of the polysiloxane, and the like.

Curing (including polymerization and controlled crosslinking) can encompass the same reactions. However, in the fabric finishing arts, such terms can be used to identify different phenomena. Thus, controllable and controlled curing, which is taught by the prior art, may not be the same as control of crosslinking. In the fabric finishing arts, curing is a process by which resins or plastics are set in or on textile materials, usually by heating. Controlled crosslinking may be considered to be a separate chemical reaction from curing in the fabric finishing arts. Controlled crosslinking can occur between substances that are already cured. Controlled crosslinking can stabilize fibers, such as cellulosic fibers through chemical reaction with certain compounds applied thereto. Controlled crosslinking can improve mechanical factors such as wrinkle performance and can significantly improve and control the hand and drape of the web. Polymerization can refer to polymer formation or polymer growth.

What is needed in the industry is a barrier fabric that is impermeable to liquids, is permeable to gases, and is impermeable to microorganisms. In addition, what is needed are methods and processes for producing fabrics with predetermined pore sizes that allow the manufacturer to produce a fabric with a desired pore size.

SUMMARY OF THE INVENTION

The present invention includes novel barrier webs that have certain desirable physical qualities such as water resistance, increased durability, improved barrier qualities and the like. The present invention further comprises a barrier web comprising a web that has been treated with a curable shear thinned thixotropic polymer composition, the fabric being adapted to be substantially impermeable to liquids, permeable to gases and impermeable to microorganisms. The barrier webs of the present invention are either impermeable to all microorganisms or are impermeable to microorganisms of certain sizes. The present invention also includes fabrics that are capable of selectively binding certain microorganisms, particles or molecules depending upon what binding partners are incorporated into the polymer before application to the fabric.

The present invention also includes methods and machinery for manufacturing the novel barrier webs. The novel barrier webs of the present invention can be used to prepare a wide variety of products including, but not limited to, carpets, specilized clothing, career apparel, bioengineered surfaces for diagnostic applications, and upholstery. By practicing the present invention, fabrics, and fibers can be manufactured with a wide variety of desired physical characteristics.

The novel fabrics of the present invention are generally flat or planar. The barrier webs can comprise fibers in the form of monofilaments, yarns, staples, or the like. The barrier webs may be a fabric which is woven or nonwoven with fibers that can be of any desired composition. The barrier webs will generally be tensionable, but not too weak or elastomeric to be processed in accordance with the teachings of the present invention.

The present invention also includes barrier webs that have bioactive surfaces. These webs can be used in a variety of ways including, but not limited to, measurement of analytes in solution, selective filtration of fluids, and the isolation of particles, such as cells, from a suspension of particles. The present invention also contemplates assay kits containing the bioactive surfaces.

The fibers utilized in a porous flexible fabric employed in the practice of the present invention can be of natural or synthetic origin. Mixtures of natural fibers and synthetic fibers can also be used. Examples of natural fibers include cotton, wool, silk, jute, linen, and the like. Examples of synthetic fibers include rayon, acetate, polyesters (including polyethyleneterephthalate), polyamides (including nylon), acrylics, olefins, aramids, azlons, glasses, modacrylics, novoloids, nytrils, rayons, sarans, spandex, vinal, vinyon, and the like.

The breathable barrier webs of the present invention can be used to manufacture foul weather garments, surgical gowns, surgical scrub suits, sterilization wrappers (CSR wrap), cover gowns, isolation gowns, hamper bags, jump suit, work aprons, laboratory coats and the like. The fabric is especially suited as a barrier to prevent or control the spread of infectious microorganisms. The invention also includes processes for making a woven medical fabric.

Accordingly, it is an object of the present invention to provide barrier webs that are particularly suitable as a barrier web that is substantially impermeable to liquids, especially aqueous liquids and is permeable to gases.

Another object of the present invention is to provide a barrier web that is impermeable to microorganisms including viruses, bacteria, fungi and protozoa.

Yet another object of the present invention is to provide a barrier web that has the additional quality of inhibiting or killing microorganisms.

Another object of the present invention is to provide a barrier web that is suitable for use as a bandage or surgical gauze.

Another object of the present invention is to provide a barrier web that can be used in products for the control of incontinence such as diapers, incontinent briefs, training pants and the like.

Another object of the present invention is to provide a reusable barrier web that can be sterilized by means other than gamma irradiation, steam autoclave or ethylene oxide.

Another object of the present invention is to provide a barrier web support with a bioactive surface that can be used to measure analytes in solutions.

Another object of the present invention is to provide a surgical gown with an optional web thereon that is an effective barrier against blood or other body fluids.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

DESCRIPTION OF THE PREFERRED EMBODIMENTS

Figure 1:
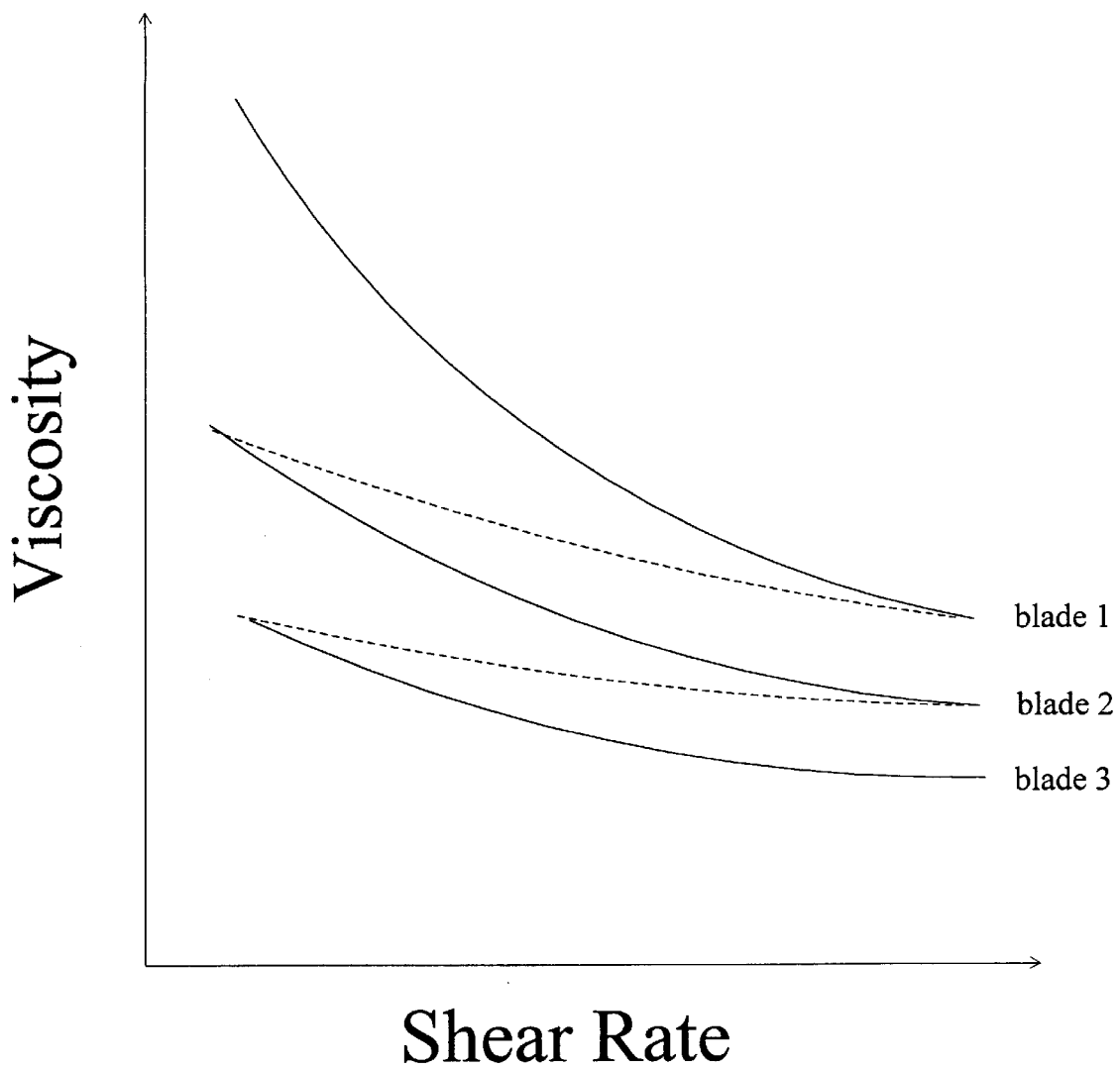
FIG. 1 is a graph plotting the rheological behavior of polymers used in the practice of this invention.

The following description includes the best presently contemplated mode of carrying out the invention. This description is made for the purpose of illustrating the general principles of the inventions and should not be taken in a limiting sense.

The present invention includes novel webs that have certain desirable physical qualities such as water resistance, increased durability, improved barrier qualities and the like. In one embodiment, the fabrics of the present invention are impermeable to microorganisms while, at the same time, are permeable to gases, including water vapor, and impermable to liquids such as water, body fluids and the like. The present invention also includes methods and machinery for manufacturing the novel barrier webs. The novel webs, fibers and fabrics of the present invention can be used to prepare a wide variety of products including, but not limited to, carpets, specilized clothing, career apparel, bioengineered surfaces for diagnostic applications, and upholstery.

The present invention relates to methods and apparatus for manufacturing a treated web and are more fully described in U.S. Pat. No. 5,876,792 incorporated in its entirety by reference. The subject methods and apparatus involve the control of numerous variables, including, without limitation, web tension (both overall web tension as well as the web tension immediately before and after each individual blade), angle of entry of web into each blade, blade angle in relation to horizonal reference point, blade pressure against moving web, angle of exit of web from each blade, web speed, number of blades, the pressure of the leading nip rolls, the pressure of the trailing nip rolls, static control, thickness of each blade, bevel on each blade, oven cure temperature, oven cure dwell time, blade temperature and blade surfaces and edge conditions and blade finish.

Other variables that affect the finished product, but are not directly related to the methods and apparatus, include, without limitation, the polymer blend, the starting viscosity of the polymer composition, accelerators added to the polymer composition, additives added to the polymer composition, the type of web used, ambient temperature, humidity, airborne contaminants, lint on web, pre-treatment of web, sub-web surface temperature, and web moisture content.

With respect to the blades, the temperature of the blade can be kept cool to keep the polymer composition from curing prematurely. This can be accomplished by passing a coolant prathrough or around the blade or by other means well known in the art. Alternatively, the blade could be heated by passing a heated fluid around or through the blade, if desired to improve or alter the viscosity and rheology for the required changes in the polymer necessary to achieve a specific product.

The blade finish is also important. A hard, smooth surface of both blade face and edges is desirable to shear thin the polymer and keep it flowing and to maximize friction or selectively create shear forces between tie web, the polymer, and blade(s). For some applications, the blades should preferably remain rigid in all dimensions and have minimal resonance in order to get uniform web treatment.

The apparatus has facilities for rotating the angle of each blade ±90° from the vertical. To vary the shear and placement forces of the blade against the web, polymer and additives, adjustment facilities are provided for moving the blade vertically up and down and moving the blade forward and backward horizontally. All three axis are important for creating the desired control which causes the encapsulated fibers and/or filaments, the additive placement and orientation on the fiber and filaments, the optional internal layer, and the controlled thickness of the encapsulating films or internal layer. The lateral placement of each blade relative to the other is also important and facilities are provided for allowing lateral movement of each blade toward and away from each other. The lateral placement of each blade controls the micro tension and elastic vibration of the web between the preceding roll and the blade, thereby controlling the web after the immediate exit of the web from the blade and controlling the Coanda Effect, as described in U.S. Pat. No. 4,539,930, so that controlled placement of the internal layer takes place.

Changing the tension of the web results in changes internally in the web, such as the position of the internal layer of the web, as well as how much or how little fiber encapsulation occurs, and the thickness of the film encapsulating the individual fibers or filaments.

At the leading edge of the blade, the web is stretched longitudinally and the polymer is simultaneously and dynamically shear thinned, placed into the web, and partially extracted from the web, thereby leaving encapsulated fibers and filaments and/or an internal layer. As the web passes the leading edge of the blade, the elastic recovery forces of the web combined with the relaxation or elastic recovery of the fibers and filaments causes fiber encapsulation and the surface chemistry modification (or bloom). It is believed that this occurs by the popping apart of the individual fibers and filaments. The fibers and filaments either pull the polymer from the interstitial spaces or the rheology of the polymer attracts it to the fibers and filaments or some combination of the two. The end result is that the polymer in the interstitial spaces moves to the fibers and filaments as they move or snap apart, thereby creating encapsulated fibers and filaments. At the bottom surface of the blade, the thickness, depth, and controlled placement of the internal layer is determined. A wider blade results in a thicker internal layer of polymer. Further, the dynamics of stretch and relaxation of the fibers provides for an even energy necessary for the thin film encapsulation of the polymer composition over the fibers.

Passing the treated web through the exit nip rolls pushes the fibers or structural elements of the web together. The hardness of and the material of the exit nip rolls affects the finished web. The exit nip rolls could be either two rubber rolls or two steel rolls, or one steel roll and one rubber roll, and the rubber rolls could be of different durometers. Further, the variation of the hardness of one or both nip rolls changes the contact area or footprint between the nip rolls and the web as the web passes therebetween. With a softer roll there is a larger contact area and the web is capable of retaining the (a) thin film encapsulation of the individual fibers and filaments, (b) the controlled placement of the internal coating, and (c) controlled placement of the additives in (a) and (b). With a harder roll there is a smaller contact area which is appropriate for heavier webs.

Additional controllable variables include the various controls of each blade, the nip rolls durometer, the nip release effect, the nip surface characteristics, the guidance, and the pre-treatment of the substrate. Some of the controllable variables are: 1) web tension, 2) angle of entry of fabric into the blade, 3) blade angle in reference to horizontal position, 4) blade pressure against fabric (blade height), 5) angle of exit of fabric from blade, 6) web speed, 7) number of blades, 8) initial rheology and viscosity of polymers, 9) nip pressure, 10) entry nip pressure 11) static control, 12) blade thickness and shape, 13) polymers and polymer blends, 14) accelerators and inhibitors added to polymers, 15) additives in polymers, 16) oven cure temperature, 17) oven cure dwell time, 18) substrate type, 19) ambient polymer temperature, 20) humidity, 21) degree web is deformed under lateral tension, and 22) airborne contaminants and lint on the web. Control of the above variables affects: (a) the thin film encapsulation of the individual fibers and filaments, (b) the controlled placement of the internal coating, and (c) the controlled placement of the additives in (a) and (b).

An increase in web tension causes less polymer to be applied to the web, and also, more of what is applied to be extracted from the web. Web tension occurs between the entrance pull stand and the exit pull stand. The primary tension is a result of the differential rate between the driven entrance pull stand and the driven exit pull stand whereby the exit pull stand is driven at a rate faster than the entrance pull stand. Other factors which effect tension are (1) the blade roll diameter, (2) the vertical depth of the blade(s), (3) the durometer of the entrance pull stand roll and rubber roll of the exit pull stand, and (4) the friction as the web passes under the blade(s). The larger the blade roll diameter, the higher the tension of the web. If the drive rate of the web remains constant, then increasing the depth of the blade into the web creates a greater micro tension condition under the blade. Similarly, decreasing the depth into the web decreases the micro tension under the blade. The lower the durometer of the entrance pull stand roll and rubber roll of the exit pull stand, the larger the footprint or contact area between the rolls. A larger footprint produces more surface friction, thereby limiting web slippage and increasing tension. Likewise, web slippage can be effected by changing the surface texture of the rolls, i.e., a smooth roll will allow greater slippage than a highly contrasting or rough surface texture. Increasing friction, as the fabric passes under the blade(s), also produces tension. Friction is a function of the surface area of the bottom of the blade(s). Increasing the surface area increases the friction which increases the tension.

The entry angle of the web into the blade(s) can be varied by blade roll height, blade roll diameter, blade angle, distance between prior blade roll(s) and blade(s), and height of the blades. Increasing the blade roll height and blade roll diameter increases the entry angle into the blade. Rotating the blade angle clockwise from the perpendicular, with the web running left to right, increases the entry angle. Likewise, rotating the blade angle counter-clockwise from the perpendicular, with the web running left to right, decreases the entry angle. Decreasing the distance between the roll before the blade and the blade decreases the angle of entry. Increasing the downward depth of the blade(s) into the web decreases the angle of entry into the blade(s).

The angle of the blade(s) is completely changeable and fully rotational to 360°. The fully rotational axis provides an opportunity for more than one blade per rotational axis. Therefore, a second blade having a different thickness, bevel, shape, resonance, texture, or material can be mounted. Ideally the apparatus contains two or three blades per blade mount.

The blade height or blade pressure applied against a web can be obtained through the vertical positioning of the blade(s) in the blade mount. The greater the downward depth of the blade(s), the greater the pressure. Blade pressure against the web is also accomplished through the tension of the web as described above.

The same line components that affect the entry angle of the web into the blade(s), also affect the exit angle of the web out of the blade. Any changes in blade roll(s) vertical height, diameter, or distance away from the blade, affects the exit angle of the web. If the angle of the blade is rotated clockwise as described above, the entry angle of the web increases, thus decreasing the exit angle.

Web speed is proportional to the variable speed of the motor which drives the entrance and exit nip stands. Web speed can effect the physics of the polymers as the web passes under the blades.

The number of blades can vary. Generally, more than one blade is required. The polymer is first applied onto the web prior to the first blade. At this blade, a rolling bead of polymer can exist at the interface of the blade and the web (entry angle) Basically, a high viscosity polymer is applied and through the process of shear thinning, the viscosity is greatly decreased, allowing the polymer to enter into the interstitial spaces of the web. Any blade(s) after the first blade, serves to further control the polymer rheology and viscosity and continue the controlled placement of the polymer into the web. This is accomplished by controllably removing excess polymer to obtain an even distribution of polymer to any area, or a combination of the three areas of a) the thin film encapsulation of the individual fibers and filaments, b) the controlled placement of the internal layer, and c) the controlled placement of the additives in a) and b).

The initial process dynamics for the rheology and viscosity of the polymer is designed and engineered with the required attributes to achieve (a) the thin film encapsulation of the individual fibers and filaments, (b) the controlled placement of the internal layer, and (c) the controlled placement of the additives in (a) and (b). If the polymer viscosity is high, the polymer may need to be pre-thinned by using a dynamic mixer or three-roll head. The dynamic mixer or the three-roll head can significantly reduce the viscosity and even pre-place the polymer into a thick substrate or web to allow the blades to further shear thin and enhance the flow and placement of the polymer.

The entrance pull stand is a driven roll proportionally driven at a predetermined rate slower than the exit pull stand. The entrance and exit pull stands are adjustable from about 100 pounds of force to 5 or more tons of force.

The bottom rolls of both the entrance and exit pull stands have micro-positioning capability to provide for gap adjustment and alignment. The composition of the top roll of the entrance and exit pull stands is chosen based on the durometer of the urethane or rubber. The top roll of the exit pull stand preferably utilizes a Teflon sleeve which will not react with the polymers used in the process. The bottom roll of the exit pull stand is preferably chrome plated or highly polished steel to reduce the impression into the preplaced polymer in the web.

If desired, non-contact antistatic devices may be installed in locations where noticeable levels of static buildup are detected. However, there is no evidence of adverse effects due to static buildup in the process.

Blade thickness and shape have substantial effects on the movement of the structural elements of the web during processing and more importantly, the viscoelastic flow characteristics of the polymer in controlling (a) the thin film encapsulation of the individual fibers and filaments, (b) the controlled placement of the internal coating, and (c) the controlled placement of the additives in (a) and (b). The blade bevel can effect the entry angle of the web and effect the sharpness of the leading edge of the blade. A sharper leading edge has a greater ability to push the weave or structural elements of the web longitudinally and traversely, increasing the size of the interstitial spaces. As the web passes the leading edge of the blade, the interstitial spaces snap back or contract to their original size. The polymer viscosity is reduced and the polymer is placed into the web at the leading edge of the blade. Blade thickness and shape effects the polymers and their selected additives and the placement thereof. Preferably, the combination of the leading edge condition and the two surfaces (the front and the bottom) that meet at the leading edge are RMS 8 or better in grind and/or polish. This creates a precise leading edge; the more precise the leading edge, the more the shear thinning control.

There are a number of pre-qualifiers or engineered attributes of polymers that enhance control of flow and polymer placement in:(a) the thin film encapsulation of the individual fibers and filaments, (b) the controlled placement of the internal coating, and (c) the controlled placement of the additives in (a) and (b). Blending polymers is one way to achieve ideal flow and placement characteristics. An example of a blended polymer is where one polymer, selected for its physical properties, is mixed with another polymer that is selected for its viscosity altering properties. Many tests using different polymer blends have been done. Polymer blends vary by both chemical and physical adhesion, durability, cure dwell time required, cure temperature required, flexibility, percentage add-on required, performance requirements, and aesthetics.

Accelerators and inhibitors which are added to polymers, generally produce three effects. An illustrative accelerator or inhibitor is a platinum catalyst, which is a cure or crosslinking enhancer. The first effect it produces is to control the time and temperature of the web as it cures. A cure or controlled crosslinking enhancer can significantly assist in controlling the drape and hand feel of the web. The second effect is to to alter the cure to allow the web to reach partial cure and continue curing after leaving an initial heat zone. This second effect also assists in retaining the drape and hand feel of the web. The third effect of inhibitors is to achieve a semi-cure for later staging of the cure.

Additives which are added to the polymers significantly control surface chemistry. Surface chemistry characteristics are controlled by including additives that have both reactive and biointeractive capabilities. The method and apparatus of this invention can control the placement of the additives on the surface of the thin film encapsulating the fibers, on either or both surfaces of the internal layer, on either or both surfaces of the web, or any combination of the foregoing.

The oven cure temperature and the source and type of cure energy, are controlled for a number of reasons. The oven cure temperature is controlled to achieve the desired crosslinked state; either partial or full. The source and type of energy can also affect the placement of the polymer and additives. For example, by using a high degree of specific infrared and some convection heat energy for cure, some additives can be staged to migrate and/or bloom to the polymer surfaces.

Oven cure temperature is thermostatically controlled to a predetermined temperature for the web and polymers used. Machine runs of new webs are first tested with hand pulls to determine adhesion, cure temperature, potentials of performance values, drapability, aesthetics, etc. The effect on the web depends on the oven temperature, dwell time and curing rate of the polymer. Webs may expand slightly from the heat.

Oven cure dwell time is the duration of the web in the oven. Oven cure dwell time is determined by the speed of the oven's conveyor and physical length of the oven. If the dwell time and temperature for a particular web is at maximum, then the oven conveyor speed would dictate the speed of the entire process line or the length of the oven would have to be extended in order to increase the dwell time to assure proper final curing of the web.

The physical construction and chemistry of the web is critical. The amount of control over the rheology of the polymer and the tension on the web are dependent on the physical construction and chemistry. The web selected must have physical characteristics that are compatible with the flow characteristics of the polymer.

The ambient polymer temperature refers to the starting or first staging point to controlling the viscosity and rheology. The process head can control the ambient polymer temperature through temperature controlled polymer delivery and controlled blade temperatures.

Humidity can sometimes inhibit or accelerate curing of the polymer. Therefore, humidity needs to be monitored and, in some conditions, controlled.

The degree the web is deformed under lateral tension is controllable by the choice of the physical construct of the web, the blade angle, the blade leading edge condition, and the micro and macro tension of the web.

Airborne contaminants and lint on the web can affect primability and can create pin holes in the polymer. Therefore, airborne contaminants and lint on the web need to be controlled to reduce or eliminate pin holes or uncontrolled primability.

In view of the fact that between the shear thinning stations and the oven, the polymer composition may begin to set or partially cure, it may be desirable to overshear so that by the time the web gets to the curing oven, it will be at the point where it is desired that the cure occur. This over shear effect is a matter of controlling certain variables, including the force of the blades against the moving web, as well as the tension and speed of the web.

By having a number of shear thinning blades, you create a multiple shear thinning effect, which changes the final construct of the polymer and the (a) thin film encapsulation of the individual fibers and filaments, (b) controlled placement of the internal coating, and (c) controlled placement of the additives in (a) and (b). It is understood that the first shear thinning causes viscoelastic deformation of the polymer composition which, due to its memory, tends to return to a certain level. With each multiple shear thinning, the level to which the polymer starts at that shear point and returns is changed. This is called thixotropic looping or plateauing (See FIG. 1).

Definitions

As employed herein, the term "adhesiveness" refers to the capacity to bind other solids by both chemical and physical means The term "analyte," as used herein, refers to any molecule, molecular complex or particles in a fluid that is measurable or can be isolated using the barrier webs of the present invention. This term is also meant to include large particles such as cells and microorganisms, including viruses, bacteria, protozoa and fungi or components of the microorganisms such as proteins, peptides, glycoproteins, lipids, ribonucleic acid or sugars. The term "analyte" also includes latex particles or other particulate matter.

The phrase "antistatic character," as used herein, refers to the capacity to reduce the generation of charge, increase the rate of charge dissipation, inhibit the production of charge, or some combination of the foregoing.

The term "bioactive surfaces," as used herein, includes, but is not limited to, the incorporation of antibodies, antigens, enzymes, or other bioactive molecules into the polymer to be applied to a fabric or other surface thereby forming a surface with the bioactive molecule attached thereto.

The phrase "biocidal activity," as used herein, refers to the capacity of a compound to kill pathogenic and/or non-pathogenic microorganisms, and prevent or inhibit the action or growth of microorganisms including viruses and bacteria. Biocidal activity can be measured by applying Test Methods 100-1993, 147-1993, and 174-1993 of the Technical Manual of the American Association of Textile Chemist and Colorist (AATCC), Dow Corning Corporate Test Method 0923, and the Kirby-Bauer Standard Antimicrobial Susceptibility Test as described in the Manual of Clinical Microbiology, Fourth Edition, all of which are incorporated herein by reference.

As employed herein, the term "biocide," as used herein, refers to any physical or chemical agent capable of combating pathogenic and non-pathogenic microorganisms, including bacteria and viruses.

As employed herein, the phrase "biological activity" refers to the functionality, reactivity, and specificity of compounds that are derived from biological systems or those compounds that are reactive to them, or other compounds that mimic the functionality, reactivity, and specificity of these compounds. Examples of suitable biologically active compounds include enzymes, antibodies, antigens and proteins.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

The term "breathability," as used herein, refers to gas permeability such as the moisture vapor transmission of a material as measured by ASTM E96 and the specifically developed modified "Bellow's Test" described in subsequent sections.

The term "coating" as used herein, refers to a generally continuous film or layer formed by a material over or on a surface.

As employed herein, the phrase "color fastness" refers to the capacity of a fabric to resist fading during a period of normal wear and multiple washings and dry cleaning. Color fastness is determined under conditions of accelerated weathering.

With respect to the polymer compositions used in this invention, the term "controlled placement" or "placement" refers to the penetration of such polymer compositions into a porous web, to the distribution of such composition in a controlled manner through such web, and to the resultant, at least partial envelopment of at least a portion of the fibers of such web by such composition in accordance with the present invention, or to the formation of an internal layer, or both.

The term "curing", or "cure", as used herein, refers to a change in state, condition, and/or structure in a material, such as a curable polymer composition that is usually, but not necessarily, induced by at least one applied variable, such as time, temperature, radiation, presence and quantity in such material of a curing catalyst or curing accelerator, or the like. The term "curing" or "cured" covers partial as well as complete curing. In the occurrence of curing in any case, such as the curing of such a polymer composition that has been selectively placed into a porous flexible substrate or web, the components of such a composition may experience occurrence of one or more of complete or partial (a) polymerization, (b) cross-linking, or (c) other reaction, depending upon the nature of the composition being cured, application variables, and presumably other factors. It is to be understood that the present invention includes polymers that are not cured after application or are only partially cured after application.

As employed herein, the term "durability" refers to the capacity of a fabric to retain its physical integrity and appearance during a period of normal wear and multiple washings and dry cleaning.

The term "elastomeric" as used herein refers to the ability of a cured polymer treated web to stretch and return to its original state.

The phrase "electrical conductivity," as used herein refers to the capacity to conduct electrical current.

The phrase "electromagnetic radiation absorptivity," as used herein, refers to the absorption of radiation of wavelengths from within the electromagnetic spectrum.

The phrase "electromagnetic shielding capacity," as used herein, refers to the capacity to reflect, absorb, or block electromagnetic radiation.

The term "envelop" or "encapsulate" as used interchangeably herein, refers to the partial or complete surrounding, encasement, or enclosing by a discrete layer, film, coating, or the like, of exposed surface portions of at least some individual fiber or lining of a cell or pore wall of a porous web. Such a layer can sometimes be contiguous or integral with other portions of the same enveloping material which becomes deposited on internal areas of a web which are adjacent to such enveloping layer, enveloped fiber, lined cell or pore wall, or the like. The thickness of the enveloping layer is generally in the range of 0.01 to 50 microns, and preferably in the range of about 0.1 to 20 microns.

The term "fiber", as used herein, refers to a long, pliable, cohesive, natural or man-made (synthetic) threadlike object, such as a monofilament, staple, filament, or the like. A fiber usable in this invention preferably has a length at least 100 times its diameter or width. Fibers can be regarded as being in the form of units which can be formed by known techniques into yarns or the like. Fibers can be formed by known techniques into woven or non-woven webs (especially fabrics) including weaving, knitting, braiding, felting, twisting, matting, needling, pressing, and the like. Preferably, fibers, such as those used for spinning, as into a yarn, or the like, have a length of at least about 5 mm. Fibers such as those derived from cellulosics of the type produced in paper manufacture can be used in combination with longer fibers as above indicated, as those skilled in the art will readily appreciate.

The term "filament" as used herein refers to a fiber of indefinite length.

The term "filled" as used herein in relation to interstices, or interstitial spaces, or open cells, and to the amount of polymer composition therein in a given web, substrate, or the fibers in such web or substrate, designates the presence of such composition therein. When a given interstitial space or open cell is totally taken up by such composition, it is "completely filled" or "plugged". The term "filled" also refers to an interstitial space having a film or layer of polymer composition over or through it so that it is closed even though the entire thickness of the interstitial space is not completely filled or plugged.

Measurements of the degree of envelopment, interstitial fillage, plugging, or the like in an internal coating are conveniently made by microscopy, or preferably by conventional scanning electron microscopy (SEM) techniques. Because of the nature of such measuring by SEM for purposes of the present invention, "a completely filled" interstitial space or open cell can be regarded as a "plugged" interstitial space or open cell.

The term "flattening agent," as used herein, refers to a compound that dulls the finish on glossy fabrics.

The term "flow" or "flowability" as used herein means the altering of the rheology of a material by the application of energy to a suitable material so as to allow the flowing of the material to form: (a) a thin film of a polymer composition encapsulating the structural elements (i.e., the fibers or filaments) making up the web leaving at least some of the interstitial spaces open; (b) an internal layer of a polymer composition between the upper and lower surfaces of the web; or (c) some combination of the foregoing.

The phrase "fluid resistance," as used herein, refers to the ability of a material to resist the penetration of fluids. Fluid resistance is measured by the Rain test, Suter test, and hydrostatic resistance measurements, discussed in the "Examples" section and incorporated herein by reference. Fluid resistance, for purposes of the present invention, is the result of two conditions. First, the surface of the web has the potential for increased fluid resistance due to the choice of the polymer and also the choice of additives and/or modifiers to control surface energies. Second, the external fluid resistant or fluid proof properties can be altered by controlling the effective pore size of the web. Additives and/or modifiers can serve to increase or decrease the effective pore size by controlling the viscosity and rheology achieved through the processing of polymer in the machine. In addition, the bimodal distributions of pore sizes found in a woven fabric are controlled by the processing. The larger pore sizes are supplied by the spaces between yarns while smaller pores reflect the yarn structure and the polymer composition pore size.

As employed herein, the term "functional" refers to a particular performance attribute such as biocidal activity, therapeutic activity, ion-exchange capacity, biological activity, biological interactive capacity to bind compounds, surface chemistry activity, electromagnetic radiation absorptivity, adhesiveness, hand, durability, color fastedness, light reflectivity, fluid resistance, waterproofness, breathability, mildew resistivity, rot resistivity, stain resistivity, electrical conductivity, thermal conductivity, antistatic character, processability, rheological character, electromagnetic shielding capacity, and radio frequency shielding capacity.

The term "hand" refers to the tactile feel and drapability or quality of a fabric as perceived by the human hand.

With respect to the fluorochemical liquid dispersions (or solutions) which can optionally be used for web pretreatment, the term "impregnation" refers to the penetration of such dispersions into a porous web, and to the distribution of such dispersions in a preferably, substantially uniform and controlled manner in such web, particularly as regards the surface portions of the individual web component structural elements and fibers.

The terms "internal coating" or "internal layer" can be used interchangeably. As used herein, the terms refer to a region generally spaced from the outer surfaces of the web which is substantially continuously filled by the combination of the polymer controllably placed therein and the fibers and filaments of the web in the specified region. Such coating or layer envelopes, and/or surrounds, and/or encapsulates individual fibers, or lines cell or pore walls of the porous web or substrate, in the specified region. The internal layer is not necessarily flat but may undulate or meander through the web, occasionally even touching one or both surfaces of the web. Generally, the internal layer is exposed on both sides of a web as part of the multi complex structure of a woven and non-woven web. The thickness of the internal layer is generally in the range of 0.01 to 50 microns, and preferably in the range of about 0.1 to 20 microns.

As used herein, the phrase "ion-exchange capacity" refers to the capacity to exchange mobile hydrated ions of a solid, equivalent for equivalent, for ions of like charge in solution.

The phrase "light reflectivity," as used herein, refers to the capacity to reflect light from the visual region of the electromagnetic spectrum The phrase "mildew resistance," as used herein, refers to the capacity to either kill or prevent or inhibit the growth of mildew. Mildew resistance can be quantified by Test Method 30-1993 of the Technical Manual of the American Association of Textile Chemist and Colorist (AATCC), incorporated herein by reference.

The term "modifiers," "agents," or "additives," used interchangeably herein, refers to materials and compounds that impart or alter specific physical or chemical characteristics with respect to the articles produced therefrom. These physical or chemical characteristics are typically functional properties. The modifiers may also alter or impart functional properties to the thixotropic material. Examples of modifiers suitable for use in the practice of the present invention include biocides, therapeutic agents, nutrients, adhesive agents, humidity-controlling agents, water repellents, ion-exchange agents, light-reflective agents, dyes and pigments, mildew-resistance agents, conductive agents, proteins, hand-altering agents, blood repellents, flexibility-inducing agents, light fastness-inducing agents, rot-resistant agents, stain-resistant agents, grease-resistant agents, ultraviolet-absorbing agents, fillers, flattening agents, electrical conductive agents, thermal conductive agents, flame retardants, antistatic agents, electromagnetic shielding agents, and radio frequency shielding agents. Examples of suitable nutrients which can be employed in the practice of the present invention include cell growth nutrients.

The term "particle," as used herein, refers to any particulate matter including, but not limited to, microorganisms including viruses, bacteria, protozoa, or fungi, cells and cell fragments such as platelets, as well as inanimate particles such as latex particles. The term "particle," as used herein, can also mean molecules.

The term "polymer", or "polymeric" as used herein, refers to monomers and oligomers as well as polymers and polymeric compositions, and mixtures thereof, to the extent that such compositions and mixtures are curable and shear thinnable.

As employed herein, the term "processability" refers to the nature of a material with respect to its response to various processing methods and process parameters. Processing agents contemplated for use in the practice of the present invention could also include cross-link inhibitors that either delay the onset of cure or slow the cure rate of the curable, thixotropic material, and thixotropy inducing or rheological agents that, for example, alter the viscosity of the curable material, and the like.

The phrase "radio frequency shielding capacity," as used herein, refers to the capacity to reflect, absorb, or block radio frequency waves.

As employed herein, the phrase "rheological character" refers to material attributes such as flow, viscosity, elasticity, and the like.

As employed herein, the phrase "rot resistance" refers to the capacity to prevent or inhibit the decay of naturally-derived materials.

The term "shear thinning," in its broadest sense, means the lowering of the viscosity of a material by the application of energy thereto.

The phrase "stain resistance," as used herein, refers to the ability of a material to resist coloring by a solution or a dispersion of colorant. Waterborne stain resistance refers to the ability to resist coloring by a waterborne stain.

As employed herein, the quantity meant by the term "sufficient" will depend on the nature of the energy source, the porous substrate, the curable, thixotropic material, the additives and/or modifiers used, and the desired functional properties of the article produced therefrom. A description of the method and several examples are provided to provide enough guidance to one of skill in the art to determine the amount of energy required to practice this invention.

As employed herein, the phrase, "surface chemistry activity" refers to the composition, reactivity, and positioning of chemical moities on the surfaces of the porous substrate. As contemplated for use in the practice of the present invention, modifiers that alter the surface chemistry of the resulting article include fluorochemical compounds, proteins, and any other modifier compound that can be selectively positioned at the various surfaces within the porous substrate.

The phrase "therapeutic activity," as employed herein, refers to the capacity to treat, cure, or prevent a disease or condition. As employed herein, the term "therapeutic agents" refers to compound(s) that are effective at treating, curing, or preventing a disease or condition.

The phrase "thermal conductivity," as used herein refers to the capacity to conduct heat.

The word "thixotropy" refers herein to liquid flow behavior in which the viscosity of a liquid is reduced by shear agitation or stirring so as to allow the placement of the liquid flow to form: (a) a thin film of a polymer composition encapsulating the structural elements (i.e., the fibers or filaments) making up the web leaving at least some of the interstitial spaces open; (b) an internal layer of a polymer composition between the upper and lower surfaces of the web; or (c) some combination of the foregoing. It is theorized to be caused by the breakdown of some loosely knit structure in the starting liquid that is built up during a period of rest (storage) and that is broken down during a period of suitable applied stress.

As employed herein, the phrase "waterproofness" refers to the wetting characteristic of a material with respect to water. Waterproofness is measured using the Mullen Test, Federal Standard 191, method 5 512, incorporated herein by reference.

The term "web" as used herein is intended to include fabrics and refers to a sheet-like structure (woven or non-woven) comprised of fibers or structural elements. Included with the fibers can be non-fibrous elements, such as particulate fillers, binders, dyes, sizes and the like in amounts that do not substantially affect the porosity or flexibility of the web. While preferably, at least 50 weight percent of a web treated in accordance with the present invention is fibers, more preferred webs have at least about 85 weight percent of their structure as fiber. It is presently preferred that webs be untreated with any sizing agent, coating, or the like, except as taught herein. The web may comprise a laminated film or fabric and a woven or non-woven porous substrate. The web may also be a composite film or a film laminated to a porous substrate or a double layer.

The term "webs" includes flexible and non-flexible porous webs. Webs usable in the practice of this invention can be classified into two general types:

(A) Fibrous webs; and (B) Substrates having open cells or pores, such as foams.

A porous, flexible fibrous web is comprised of a plurality of associated or interengaged fibers or structural elements having interstices or interstitial spaces defined therebetween. Preferred fibrous webs can include woven or non-woven fabrics. Other substrates include, but are not limited to, a matrix having open cells or pores therein such as foams or synthetic leathers.

The term "wound dressing" as used herein means any web or fabric that is used to cover a wound. This term includes bandages, surgical gauze, surgical dressings, burn dressings and the like.

The term "yarn" as used herein refers to a continuous strand comprised of a multiplicity of fibers, filaments, or the like in a bundled form, such as may be suitable for knitting, weaving or otherwise used to form a fabric. Yarn can be made from a number of fibers that are twisted together (spun yarn) or a number of filaments that are laid together without twist (a zero-twist yarn).

A flexible porous web used as a starting material in the present invention is generally and typically, essentially planar or flat and has generally opposed, parallel facing surfaces. Such a web is a three-dimensional structure comprised of a plurality of fibers with interstices therebetween or a matrix having open cells or pores therein. The matrix can be comprised of polymeric solids including fibrous and non-fibrous elements.

Three principal classes of substrates having open pores or cells may be utilized in the present invention: leathers (including natural leathers, and man-made or synthetic leathers), foamed plastic sheets (or films) having open cells, and filtration membranes.

Foamed plastic sheet or film substrates are produced either by compounding a foaming agent additive with resin or by injecting air or a volatile fluid into the still liquid polymer while it is being processed into a sheet or film. A foamed substrate has an internal structure characterized by a network of gas spaces, or cells, that make such foamed substrate less dense than the solid polymer. The foamed sheets or film substrates used as starting materials in the practice of this invention are flexible, open-celled structures.

Natural leathers suitable for use in this invention are typically split hides. Synthetic leathers have wide variations in composition (or structure) and properties, but they look like leather in the goods in which they are used. For purposes of technological description, synthetic leathers can be divided into two general categories: coated fabrics and poromerics.

Synthetic leathers which are poromerics are manufactured so as to resemble leather closely in breathability and moisture vapor permeability, as well as in workability, machinability, and other properties. The barrier and permeability properties normally are obtained by manufacturing a controlled microporous (open celled) structure.

Synthetic leathers which are coated fabrics, like poromerics, have a balance of physical properties and economic considerations. Usually the coating is either vinyl or urethane. Vinyl coatings can be either solid or expanded vinyl which has internal air bubbles which are usually a closed-cell type of foam. Because such structures usually have a non-porous exterior or front surface or face, such structures display poor breathability and moisture vapor transmission. However, since the interior or back surface or face is porous, such materials can be used in the practice of this invention by applying the curable, thixotropic material and one or more modifier to the back face thereof.

Filtration membranes contemplated for use in the practice of the present invention include microporous membranes, ultrafiltration membranes, asymmetric membranes, and the like. Suitable membrane materials include polysulfone, polyamide, polyimide, nitrocellulose, cellulose acetate, nylon and derivatives thereof.

Other porous webs suitable for use in the practice of the present invention include fibers, woven and non-woven fabrics derived from natural or synthetic fibers, papers, and the like. Examples of papers are cellulose-based and glass fiber papers.

The fibers utilized in a porous flexible web treated by the methods and apparatus of the present invention can be of natural or synthetic origin. Mixtures of natural fibers and synthetic fibers can also be used. Examples of natural fibers include cotton, wool, silk, jute, linen, and the like. Examples of synthetic fibers include acetate, polyesters (including polyethyleneterephthalate), polyamides (including nylon), acrylics, olefins, aramids, azlons, glasses, modacrylics, novoloids, nytrils, rayons, sarans, spandex, vinal, vinyon, regenerated cellulose, cellulose acetates, and the like. Blends of natural and synthetic fibers can also be used.

A porous web or fabric is preferably untreated or scoured before being treated in accordance with the present invention. Preferably a web can be preliminarily treated, preferably saturated, for example, by padding, to substantially uniformly impregnate the web with a fluorochemical. Typically, and preferably, the treating composition comprises a dispersion of fluorochemical in a liquid carrier. The liquid carrier is preferably aqueous and can be driven off with heat after application. The treating composition has a low viscosity, typically comparable to the viscosity of water or less. After such a treatment, it is presently preferred that the resulting treated web exhibits a contact angle with water measured on an outer surface of the treated web that is greater than about 90 degrees. The treated web preferably contains fluorochemical substantially uniformly distributed therethrough. Thus, the fluorochemical is believed to be located primarily on and in the individual fibers, cells or pores with the web interstices or open cells being substantially free of fluorochemical.

A presently preferred concentration of fluorochemical in a treatment composition is typically in the range of about 1 to about 10% fluorochemical by weight of the total treating composition weight, and more preferably is about 2.5% of an aqueous treating dispersion. Web weight add-ons of the fluorochemical can vary depending upon such factors as the particular web treated, the polymer composition to be utilized in the next step of the treatment process of this invention, the ultimate intended use and properties of the treated web of this invention, and the like. The fluorochemical weight add-on is typically in the range of about 0.01 to about 5% of the weight of the untreated web. After fluorochemical controlled placement, the web is preferably squeezed to remove excess fluorochemical composition after which the web is heated or otherwise dried to evaporate carrier liquid and thereby also accomplish fluorochemical insolubilization or sintering, if permitted or possible with the particular composition used.

The fluorochemical treated web thereafter has a predetermined amount of a curable polymer composition controllably placed within the web by the methods and apparatus of this invention, to form a web whose fibers, cells or pores are at least partially enveloped or lined with the curable polymer composition, whose web outer surfaces are substantially free of the curable polymer, whose web interstices or open cells are not completely filled with the curable polymer and which may also contain an internal layer of polymer. The curable polymer composition utilized preferably exhibits a starting viscosity greater than 1,000 centipoise and less than 2,000,000 centipoise at rest at 25° C. at a shear rate of 10 reciprocal seconds.

The fluorochemical residue that remains after web treatment may not be exactly evenly distributed throughout the web, but may be present in the web in certain discontinuities. For example, these discontinuities may be randomly distributed in small areas upon an individual fiber's surface. However, the quantity and distribution of fluorochemical through a web is believed to be largely controllable. Some portions of the fluorochemical may become dislodged from the web and migrate through the polymer due to the forces incurred by the shear thinning and controlled placement of the polymer.

The curable polymer composition is believed to be typically polymeric, (usually a mixture of co-curable polymers and oligomers), and to include a catalyst to promote the cure. The polymers that can be used in the present invention may be monomers or partially polymerized polymers commonly known as oligomers, or completely polymerized polymers. The polymer may be curable, partially curable or not curable depending upon the desired physical characteristics of the final product. The polymer composition can include conventional additives.

While silicone is a preferred composition, other polymer compositions include polyurethanes, fluorosilicones, silicone-modified polyurethanes, acrylics, polytetrafluoroethylene containing materials, and the like, either alone or in combination with silicones.

It is to be understood that the depth of polymer placement into a web can be controlled by the methods herein described to provide selective placement of the polymer within the web. Any additives and/or modifiers mixed into the polymer blend will likewise be selectively placed along with the polymer composition. The web is thereafter optionally cured to convert the curable composition into a solid elastomeric polymer.

The polymer composition is theorized to be caused to flow and distribute itself over fibers, cells or pores in a web under the influence of the processing conditions and apparatus provided by this invention. This flow and distribution is further theorized to be facilitated and promoted by the presence of a fluorochemical which has been preliminarily impregnated into a web, as taught herein. The amount of fluorochemical or fluorochemical residue in a web is believed to influence the amount, and the locations, where the polymer will collect and deposit, and produce encapsulated fibers and/or an internal layer in the web. However, there is no intent to be bound herein by theory.

Some portion of the residue of fluorochemical resulting from a preliminary web saturating operation is theorized to be present upon a treated fiber's surfaces after envelopment of fibers, cells or pores by the polymer has been achieved during the formation of the encapsulating fiber and/or the internal layer by the practice of this invention. This is believed to be demonstrated by the fact that a web treated by this invention still exhibits an enhanced water and oil repellency, such as is typical of fluorochemicals in porous webs. It is therefore believed that the fluorochemicals are affecting the adherence of the polymer as a thin film enveloping layer about the treated fibers, cells or pores as well as facilitating polymer pressurized flow within and about the interstices or open cells of the web being treated so that the polymer can assume its position enveloping the fibers or lining the cells or pores of the substrate.

In those fabrics that are pre-treated with fluorochemicals, the exact interrelationship between the polymer film and the impregnated fluorochemical is presently difficult, or perhaps impossible, to quantify because of the variables involved and because transparent polymer is difficult to observe by optical microscopy. It can be theorized that perhaps the polymer and the fluorochemical each tend to produce discontinuous films upon the fiber surface, and that such films are discontinuous in a complementary manner. It may alternatively be theorized that perhaps the polymer film is contiguous, or substantially so, relative to fluorochemical molecules on a fiber surface, and that the layer of polymer on a fiber surface is so thin that any dislodgement of the fluorochemical may release the fluorochemical into the polymer film thereby allowing the fluorine to orient or project through the film with the required cure temperature of the polymer, reactivating the water surface contact angle so that the water repellent properties of the fluorochemical affect the finished product. However, regardless of physical or chemical explanation, the combination of polymer film and fluorochemical results in a fiber envelopment or cell or pore wall lining and the formation of encapsulated fibers and/or an internal layer of polymer in a web when this invention is practiced. After curing, the polymer is permanently fixed material.

By using the methods of this invention, one can achieve a controlled placement of one or more additives and/or modifiers on and within the (a) thin film encapsulation of the individual fibers and filaments, (b) the controlled placement of the internal coating, and (c) some combination of (a) and (b).

A curable polymer optionally mixed with one or more additives and/or modifiers is applied onto and into a tensioned web using compressive and shear forces. The extent of orienting additives and/or modifiers on and within the fiber envelopment and the cell or pore wall lining is believed to be regulatable. Regulating such orientation is accomplished by controlling the factors discussed previously, the selection and amount of fluorochemical, the type of polymer and additives (and/or modifiers) used, and the amount of compressive and shear forces employed at a given temperature. Such control ensures that fiber envelopment is achieved while the interstices and/or open cells of the web are not completely filled with such polymer in the region of the internal layer and that the outer opposed surfaces of the web are substantially completely free of polymer coating or residue. After such a procedure, the curable polymer is cured.

The curable polymer is optionally mixed with one or more additives and/or modifiers and then applied onto the surface of the web. Then the web, while tensioned, is passed over and against shearing means or through a compression zone, such as between rollers or against a shear knife. Thus, transversely applied shear force and compressive pressure is applied to the web. The combination of tension, shearing forces, and web speed is sufficient to cause the polymer composition to move into the web and out from the interstices or open cells around the web fibers, cells, or pores being enveloped. The result is that at least some of the interstices and/or open cells are unfilled in regions of the web outside of the region occupied by the internal coating or internal layer, and are preferably substantially free of polymer. Excess polymer is removed by the surface wiping action of the shearing means. The curable polymer enveloping the fibers is thereafter cured.

The desired penetration of, and distribution and placement of polymer and additives and/or modifier(s) in a web is believed to be achieved by localized pressuring forces exerted on a web surface which are sufficiently high to cause the viscosity of a polymer composition to be locally reduced, thereby permitting such polymer to flow under such pressuring and to be controllably placed within the web and to envelope its fibers or line the cell or pore walls thereof. To aid in this process, the web is preferably at least slightly distorted by tensioning or stretching, while being somewhat transversely compressed at the location of the controlled placement. This distortion is believed to facilitate the entrance of the polymer composition into the web and the orientation of one or more additives and/or modifiers onto and into the web. When the compression and tension are released, the polymer composition is believed to be squeezed or compressed within and through the interstitial spaces, or open cell spaces, of the treated web.

If, for example, too much polymer is present in the finished product, then either or both the tension and shear force can be increased, and vice versa for too little polymer. If flow is not adequate upon the fibers, producing incomplete fiber envelopment, then the viscosity of the polymer composition can be reduced by increasing the pressures and/or temperatures employed for the controlled placement thereof. Alternatively, if the viscosity is too low, then the pressure and/or temperature can be decreased. If the polymer composition is resistant to being positioned or placed in a desired location in a desired amount in a given web at various viscosities and/or pressures, then the level of fluorochemical pretreatment of the web can be increased, or decreased, as the case may be. The above factors also influence the placement of additives and/or modifiers when the additives and/or modifiers are mixed into the polymer composition.

Some additives and/or modifiers, due to their physical and chemical properties, cannot be incorporated on and within a web by pre-treating the web or by mixing the additives and/or modifiers into the polymer composition. Such additives and/or modifiers can be topically applied to the web after the pressured, shear thinning stage described above, but before curing. Once topically applied, the additives and/or modifiers are forced into the web by passing through the exit nip rolls. The additives and/or modifiers will adhere to the polymer composition that forms encapsulated fibers, an internal layer, or some combination of the above. Some additives and/or modifiers may even adhere to the structural elements of the web.

As indicated above, the activity transpiring at a final step in the practice of this invention is generically referred to as curing. Conventional curing conditions known in the prior art for curing polymer compositions are generally suitable for use in the practice of this invention. Thus, temperatures in the range of about 250° F. to about 350° F. are used and times in the range of about 30 seconds to about 1 minute can be used, although longer and shorter curing times and temperatures may be used, if desired, when thermal curing is practiced. Radiation curing, as with an electron beam or ultraviolet light can also be used. However, using platinum catalysts to accelerate the cure while using lower temperatures and shorter cure times is preferable.

Since either filled, plugged, almost filled interstices, or open cells in the region of an internal layer remain transmissive of air in cured webs made by this invention, the webs are characteristically air permeable or breathable.

Sample webs or fabrics that are beneficially treated, fiber enveloped and internally coated in accordance with the invention include nylon, cotton, rayon and acrylic fabrics, as well as fabrics that are blends of fiber types. Sample nylon fabrics include lime ice, hot coral, raspberry pulp, and diva blue Tactel® (registered trademark of ICI Americas, Inc.) fabrics available from agent Arthur Kahn, Inc. Sample cotton fabrics include Intrepid® cotton cornsilk, sagebrush cotton, and light blue cotton fabrics available also from Arthur Kahn, Inc. Non-woven, monofilamentous, fabrics such as TYVEK® (registered trademark of E.I. dupont de Nemours Co., Inc.) and the like are also employable.

As indicated above, a web is preferably pretreated and impregnated with a fluorochemical prior to being treated with a polymer composition as taught herein. The fluorochemical impregnation is preferably accomplished by first saturating a web with a liquid composition which incorporates the fluorochemical, and then, thereafter, removing the excess liquid composition and residual carrier fluid by draining, compression, drying, or some combination thereof from the treated web.

It is now believed that any fluorochemical known in the art for use in web, particularly fabric treatment in order to achieve water repellency, soil repellency, grease repellency, or the like, can be used for purposes of practicing the present invention. It is believed that a typical fluorochemical of the type used for web treatment can be characterized as a compound having one or more highly fluorinated portions, each portion being a fluoroaliphatic radical or the like, that is (or are) functionally associated with at least one generally non-fluorinated organic portion. Such organic portion can be part of a polymer, part of a reactive monomer, a moiety with a reactable site adapted to react with a binder, or the like. Such a compound is typically applied to a fabric or other web as a suspension or solution in either aqueous or non-aqueous media. Such application may be conventionally carried out in combination with a non-fluorine or fluorine containing resin or binder material for the purpose of providing improved durability as regards such factors as laundering, dry cleaning, and the like.

Fluorochemicals are sometimes known in the art as durable water repellent (DWR) chemicals, although such materials are typically believed to be not particularly durable and to have a tendency to wash out from a fabric treated therewith. In contrast, fiber enveloped webs of this invention which have been pretreated with a fluorochemical display excellent durability and washability characteristics. Indeed, the combination of fluorochemical pretreatment and silicone polymer fiber envelopment such as provided by the present invention appears to provide synergistic property enhancement because the effects or properties obtained appear to be better than can be obtained than by using either the fluorochemical or the silicone polymer alone for web treatment.

Exemplary water repellent fluorochemical compositions include the compositions sold under the name Milease® by ICI Americas Inc. with the type designations F-14N, F-34, F-31X, F-53. Those compositions with the "F" prefix indicate that they contain a fluorochemical as the principal active ingredient. More particularly, Milease® F-14 fluorochemical, for example, is said to contain approximately 18 percent perfluoroacrylate copolymer, 10 percent ethylene glycol (CAS 107-21-1) and 7 percent acetone (CAS 67-64-1) dispersed and dissolved in 65 percent water. Milease® F-31X is said to be a dispersion of a combination of fluorinated resin, acetone, and water.

Still another suitable class of water repellent chemicals is the Phobotex® chemicals of Ciba/Geigy identified as Phototex® FC104, FC461, FC731, FC208 and FC232 which are each believed to be suitable for use, typically in approximately a 5 percent concentration, in saturating a web for use in the invention. These and many other water repellent fluorochemicals are believed to be capable of creating a surface contact angle with water of greater than about 90 degrees when saturated into a web and to be suitable for use in the practice of this invention.

Another group of useful water repellent fluorochemicals is the TEFLON® -based soil and stain repellents of E.I. dupont de Nemours & Co. Inc., 1007 Market Street, Wilmington, Del. 19898. Suitable TEFLON® types for use in the practice of this invention include TEFLON® G. NPA, SKF, UP, UPH, PPR, N. and MLV. The active water repellent chemical of each composition is believed to be a fluorochemical in polymeric form that is suitable for dispersion in water, particularly in combination with a cationic surfactant as a dispersant. These dispersions are dilutable in all proportions with water at room temperature. One preferred class of fluorochemical treating compositions useful in the practice of this invention comprises about 1 to about 10 weight percent, more preferably about 5 weight percent of one of the above indicated TEFLON®-type water repellent fluorochemcials in water.

Another major group of suitable water repellent fluorochemical compositions useful in the practice of the invention is commercially available under the designation ZEPEL® rain and stain repellent chemicals of E.I. duPont de Nemours & Co. Inc., such as ZEPEL® water repellent chemicals types B. D, K, RN, RC, OR, HT, 6700 and 7040. Each is believed to be a fluorochemical in polymeric form that is dispersible in all proportions at room temperature. The dispersants ZEPEL® B. D, K, and RN are believed to be cationic, while the dispersant ZEPEL® RC is believed to be nonionic.

As an exemplary composition, ZEPEL® 6700 is said to be comprised of 15 to 20 percent perfluoroalklyl acrylic copolymer, 1 to 2 percent alkoxylated carboxylic acid, and 3 to 5 percent ethylene glycol. Exemplary characteristics of the composition include a boiling point of 100° C. at 760 mm Hg and a specific gravity of 1.08. The volatiles are approximately 80 percent by weight. The pH is 2 to 5. The odor is mild; the concentrate form is that of a semi-opaque liquid; and the concentrate color is straw white. The composition and characteristics of ZEPEL® 7040 repellent chemical are believed to be substantially identical to those of ZEPEL® 6700 except that the former composition additionally contains 7 to 8 percent acetone.

Another major group of water repellent fluorochemicals comprises the Scotchgard® water repellent chemicals of 3M Co., St. Paul, Minn. The Scotchgard® fluorochemicals are believed to be aqueously dispersed fluorochemicals in polymeric form. The compositions of two suitable Scotchgard® water repellent fluorochemnicals are believed to be disclosed in U.S. Pat. Nos. 3,393,186 and 3,356,628, which patents are incorporated herein by reference. Thus, the Scotchgard® fluorochemical of U.S. Pat. No. 3,356,628 consists of copolymers of perfluoroacrylates and hydroxyalkyl acrylates. These copolymers are suitable for use as an oil and water repellent coating on a fibrous or porous surface. They have a carbon to carbon main chain and contain recurring monovalent perfluorocarbon groups having from 4 to 18 carbon atoms each and also having recurring hydroxyl radicals. From 20 to 70 percent of the weight of such copolymer is contributed by fluorine atoms in the perfluorocarbon groups and from 0.05 to 2 percent of the weight of the copolymer is contributed by the hydroxyl radicals. Such copolymer is said to have improved surface adherability properties as compared to the homopolymer of a corresponding fluorocarbon monomer.

The Scotchgard® fluorochemical of U.S. Pat. No. 3,393,186 consists of perfluoroalkenylacrylates and polymers thereof. An exemplary fluorinated monomer has the formula:

Wherein $R_f$ is a fluorocarbon group having from 3 to 18 carbon atoms, R is hydrogen or methyl, and n is 0–16. Such a water repellent fluorochemical composition is supplied and saturated into the substrate web as a readily pourable aqueous dispersion.

U.S. Pat. No. 4,426,476 discloses a fluorochemical textile treating composition containing a water-insoluble fluoroaliphatic radical, an aliphatic chlorine-containing ester and a water insoluble, fluoroaliphatic radical containing polymer.

U.S. Pat. No. 3,896,251 discloses a fluorochemical textile treating composition containing a fluoroaliphatic radical containing linear vinyl polymer having 10 to 60 weight percent fluorine and a solvent soluble carbodiimide preferably comprising fluoroaliphatic groups. A table in this patent lists a plurality of prior art fluoroaliphatic radical containing polymers useful for the treatment of fabrics and the prior art patents where such polymers are taught.

U.S. Pat. No. 3,328,661 discloses textile treating solutions of a copolymer of an ethylenically unsaturated fluorocarbon monomer and a ethylenically unsaturated epoxy group containing monomer.

U.S. Pat. No. 3,398,182 discloses fluorocarbon compounds useful for fabric treatment that contain a highly fluorinated oleophobic and hydrophobic terminal portion and a different nonfluorinated oleophilic portion linked together by a urethane radical.

Water repellent fluorochemical compositions are preferably utilized to saturate a starting untreated porous web substrate so that such composition and its constituents wet substantially completely and substantially uniformly all portions of the web. Such a saturation can be accomplished by various well known techniques, such as dipping the web into a bath of the composition, or padding the composition onto and into the web, or the like. Padding is the presently preferred method of fluorochemical application.

After application of the fluorochemical composition to the web, the water (or liquid warier) and other volatile components of the composition are removed by conventional techniques to provide a treated web that contains the impregnated fluorochemical throughout the web substrate.

In a preferred procedure of fluorochemical controlled placement, a web is substantially completely saturated with an aqueous dispersion of a fluorochemical. Thereafter, the resulting impregnated web is compressed to remove excess portions of said dispersion. Finally, the web is heated to evaporate the carrier liquid. If the fluorochemical is curable, then the heating also accomplishes curing. After the fluorochemical treatment, the fluorochemical is found only on or in the web structural elements or fibers and is substantially completely absent from the web interstices.

The fluorochemical concentration in the treating composition is such as to permit a treated fluorochemical containing web, after volatiles of the treating composition are removed, to exhibit a contact angle with water applied to an outer web surface which is greater than about 90. More preferably, the contact angle provided is greater than about 130.

The web weight add-on provided by the fluorochemical after removal of volatiles is usually relatively minor. However, the weight add on can vary with such factors as the nature of web treated, the type of polymer composition utilized in the next step of the process, the temperature at which the composition is applied, the ultimate use contemplated for a web, and the like.

Typical weight add-ons of fluorochemical are in the range of about 1 to about 10 percent of the original weight of the web. More preferably, such weight add-ons are about 2 to about 4 weight percent of the weight of the starting fabric.

Durability of a web that has been treated with a fluorochemical and durability of a web that is subsequently treated with a polymer can sometimes be improved by the conventional process of "sintering". The exact physical and chemical processes that occur during sintering are unknown. The so-called sintering temperature utilized is a function of the fluorochemical composition utilized and such temperature is frequently recommended by fluorochemical manufacturers. Typically, sintering is carried out at a temperature of about 130° C. to about 160° C. for a period of time of about 2 to about 5 minutes. Acid catalysts can be added to give improved durability to laundering and dry cleaning solvents.

The fluorochemical is believed to provide more than water or other repellent properties to the resulting treated web, particularly since the curable polymer is often itself a water repellent. Rather, and without wishing to be bound by theory, it is believed that the fluorochemical in a treated web provides relative lubricity for the treated fibers during the pressure application of the curable polymer. The polymer is applied under pressures which can be relatively high, and the polymer is itself relatively viscous, as is discussed herein. In order for the curable polymer to coat and envelope/web fibers, but not fill web interstitial voids, the fibers of the web may move over and against each other to a limited extent, thereby to permit entry of the polymer into and around the fibers. It is thought that the fluorochemical deposits may facilitate such fiber motion and facilitate envelopment during the pressure application and subsequent shearing processing.

Alternatively, the fluorochemical may inhibit deposition of the polymer at the positions of the fluorochemical deposits which somehow ultimately tends to cause thin enveloping layers of polymer to form on fibers.

The precise physics and chemistry of the interaction between the fluorochemical and the polymer is not understood. A simple experiment demonstrates movement of the liquid polymer as influenced by the presence of the fluorochemical:

A piece of fabric, for example the Red Kap Milliken poplin polyester cotton blend fabric, is cut into swatches. One swatch is treated with an adjuvant, for example a three percent solution of the durable water-repellent chemical Milease® F-31X. The treated swatch and an untreated swatch are each positioned at a 45 angle to plumb. A measured amount, for example one-half ounce, of a viscous polymer composition, for example the Mobay® 2530A/B silicon composition, is dropped onto the inclined surface of each swatch. The distance in centimeters that the composition flows downwards upon the surface of the swatch is measured over time, typically for 30 minutes.

A graphical plot of the flow of the silicone composition respectively upon the untreated and treated swatches over time can be prepared, such as shown in FIG. 1. At the expiration of 30 minutes the viscous composition has typically traveled a distance of about 8.8 centimeters upon the treated swatch, or a rate of about 0.29 centimeters per minute. At the expiration of the same 30 minutes, the viscous composition has typically traveled a lesser distance of about 7.1 centimeters upon the untreated swatch, or a rate of about 0.24 centimeters per minute. Qualitatively commensurate results are obtainable with other DWR fluorochemical adjuvants that facilitate the viscous flow of polymer compositions in accordance with the invention. Indeed, if desired, the simple flow rate test can be used to qualify an adjuvant compound for its employment within the method of the invention. The fluorochemical pretreated web generally increases the surface contact angle of the polymer while reducing the amount of saturation of the polymer into the fibers themselves.

The fluorochemical treated web is thereafter treated under pressure with a predetermined amount of a curable polymer composition to form a web whose fibers are preferably substantially completely enveloped with such curable polymer and whose outer surfaces and interstices are preferably substantially completely free of the curable polymer. The polymer is thereafter cured by heat, radiation, or the like. Even room temperature curing can be used. A polymer impregnated, fluorochemical pretreated web can be interveningly stored before being subjected to curing conditions depending upon the storage or shelf life of the treating silicone polymer composition.

A curable polymer composition utilized in the practice of this invention preferably has a viscosity that is sufficient to achieve an internal coating of the web. Generally, the starting viscosity is greater than about 1000 centipoise and less than about 2,000,000 centipoise at a shear rate of 10 reciprocal seconds. It is presently most preferred that such composition have a viscosity in the range of about 5,000 to about 1,000,000 centipoise at 25° C. Such a composition is believed to contain less than about 1% by weight of volatile material.

The polymer is believed to be typically polymeric and to be commonly a mixture of co-curable polymers, oligomers, and/or monomers. A catalyst is usually also present, and, for the presently preferred silicone polymer compositions discussed hereinafter, is platinum or a platinum compound, such as a platinum salt.

A preferred class of liquid curable silicone polymer compositions comprises a curable mixture of the following components:

(A) at least one organo-hydrosilane polymer (including copolymers);
(B) at least one vinyl substituted polysiloxane (including copolymers);
(C) a platinum or platinum containing catalyst; and
(D) (optionally) fillers and additives.

Typical silicone hydrides (component A) are polymethylhydrosiloxanes which are dimethyl siloxane copolymers. Typical vinyl terminated siloxanes are vinyldimethyl terminated or vinyl substituted polydimethylsiloxanes. Typical catalyst systems include solutions or complexes of chloroplatinic acid in alcohols, ethers, divinylsiloxanes, and cyclic vinyl siloxanes.

The polymethylhydrosiloxanes (component A) are used in the form of their dimethyl copolymers because their reactivity is more controllable than that of the homopolymers and because they result in tougher polymers with a lower cross-link density. Although the reaction with vinyl functional silicones (component B) does reportedly take place in 1:1 stoichiometry, the minimum ratio of hydride (component A) to vinyl (component B) in commercial products is reportedly about 2:1 and may be as high as 6:1. While the hydrosilation reaction of polymethylhydrosilane is used in both so called RTV (room temperature vulcanizable) and LTV (low temperature vulcanizable) systems, and while both such systems are believed to be useful in the practice of the present invention, systems which undergo curing at elevated temperature are presently preferred.

Elastomers produced from such a curing reaction are known to demonstrate toughness, tensile strength, and dimensional stability.

Particulate fillers are known to be useful additives for incorporation into liquid silicone polymer compositions. Such fillers apparently not only can extend and reinforce the cured compositions produced therefrom, but also can favorably influence thixotropic behavior in such compositions. Thixotropic behavior is presently preferred in compositions used in the practice of this invention. A terminal silanol (Si—OH) group makes such silanol siloxanes susceptible to reaction in curing, as is believed desirable.

It is believed that all or a part of component B can be replaced with a so called silanol vinyl terminated polysiloxane while using an organotin compound as a suitable curing catalyst as is disclosed in U.S. Pat. No. 4,162,356. However, it is presently preferred to use vinyl substituted polysiloxanes in component B.

A polymer composition useful in this invention can contain curable silicone resin, curable polyurethane, curable fluorosilicone, curable modified polyurethane silicones, curable modified silicone polyurethanes, curable acrylics, polytetrafluoroethylene, and the like, either alone or in combination with one or more compositions.

One particular type of silicone composition which is believed to be well suited for use in the controlled placement step of the method of the invention is taught in U.S. Pat. Nos. 4,472,470 and 4,500,584 and in U.S. Pat. No. 4,666,765. The contents of these patents are incorporated herein by reference. Such a composition comprises in combination:

(i) a liquid vinyl chain-terminated polysiloxane having the formula:

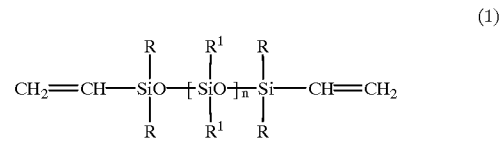

(1)

wherein R and R1 are monovalent hydrocarbon radicals free of aliphatic unsaturation with at least 50 mole percent of the R1 groups being methyl, and where n has a value sufficient to provide a viscosity of about 500 centipoise to about 2,000,000 centipoise at 25° C.;

(ii) a resinous organopolysiloxane copolymer comprising:
(a) $(R^2)_3SiO_{0.5}$ units and $SiO_2$ units, or
(b) $(R^3)_2SiO_{0.5}$ units, $(R^3)_2SiO$ units and $SiO_2$ units, or
(c) mixtures thereof, where $R^2$ and $R^3$ are selected from the group consisting of vinyl radicals and monovalent hydrocarbon radicals free of aliphatic unsaturation, where from about 1.5 to about 10 mole percent of the silicon atoms contain silicon-bonded vinyl groups, where the ratio of monofunctional units to tetrafunctional units is from about 0.5:1 to about 1:1, and the ratios of difunctional units to tetrafunctional units ranges up to about 0.1:1;]

(iii) a platinum or platinum containing catalyst; and (iv) a liquid organohydrogenpolysiloxane having the formula:

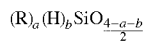

$$(R)_a(H)_b SiO_{\frac{4-a-b}{2}}$$

in an amount sufficient to provide from about 0.5 to about 1.0 silicon-bonded hydrogen atoms per silicon-bonded vinyl group of above component (i) or above subcomponent (iii) of, $R_a$ is a monovalent hydrocarbon radical free of aliphatic unsaturation, and has a value of from about 1.0 to about 2.1, b has a value of from about 0.1 to about 1.0, and the sum of a and b is from about 2.0 to about 2.7, there being at least two silicon-bonded hydrogen atoms per molecule.

Optionally, such a composition can contain a finely divided inorganic filler (identified herein for convenience as component (v)).

For example, such a composition can comprise on a parts by weight basis:

(a) 100 parts of above component (i);
(b) 100–200 parts of above component (ii);
(c) a catalytically effective amount of above component (iii), which, for present illustration purposes, can range from about 0.01 to about 3 parts of component (iii), although larger and smaller amounts can be employed without departing from operability (composition curability) as those skilled in the art will appreciate;
(d) 50–100 parts of above component (iv), although larger and smaller amounts can be employed without departing from operability (curability) as those skilled in the art will appreciate; and
(e) 0–50 parts of above component (v).

Embodiments of such starting composition are believed to be available commercially from various manufacturers under various trademarks and trade names.

As commercially available, such a composition is commonly in the two-package form (which are combined before use). Typically, the component (iv) above is maintained apart from the components (i) and (ii) to prevent possible gelation in storage before use, as those skilled in the art appreciate. For example, one package can comprise components (i) and (ii) which can be formulated together with at least some of component (ii) being dissolved in the component (i), along with component (iii) and some or all of component (v) (if employed), while the second package can comprise component (iv) and optionally a portion of component (v) (if employed). By adjusting the amount of component (i) and filler component (v) (if used) in the second package, the quantity of catalyst component (iii) required to produce a desired curable composition is achieved. Preferably, component (iii) and the component (iv) are not included together in the same package. As is taught, for example, in U.S. Pat. No. 3,436,366 (which is incorporated herein by reference), the distribution of the components between the two packages is preferably such that from about 0.1 to 1 part by weight of the second package is employed per part of the first package. For use, the two packages are merely mixed together in suitable fashion at the point of use. Component (vi) is optionally mixed into the polymer composition just prior to applying to a porous web. Other suitable silicone polymer compositions, without additives, are disclosed in the following U.S. patents:

U.S. Pat. No. 4,032,502 provide compositions containing a linear polydiorganosiloxane having two siloxane bonded vinyl groups per molecule, organosiloxane that is soluble in such linear polydiorganosiloxane and comprised of a mixture of a polyorganosiloxane and a polydiorganosiloxane, platinum-containing catalyst, a platinum catalyst inhibitor, and a reinforcing silica filler whose surface has been treated with an organosilicone compound.

U.S. Pat. No. 4,108,825 discloses a composition comprising a triorganosiloxy end-blocked polydiorganosiloxane, an organohydrogensiloxane having an average of at least 2.1 silicon-bonded hydrogen atoms per molecule, a reinforcing silica filler having a surface treated with an organosilicone compound, a platinum catalyst, and ceric hydrate. Such silicone polymer composition is desirable when a web is being prepared which has flame retardant properties.

U.S. Pat. No. 4,162,243 discloses a silicone composition of 100 parts by weight triorganosiloxy end-blocked polydimethylsiloxane, reinforcing amorphous silica that is surface treated with organosiloxane groups, organchydrogensiloxane, and platinum catalyst.

U.S. Pat. No. 4,250,075 discloses a liquid silicone polymer composition that comprises vinyldiorganosiloxy end-blocked polydiorganosiloxane, polyorganohydrogensiloxane, platinum catalyst, platinum catalyst inhibitor, and carbonaceous particles. Such a silicone polymer composition is useful when a web of this invention is being prepared that has electrically conductive properties.

U.S. Pat. No. 4,427,801 discloses a curable organopolysiloxane of liquid triorganosiloxy end-blocked polydiorganosiloxane wherein the triorganosiloxy groups are vinyl dimethylsiloxy or vinylmethylphenylsiloxy, finely divided amorphous silica particles treated with mixed trimethylsiloxy groups and vinyl-containing siloxy groups, organopolysiloxane resin containing vinyl groups, organohydrogensiloxane, and a platinum containing catalyst.

U.S. Pat. No. 4,500,659 discloses a silicone composition of liquid triorganosiloxy end-blocked polydimethylsiloxane wherein the triorganosiloxy units are dimethylvinylsiloxy or methylphenylvinylsiloxy, a reinforcing filler whose surface has been treated with a liquid hydroxyl end-blocked polyorganosiloxane which is fluorine-substituted, a liquid methylhydrogensiloxane, and a platinum-containing catalyst.

U.S. Pat. No. 4,585,830 discloses an organosiloxane composition of a triorganosiloxy end-blocked polydiorganosiloxane containing at least two vinyl radicals per molecule, an organohydrogensiloxane containing at least two silicone-bonded hydrogen atoms per molecule, a platinum-containing hydrosilation catalyst, optionally a catalyst inhibitor, a finely divided silica filler, and a silica treating agent which is at least partially immiscible with said polydiorganosiloxane.

U.S. Pat. No. 4,753,978 discloses an organosiloxane composition of a first diorganovinylsiloxy terminated polydiorganosiloxane exhibiting a specified viscosity and having no ethylenically unsaturated hydrocarbon radicals bonded to non-terminal silicon atoms, a second diorganovinylsiloxy terminated polydiorganosiloxane that is miscible with the first polydiorganosiloxane and contains a vinyl radical, an organohydrogensiloxane, a platinum hydrosilation catalyst, and a treated reinforcing silica filler.

U.S. Pat. No. 4,785,047 discloses silicone elastomers having a mixture of a liquid polydiorganosiloxane containing at least two vinyl or other ethylenically unsaturated radicals per molecule and a finely divided silica filler treated with a hexaorganodisilazane which mixture is then compounded with additional hexaorganodisiloxane.

U.S. Pat. No. 4,329,274 discloses viscous liquid silicone polymer compositions that are believed to be suitable and which are comprised of vinyl containing diorganopolysiloxane (corresponding to component B), silicon hydride siloxane (corresponding to component A) and an effective amount of a catalyst which is a halogenated tetrameric platinum complex.

U.S. Pat. No. 4,442,060 discloses a mixture of 100 parts by weight of a viscous diorganopolysiloxane oil, 10 to 75 parts by weight of finely divided reinforcing silica, 1 to 20 parts by weight of a structuring inhibitor, and 0.1 to 4 parts by weight of 2,4-dichlorobenzoyl peroxide controlled cross-linking agent.

Silicone resin compositions shown in Table I below have all been used in the practice of this invention. Such compositions of Table I are believed to involve formulations that are of the type hereinabove characterized.

TABLE I

Illustrative Starting Silicone Polymer Compositions

| Manufacturer | Trade Designation | Components[1] |
|---|---|---|
| Mobay | Silopren ® LSR 2530 | Vinyl-terminated polydimethyl/siloxane with fumed silica, methyl hydrogen |
| Mobay | Silopren ® LSR 2540/01 | |
| Dow Corning | Silastic ® 595 LSR | polysiloxane |
| General Electric | SLE 5100 | polysiloxane |
| General Electric | 6108 | |
| General Electric | 5110 | |
| Dow Corning | 2103 | |
| General Electric | SLE 5106 | siloxane resin solution |
| General Electric | SLE 5300 | polysiloxane |
| General Electric | SLE 5500 | polysiloxane |
| Shin-Etsu | KE1917 | |
| Shin-Etsu | DI 1940-30 | |
| SWS Silicones Corporation | Liquid Rubber BC-10 | silicone fluid with silicone dioxide filler and curing agents. |

[1]Identified components do not represent complete composition of the individual products shown.

When a polymer composition of a silicone polymer and a benzophenone is pressured into a porous web as taught herein, protection of an organic web against ultraviolet radiation is improved, and the degradation effects associated with ultraviolet light exposure are inhibited, as may be expected from prior art teachings concerning the behavior of benzophenones.

Ultra-violet-absorbing agents contemplated for use in the practice of the present invention include uvA absorbers such as benzophenone-8-methyl anthranilate; benzophenone-4; benzophenone-3; 2, 4-dihydroxy-benzophenone; uvB absorbers such as p-aminobenzoic acid (PABA); pentyl dimethyl PABA; cinoxate; DEA p-methoxycinnamate; digalloyl trioleate; ethyl dihydroxypropyl PABA; octocrylene, octyl methoxycinnamate, otcyl salicylate, glyceryl PABA; homosalate; lawsone plus dihydroxyacetone; octyl dimethyl PABA; 2-phenylbenzimidazole-5-sulfonic acid; TEA salicylate; sulfomethyl benzylidene bornanone; urocanic acid and its esters, and physical barriers such as red petrolatum and titanium dioxide.

To prepare a silicone polymer composition which incorporates a benzophenone, one preferably admixes the benzophenone with the silicone polymer composition at the time of use. The benzophenone component can be regarded as, or identified herein for convenience as the modifier component (vi). On the same parts by weight basis above used, a composition of this invention contains from about 0.1 to about 15 parts of component (vi), although the preferred amount is from about 0.3 to about 10 parts of component (vi) and smaller amounts can be used, if desired, without departing from the spirit and scope of the invention.

One class of derivitized benzophenones useful in the practice of this invention is characterized by the generic formula:

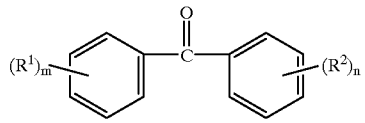

where $R^1$ and $R^2$ are each selected from the group consisting of hydroxyl, lower alkoxy, and hydrogen, and n and m are each an integer of 1 or 2. Examples of substituted benzophenones of the above formula include the substances shown below.

TABLE II

Substituted Benzophenones

| ID. No. | Name | Commercially available under specified trademark from BASF |
|---|---|---|
| 1 | 2,4,dihydroxybenzophenone | "Uvinul" 400[1] |
| 2 | 2-hydroxy-4-methoxy-benzophenone | "Uvinul" M-40 |
| 3 | 2,2',4,4'-tetrahydroxybenzophenone | "Uvinul" D-50 |
| 4 | 2,2'-dihydroxy 4,4'-dimethoxy benzophenone | "Uvinul" D-49 |
| 5 | mixed tetra-substituted benzophenones | "Uvinul" 49D |

[1]Presently most desired substituted benzophenone

Another class of derivitized benzophenones useful in the practice of this invention is characterized by the generic formula:

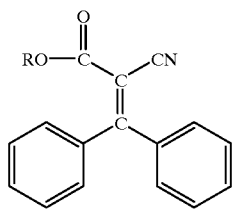
(3)

where:

$R^3$ is a lower alkyl radical.

An example of a substituted benzophenone of formula (3) is: 2-ethylhexyl-2-cyano3,3-diphenylacrylate (available from ASF under the trademark "Uvinul N-539").

In the preceding formulas (3) and (4), the term "lower" has reference to a radical containing less than about 8 carbon atoms. The contact angle exhibited by a silicone composition used in this invention varies with the particular web which is to be saturated therewith. However, the contact angle of water is generally lower for the non-treated side than the treated side. A combination of the processed web, the silicone polymer and the fluorochemical generally produces higher water contact angles than webs treated only with fluorochemicals. The performance of a polymer composition may be determined by the nature of a previously applied saturant such as a fluorochemical. Suitable starting compositions include 100% liquid curable silicone rubber compositions, such as SLE5600 A/B from General Electric, Mobay LSR 2580A/B, Dow Corning Silastic® 595 LSR and Silastic® 590 which when formulated with substituted benzophenone as taught herein will form a contact angle of much greater than 70 degrees, and typically of 90+ degrees, with typical porous webs (such as fabrics) that have a residue of fluorochemical upon (and within) the web from a prior saturation.

The polymer composition used in the practice of this invention can also carry additives into the three-dimensional structure of the web during the pressured application. Further, it is preferable, that any additives and/or modifiers be bound into the cured composition permanently as located in the three-dimensional structure of the web. Particularly in the case of fabrics, this desirably positions the additives and/or modifiers mainly on surface portions of the encapsulated yarns and fibers in positions where they typically are beneficially located and maintained, or on the surfaces of the internal layer, or on the surfaces of the web, or some combination thereof. When necessary, the polymer composition, the web or fabric used, and the particular additive and/or modifier compounds can be altered to create specific functional properties such as adhesiveness, antimicrobial activity, blood repellency, conductivity, fire resistance, flexibility, good hand, stain resistance, ultraviolet absorption capabilities, and other functions described by this invention.

Silicone polymers, when compounded with additives and/or modifiers, produce desirable properties. For example, a fine particle silica is added to silicone polymer as a filler or reinforcing agent to increase the hardness and reduce the stickiness. Carbon black is added when electrical conductivity is required. Red iron oxide improves heat resistance. Zinc oxide is used for heat conductivity. Aluminum hydrate is added for extra electrical track resistance. Various pigments are used for coloring. Such solid additives and/or modifiers can be added by mixing with silicone polymer at a certain ratio. Mixing of the silicone polymer is usually performed by a mixer, or the like. Care should be taken to add the additive (and/or modifier) powders slowly enough to prevent balls of high additive and low silicone content from forming and floating on top of the silicone polymer which leads to poor dispersion. Poor dispersion will result in an uneven distribution of the additive and/or modifier on and within the web. If much additive and/or modifier is being added, several separate additions and cross blending between them will assure good dispersion. The sequence of addition is also important. For instance, when extending fillers are added, they should be added after the reinforcing fillers. Color, when used, may be added at this stage. The catalyst is added at the final stage or is part of the co-blended polymer composition. Care should be taken to be sure the compound temperature is cool enough to prevent unexpected curing of the silicone polymer.

Liquid additives and/or modifiers can be added by directly mixing with silicone polymer or finely dispersing in the silicone polymer. Additives and/or modifiers can also be added in a homogeneous form such as dissolving in suitable organic solvents or water, or in a heterogeneous form such as latex. For example, hydrophobic polyurethanes or fluorocarbon polymers can be dispersed in water by addition of emulsifiers or surfactants in a emulsion form or latex.

A wide variety of additives, agents, or modifiers, herein used interchangeably, can be used in accordance with the practice of this invention to produce porous webs that retain the functional properties of the agents incorporated within the web. It is impossible to list in certainty all of the agents and modifiers that can be used in accordance with the practice of the present invention. Many of the additives used in the plastics industry are described in handbooks and can be used in accordance with the practice of this invention. Two such handbooks are *Plastics Additives: An Industrial Guide*, by Ernest W. Flick (Noyes Publications 1986), and *Chemical Additives For The Plastics Industry: Properties, Applications, Toxicologies*, by the Radian Corporation (Noyes Data Corp. 1987), herein incorporated by reference. The charts below list (1) additives known to work in accordance with the practice of this invention, (2) additives that are substantially similar in physical and/or chemical properties to the additives that are known to work in accordance with the practice of this invention, and (3) additives that were unknown in the art as of the printing of the above referenced handbooks. Some of these agents are discussed in greater detail in subsequent sections.

Adhesive Agents

Epoxy-resin
Co-oligomer
Phenolic resins
Polyurea resins
Polyolefins
Polyamides
Polysiloxanes
Polysulfides
Polyvinyl esters
Neoprene
Polyurethanes
Polyacetal resin, with one or more members selected from the group consisting of isocyanate and isothiocyanate compounds.

Anti-Static Agents

Fatty acid esters and their derivatives
Long-chain amines
Amides
Quaternary ammonium salts
Polyoxyethylene derivatives
Polyhydric alcohols and their derivatives
1,2-epoxides such as 1,2-epoxyhexane, 1,2-epoxyoctane, 1,2-epoxynonane, 1,2-epoxydecane, 1,2-epoxydodecane, 7,8-epoxyoctadecane, 9,10-epoxyoctadecane, 5,6-epoxydodecane, 7,8-epoxyoctadecane, 2,3-epoxydodecane, 5,6-epoxydodecane, 7,8-epoxyoctadecane, 9,10-epoxyoctadecane, 10,11-epoxyeicosane.
Epoxides reacted under acid or alkaline catalyst conditions with ethylene glycols or 1,2-propylene glycols. Example catalysts are BF etherate, sulfuric acid, sodium methylate, and lithium methylate. Preferable ethylene or propylene glycols are mono-, di, tri and tetra.

Biocidal Agents

Halogens and halogen based compounds such as iodine, chloroazodin, chlorinated cyanuric acid derivatives, and chloramine derivatives.
Antibiotics
Anti-virals such as zidovudine
Nonoxynol-9
Phenols and phenolic compounds such as o-phenylphenol, o-benzyl-p-chlorophenol, p-tert-amylphenol, bisphenols such as hexachlorophene, dichlorophene, methylene-bis(4-chlorophenol), fentichlor, and trichlosan.
Quarternary ammonium salts such as cetrimide, benzalkonium chloride, cetylpyridinium chloride, laurolinium acetate, dequalinium chloride, hedaquinium chloride, polyquaternium 1.
Zinc oxide, Z-N-octyl-4-isothiazole-3-one
Phenyl mercuric acetate
Skin disinfectants such as alcohols, mercurials, silver compounds, neomycin
Water disinfectants such as chlorine and sodium hypochlorite
Air disinfectants such as propylene glycol, lactic acid, glycolic acid, and levulinic acid
Gaseous disinfectants such as ethylene oxide, β-propiolactone, and formaldehyde
Clothing disinfectants such as neomycin Methyl dimethyl propoxylene ammonium chloride
Polyiodide material like Pentaiodid
Acid salts derived from hydrochloric, methane sulfonic, ethanesulfonic, isoethionic, lactic, and citric acids.
Trichlorocarbon Blood Repellents Antimicrobial or biocidal agents
Monoaldehyde
Iodophors such as povidone-iodine, polyvinyl pyrrolidone (PVP) or povidone USP, butyl cellosolve albumin-povidone-iodine complex
Polyethylene glycol mono (nonylphenyl) ether
Diethyl ether
Phenol resin
Urea resin
Urethane modified epoxy resin
Organosilicon quaternary ammonium salts Dyes and Pigments Azoic dyes
Cationic Dyes
Sulfur dyes
Nigrosine
Carbon black Electrical Conductive Agents Metal particles or fillers
Zinc oxide
Stannic oxide
Indium oxide
Tungsten and tungsten carbide
Carbon black
Graphite and metal coated graphite
Conductive polymers
Silver, nickel, copper, aluminum, gold
Rhodium
Ruthenium
Molybdenum
Iridium
Platinum
Palladium Electromagnetic Shielding Agents Hypophosphorous
Carbon-phenol resin compound Fillers Carbon
Molecular sieves
Fumed silica
Colloidal silica Flame Retardant Agents Aluminum hydroxide
Borax
Tetrakis (hydroxymethyl)
Phosphonium chloride
Potassium hexafluoro zirconate
Potassium hexafluoro titanate
Polyamide
Polyimide
Poly-parabanic acid
Polyether sulfone, polyether ether keton, polyetherimide
Fluoroplastic resin films
Plyphenylene sulfide
Magnesium hydroxide
Silicone treated magnesium oxide
Polybenzimidazole
Non-flame durable fibers with flame durable fibers of metal such as stainless steel, copper, nickel
Carbon or carbonizable compositions
Kevlar ™
Nomex ™
Retardant powder fillers such as alumina trihydrate
Kaolin, gypsum and hydrated clay incorporated with polydimethylsiloxanes
Polypropylene, polybutylene
Metal carboxylic acid salts containing at least 6 carbon atoms.
Calcium, barium and strontium compounds
Carboxylic acid salts: calcium stearate, barium stearate and strontium stearate, stearates, isostearates, oleates, palmitates, myristates, laurates, undecylenates, 2-ethylhexanoates, hexanoates
Salts of the following acids may be suitable: sulfinic, sulfonic, aromatic sulfenic, sulfamic, phosphinic and phosphoric acids
Polyolefins such as low density polyethylene and high density polyethylene
Polypropylene, polybutylene
Copolymers such as polystyrene, polycarbonates
Polyesters, polyamides, polycaprolactams
Ionomers, polyurethanes, co- & ter-polymers
Acrylonitrile, butadiene, styrene, acrylic polymers, acetal resins, ethylene-vinyl acetate
Polymethylpentene
Polyphenylene oxide, polyphenylene oxide-polystyrene blends or copolymers with optinal organic halides such as decabromodiphenyl oxide, dechlorane plus a chlorinated alicyclic hydrocarbon, and aluminum trihydrate Flexibility Inducing Agents Diglycidyl ether of linoleic acid dimer
Diglycidyl ether of polyethylene glycol
Dizlycidyl ether of polypropylene glycol
Dizlycidyl ether of alkylene oxide adduct of bisphenol A
Urethane prepolymer
Urethane modified epoxy resin
Polycarboxyl compounds
Polycaprolactone
Phenoxy resin Flattening Agents Amorphous Silica 1–2% by total resin weight, such as OK 412, produced by DeGussa, Inc. (Frankfurt, Germany), available through its pigment division in Teterboro, NJ.
Silica
Micronized polyethylene Grease Resistant Agents Carboxymethylcellulose, methylcellulose, methylethylcellulose, hydroxypropylmethylcellulose, hydroxypropylcellulose Hand Altering Agents Protein structures made to imitate some borrowed property on or near the surface of the polymers.
Natural and synthetic beta-pleated sheet proteins
Hydrolized silk such as "Crosilk," a commercially hydrolized silk protein (Croda, Inc. New York, NY). Crosilk is a 10,000 molecular weight protein made by hydrolizing silk, and is comprised of 17 different amino acid segments, ranging in percent by weight of 0.1% to 20.3%.
Polyolefin fiber or fabric Humidity Controlling Agents Solid copper salts, preferably organic copper salts such as copper formate, copper acetate, copper oxalate and others.

Ion-Exchange Agents

Duolite C255H ™ by Diamond Shamrock
Ammonium salts
Chloride
Compounds and materials exhibiting acidic or basic functionality
Nitrate
Zeolite beta, zeolite chabazite (low calcium)

Light Fastness-Inducing Agents

Ink dyes
Cationic dyes
Acid dyes
Monosulfonic acid, disulfonic acid, sulfonic acid-carboxylic acid Light-Reflective Agents Titanium oxide
Zinc oxide Mildew Resistant Agents Thiazolylbenzimidazole
Zinc phosphite
Derivatives of phenol
Derivatives of benzothiazole -continued Organosilicon quaternary ammonium salt
Processing Agents Crosslinking inhibitors
Rheological agents
Hydrophilic polymers
Polyvinyl alcohol
Proteins Silk protein
Fibroin
Collagen
Radio Frequency Shielding Agents Photoresistive films made of polyamide or SOG (Spin On Glass)
Magnetic films
Piezoelectric
Photoresistive films as a switchable EMI barrier
Rot Resistant Agents Zinc chloride, chromated zinc chloride
Stain Resistant Agents A mixture of phenyl vinyl ether/maleic diacid copolymer and Z-(4-hydroxy-methyl-phenoxy)-ethyl vinyl ether/maleic diacid copolymer and a copolymer obtained by the reaction of phenyl vinyl ether 2-(4-hydroxymethyl-phenoxy)-ethyl vinyl ether and maleic anhydride
Erional ™ NBS, Intratex N ™
Mesitol, FX-369, CB-130, Nylofixan P
Therapeutic Agents Antibiotics
Chemotherapeutic compounds
Hormones
Analgesics such as aspirin
Vitamins
Spermacides such as ricinleic acid, p-diisobutylphenoxypolyethoxyethanol, boric acid, and nonoxynol-9.
Drugs
Growth Factors
Molecular sieves or other enclosed forms containing all of the above.
Thermal Conductive Agents Aluminum particles such as aluminum nitride and alumina
Fillers such as silver
Graphite
Silicon carbide
Boron nitride
Diamond dust
Synthetic resin
Ultraviolet-Absorbing Agents Benzophenone and its derivatives
Aryl group-substituted benzotriazole compound
Cinnamic acid esters
Benzoxazale
4-thiazolidone compounds
Titanium dioxide
Zinc oxide
Water Repellent Agents Fluoroalkylsilane
Alkylsilane
Dimethylpolysiloxane
Flourine-type water repellent agent (Asahi Guard AG710)
Silazene compound, e.g., $(CH_3)_3$ SiNH-Si$(CH_3)_3(6)$
Stearic acid salts
Zirconium compounds
Flurosilicon type KP-801
Epoxy group-containing organosiloxanes
Polysiloxanes containing fluorine atoms
Perfluoroakyl-silicone-KP801
Dimethylamino-silicone
Wax Some additives and/or modifiers may or may not be combined with the thixotropic material prior to application to the porous substrate. These materials are applied to the surface of the porous substrate by depositing or metering, or by other like means.

Other additives and/or modifiers suitable for use in the practice of the present invention include compounds that contain reactive sites, compounds that facilitate the controlled release of agents into the surrounding environment, catalysts, compounds that promote adhesion between the treating materials and the substrate, and compounds that alter the surface chemistry of articles produced from the treated substrates.

Reactive sites contemplated in the practice of the present invention include such functional groups as hydroxyl, carboxyl, carboxylic acid, amine groups, and the like, that promote physical and/or chemical interaction with other materials and compounds. For example, the modifier may be an enzyme or metal that catalyzes a specific reaction. Alternatively, the modifier may bind an agent. The phrase "capacity to bind," as used herein, refers to binding by both covalent and non-covalent means. Polyurethane is an example of a modifier with reactive sites that specifically bind iodine, the agent. A protein is an example of a modifier with reactive sites that specifically bind an antibody, the agent. The resulting articles are useful, for example, where iodine release is desirable (e.g., as a disinfectant), due to the tendency of iodine to sublime under ambient conditions.

The modifier or agent may also be a biologically active or "bioactive molecule" such as an enzyme, antibody, antigen, or other binding protein such as biotin or avidin. For example, the modifier may be an antibody and the agent, a target protein, and the like. Or, the modifier may be a protein, and the agent, a target antibody. Such embodiments are particularly useful to the field of medical diagnostics.

Alternatively, the modifier may be capable of binding any proteinaceous material regardless of its bioactivity, such as polypeptides, enzymes or their active sites, as well as antibodies or antibody fragments. These embodiments, as contemplated in the practice of the present invention, are applicable to both research- and industrial-scale purification methods.

Depending on the end use of the treated material, a variety of modifiers containing reactive sites can be used. For example, modifiers can be employed that bind agents that are airborne organic contaminants. The particular compound employed as the modifier will depend on the chemical functionality of the target agent and could readily be deduced by one of skill in the art.

Also contemplated by the present invention is the use of modifiers that are capable of promoting the release of an agent from the treated web. For example, where the agent is being released from a thixotropic material that is hydrolytic, the modifier may be a hygroscopic compound such as a salt that promotes the uptake of water. As water is drawn into the material, the thixotropic material degrades by hydrolysis, thus releasing the agent. Alternatively, the modifier may promote the release of an agent from the treated web by creating pores once the resulting article is placed in a particular environment. For example, a water-soluble hygroscopic salt can be used to induce pore formation in thixotropic materials when placed in a humid or aqueous environment. Thus, dissolution of the salt promotes the release of the agent from the treated substrate. Other such modifiers that promote the release of an agent from materials are known to those of skill in the art. Agents suitable for use in these embodiments include therapeutic agents, biologically active agents, pesticides, biocides, iodine, and the like.

Also contemplated for use in the practice of the present invention as the modifier component are hydrogels. Hydrogels are polymeric materials that are capable of absorbing relatively large quantities of water. Examples of hydrogel forming compounds include polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like.

Control of the pressurized application step can be provided at a number of areas since the shear process is sensitive to the viscosity of the polymer composition both at atmospheric pressure and at superatrnospheric pressure. The ambient temperature affecting the polymer as it is applied, and the pressure-induced temperature changes occurring during controlled placement of the polymer also play roles in viscosity and therefore the shear process. Of course, the chemical make-up of the polymer composition also plays a role in the shear process and assists in the formation of an internal layer and/or internal encapsulation of the fibers or structural elements of the web.

The amount of polymer utilized and the weight add-on thereof are again variable and dependent upon several things such as the treated web, the desired end use of the web, cost and the like. Web weight add-ons can be as little as about 1 to 5 weight percent up to about 200 weight percent of the untreated web. For producing breathable, water-repellent fabric webs of this invention, weight add-ons are preferably in the range of about 10 to about 100 weight percent of the weight of the untreated web.

The fluorochemical saturant composition may also contain a bonding agent. The bonding agent can facilitate the bonding of the water repellent chemical and/or the impregnate to the three-dimensional structure of the web within which it is saturated. Mobay Silopren™ bonding agent type LSR Z 3042 and Norsil 815 primer are representative compositions that can be used to facilitate bonding of the water repellent chemicals and/or impregnant to and within the web. Use of the bonding agents is not essential to the practice of this invention, but may improve bonding of the fluorochemical and/or the polymer composition to fibers.

The fluorochemical particularly, and also the bonding agents when used, are preferably affixed to the three-dimensional structure of the web prior to the controlled placement of polymer within the web. Complete affixing is not necessary for the fluorochemical. The fluorochemical will apparently facilitate the pressured application of a polymer composition even if the fluorochemical is not preliminarily fixed within or located within the web being treated. However, fixing, especially by sintering, appears to cause the water repellent chemicals to flow and to become better attached to the three-dimensional structure of the web. In this regard, a lesser amount of fluorochemical will remain in place better, and will better facilitate the subsequent pressured application of the polymer, if the sintering or insolubilizing step is performed prior to such a pressured application.

After fluorochemical saturation followed by controlled polymer placement and curing, a web may have a surface contact angle with the polymer of greater than about 70 degrees, and more typically greater than about 90 degrees. Web pressures can involve transverse force or pressure in the range of tens to thousands of pounds per square inch of web surface.

Similar to the functional qualifications achieved by the use of a fluorochemical in the preferred saturating pretreatment step, the polymer introduced by the pressured application step can be defined by its functional qualifications. For example, the silicone polymer produces a contact angle with a fluorochemical treated web of greater than about 70 degrees. The contact angle of a web with a fluorochemical will be within a range of about 90 degrees to about 180 degrees while the contact angle of a fluorochemically treated web with the silicone polymer will be within a range of about 70 degrees to about 180 degrees.

The contact angle exhibited by the silicone polymer can be, if desired, qualified against the particular web saturated with the particular fluorochemical saturant. The selection of a suitable silicone polymer composition may be determined by the nature of the previously applied fluorochemical saturant. The fluorochemical saturant and silicone polymer compositions are, however, not critical to the practice of this invention since wide respective compositional ranges may be involved. In particular, a substantially undiluted liquid silicon rubber which is available from suppliers, such as GE, Dow Corning, and Mobay-Bayer, will characteristically form a contact angle of much greater than about 70 degrees, and typically greater than about 90 degrees, with typical porous webs (such as fabrics) that have a residue of fluorochemical upon (and within) the web resulting from a prior saturation.

The polymer composition can carry additives into the three-dimensional structure of the web in the pressured application steps of the method of the invention. Further, the polymer composition, when cured, is capable of adhering to structural elements, fibers, yarns, and the like, and any additives dispersed therein. Thus, additives are positioned adjacent to or on surfaces of structural elements, yarns, fibers and the like, in a position where they can be beneficial.

The energy can also be used to drive additives and/or modifiers to various selected positions within the porous web. During this stage, the viscosity of the thixotropic material becomes low enough and the application thickness thin enough such that additives and/or modifiers are able to move with either the sufficient mechanical energy or wave induced energy. Depending on the affinity of the additive and/or modifier for the thixotropic impregnant material as compared to the substrate/impregnant and impregnant/air interfaces, the additive and/or modifier will migrate to a particular region within the web. This migration is referred to herein as "surface blooming." The extent and rate of migration can be controlled by controlling the viscosity and thickness of the impregnant and the mobility of the particular additive and/or modifier. Both characteristics depend on the amount of energy provided to the system. Due to the nature of the thixotropic material, the additives and/or modifiers can be fixed at any location along their migratory path. For example, the amount of energy directed at the impregnant and web is decreased as the additives and/or modifiers migrate into the target positions. As the viscosity of the thixotropic impregnant rises, the additives and/or modifiers become essentially locked in place. This cycling of energy may be repeated in this stage, as well as in Stages 4 and 5, discussed below, until the additives and/or modifiers are finally moved and fixed into the preselected position.

Surface blooming is a term describing both the migration and exact orientation of the additive and/or modifier on or near the surface of the polymer. There seems to be either such a thin layer of the polymer (mono layer) or an actual breaking of the surface structure of the polymer so as to allow the exposure of the additive and/or modifier. It can also be applied to a time dependent effect whereby over time and exposure to movement and ambient conditions, the additive and/or modifier becomes exposed, as with time released agents.

The phenomenon referred to as "surface blooming" is believed to be the result of several factors working in conjunction, some of which are described above. The alternating silicon and oxygen (siloxane) bonds create a flexible backbone, and rotation is fairly free about the Si—O axis, especially with small substituents, e.g., methyl, on the silicon atoms. Rotation is also free about the Si—C axis in methylsilicon compounds. As a result of the freedom of motion, the intermolecular distances between methylsiloxane chains are greater than between hydrocarbons. and intermolecular forces are smaller. Polydimethylsiloxane (PDMS) contains a very surface active group, —$CH_3$, whose activity is presented to best effect by the unique flexibility of the backbone. A more complete description of the surface characteristics of polydimethylsiloxanes is available in *The Surface Activity of Silicones: A Short Review*, Michael J. Owen, Ind. Eng. Chem. Prod. Res. Dev., v. 19, p97 (1980); and the *Encyclopedia of Polymer Science and Engineering 2d Ed.*, Wiley, N.Y., v. 15, Silicones (1985–90); all herein incorporated by reference.

Additional control over the positioning of additives and/or modifiers may be exerted during the curing process in Stage 8, discussed below. This control relates to another mechanism of additive and/or modifier movement during treatment as described in the discussion of Stage 8 below.

Energy sources contemplated for use in the practice of the present invention include subjecting the curable, thixotropic material and one or more modifiers to shearing conditions ("treating materials"). For example, the shearing conditions may be provided by passing the treating material and web in contact with one or more blades at a fixed orientation with respect to the blades. The blades may be either rigid or flexible to accommodate a greater variety of web materials. For example, a more rigid blade may be used if the web is soft and flexible. Similarly, a flexible blade may be used if the web is hard and rigid.

Alternatively, the energy may be provided by passing the treating materials and web through rollers at a controllable pressure. Other sources of energy contemplated for use in the practice of the present invention include thermal energy, ultrasonic energy, electron beam, microwave, and electromagnetic radiation.

Examples of additives that are dispersible in effective amounts in a viscous polymer composition typically at a concentration of about 0.1 to 20 weight percent (based on total composition weight) include ultraviolet absorbers, flame retardants, aluminum hydroxide, filling agents, blood repellents, flattening agents, optical reflective agents, hand altering agents, biocompatible proteins, hydrolyzed silk, and the like. Hydrolyzed silk is a texturing agent that imparts a substantially silky feel to a fabric treated in accordance with the method of the invention regardless of whether or not such treated web or fabric is itself silk.

Examples of other polymer dispersible agents include those affecting thermal conductivity, radiation reflectivity, electrical conductivity, and other properties. For example, if a metallic sheen and/or thermal or electrical conductivity or infrared background blending is desired, powdered metals may be dispersed therein.

The pressured application of the polymer is sensitive to the viscosity of the polymer composition. Temperature affects the polymer composition by reducing or altering its viscosity. Shear-induced temperature changes occurring during application or during subsequent shear processing of the polymer can affect viscosity. The chemical composition of the polymer also plays a role in the treating process and effects in the treatment of web structural elements (including fibers) and the regulation of the filling of interstices and open cell voids.

Various machines and procedures can be used for performing the process of the invention. Illustrative machines and processes of use which are suitable for use in the practice of this invention, are described in U.S. Pat. No. 5,876,792, filed Mar. 17, 1995 and hereby incorporated by reference. A preferred apparatus for carrying out the present invention is described below.

The apparatus employed in the present invention functions first to apply and preferably concurrently to shear thin and place a polymer composition, with one or more additives and/or modifiers optionally mixed in the composition, into a web under pressure. Such polymer composition is then reintroduced, distributed, and metered in a controlled manner in the web with the aid of transversely applied shearing force and compressive force such that the polymer composition becomes distributed in the web so that additives and/or modifiers are oriented on and within the (a) thin film encapsulation of the individual fibers and filaments, (b) the controlled placement of the internal coating, and (c) some combination of (a) and (b). During treatment, the web is longitudinally tensioned and the pressurized application and the subsequent shearing and compressive actions are successively accomplished in localized zones preferably extending generally laterally across the web (that is, generally perpendicularly to the direction of such longitudinal web tensioning) using transversely applied force exerted locally against surface portions of the web during each controlled placement and shearing operation. The web is conveniently and preferably, but not necessarily, moved longitudinally relative to such laterally extending web processing zones. In treating short lengths of a fabric, the blades may be moved relative to a stationary length of fabric. The pressurized application, shearing and compressing steps are preferably carried out successively or sequentially. Such zones are themselves preferably at stationary locations while the web is moved, but if desired, the web can be stationary while the zones are moved, or both. The result is that the polymer composition flows into the web and is distributed internally generally uniformly to a predeterminable and controllable extent.

Some additives and/or modifiers, due to their physical and chemical properties, cannot be incorporated on and/or within a web by pre-treating the web or by mixing the additives and/or modifiers into the polymer composition. Such additives and/or modifiers can be topically applied to the web after the pressured, shear thinning stage described above, but before curing. Once topically applied, the additives and/or modifiers are forced into the web by passing through the exit nip rolls. The additives and/or modifiers will adhere to the polymer composition that forms encapsulated fibers, an internal layer, or some combination of the above.

Figure 5:
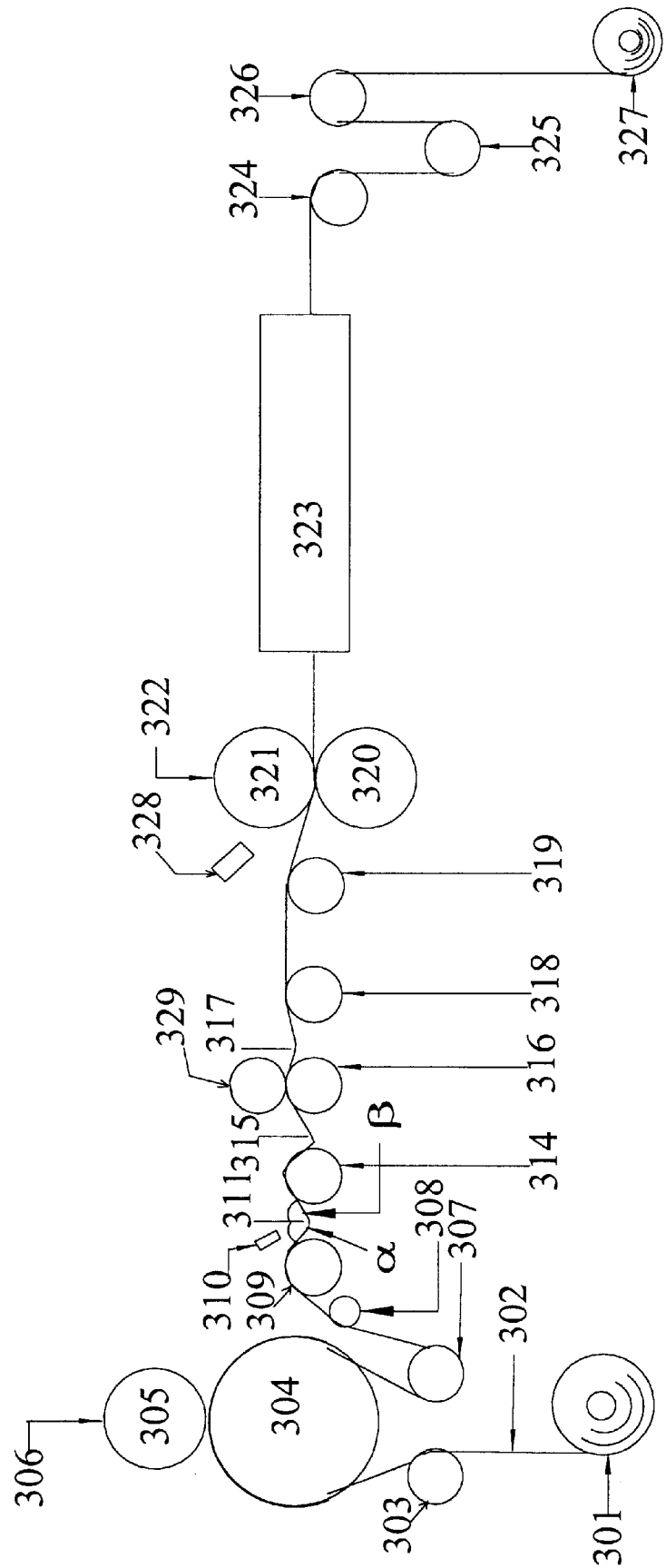
FIG. 5 illustrates diagrammatically a presently preferred embodiment of an apparatus suitable for use in the practice of the present invention.

FIG. 5 depicts a schematic, side elevational view of a preferred apparatus for practicing the methods of the present invention. In this embodiment a continuous web 302 is moved under tension along a web pathway from a supply roll 301 to a take-up roll 327.

The primary tension is a result of the differential rate between the driven entrance pull stand designated as 306 and the driven exit pull stand designated as 322, whereby the exit pull stand 322 is driven at a rate faster than the entrance pull stand 306. Other controllable factors which effect tension are the diameters of blade rolls 309, 314, 316, 318; the vertical depth of blades 311, 315, 317; the durometer of the entrance pull stand rolls 304, 305 and rubber roll 321 of the exit pull stand, and the friction as the web passes under the blades. Blade roll 316 can optionally be a nip roll, as shown with the top roll 329. This allows for the creation of multiple tension zones to help shear thin the polymer composition and place one or more additives and/or modifiers on or within the web.

Web 302 passes between the nip of the two rolls 304 and 305 of the entry pull stand 306. The entry nip is adjustable to produce a force of from about 100 lbs. to about 5 tons on the web, passing between the two rolls. The weight of top roll 305 provides an even distribution of force throughout the web width. Web 302 is flattened at this point and the interstitial spaces are reduced laterally and longitudinally. Bottom roll 304 has micro-positioning capability to provide for gap adjustment and alignment. The top roll 305 composition is chosen based on the durometer of a urethane or rubber roll.

Figure 4:
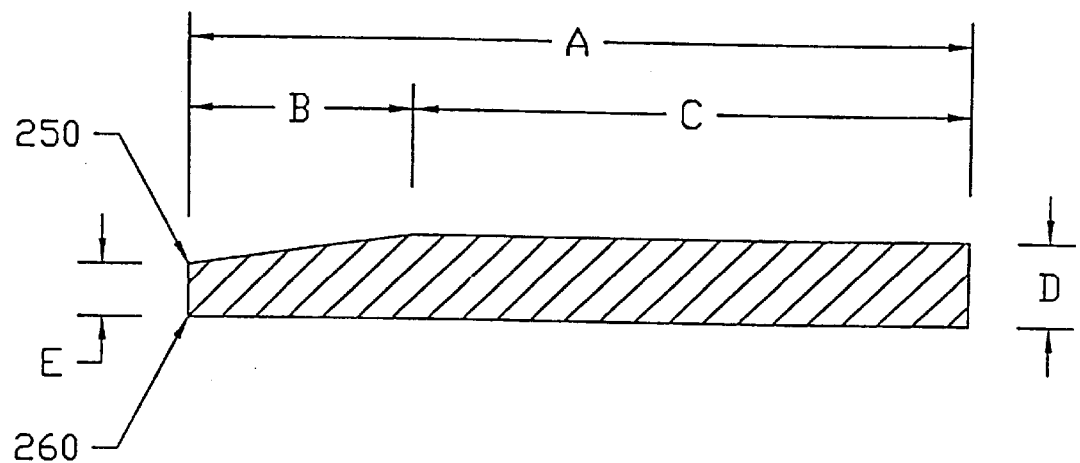
FIG. 4 illustrates diagrammatically one embodiment of a blade suitable for use in an apparatus used in the practice of the present invention.

Web 302 continues to move along past idler roll 308 and blade roll 309 and forms an entry angle a and an exit angle β with blade 311. Blade 311 is illustratively shown in FIG. 4. In FIG. 4, dimensions A, B, C, D, and E are typically and exemplarily illustrated as, respectively, about 3½ inches, about 1½ inches, about 2 inches, about ½ inch, and about 5/16 inch. The narrow edge is preferably milled to a tolerance of about 1/10,000 inch continuously along the edge surface of each blade which is typically and illustratively about 38 inches long. Each of the corners of the narrow edge is preferably and illustratively a hard (not beveled or ground) angular edge. Preferably, the combination of the leading edge condition and the two surfaces (the front and the bottom) that meet at the leading edge are RMS 8 or better in grind and/or polish. For purposes of the apparatus of FIG. 5, the blade in FIG. 4 has a leading edge 250 and a trailing edge 260. Entry angle α can be varied by adjusting: (a) the height and diameter of blade rolls 309 and 314, (b) the horizontal position of blade rolls 309 and 314, , (c) the angle of blade 311, and (d) the height of blade 311. Similarly, the entry and exit angles of blades 315 and 317, can be varied by adjusting the same devices surrounding each blade.

For illustrative purposes, increasing the height and diameter of blade roll 309 decreases entry angle α. Rotating blade 311 clockwise, with web 302 running left to right, increases entry angle α. Likewise, rotating blade 311 counter-clockwise, with web 302 running left to right, decreases entry angle α. Decreasing the distance between blade roll 309 and blade 311 decreases entry angle α. Increasing the downward depth of blade 311 into web 302 decreases entry angle α.

The angle of blades 311, 315, and 317 are completely changeable and fully rotational to 360°. The fully rotational axis provides an opportunity for more than one blade per rotational axis. Therefore, a second blade having a different thickness, bevel, shape, resonance, texture, or material can be mounted. Ideally the apparatus contains two or three blades per blade mount. The blade mounts are not shown.

The force or pressure of blade 311 applied against web 302 is determined by the vertical positioning of blade 311 in the blade mount. The greater the downward depth of blade 311, the greater the force or pressure. Blade pressure against the web is also accomplished through the tension of the web as described above.

The same line components that affect entry angle α, also affect exit angle β. Any changes in the height, diameter, or horizontal positioning of blade rolls 309 and 314, affects exit angle β. If the angle of blade 311 is rotated clockwise as described above, entry angle a increases, thus decreasing exit angle β.

As web 302 moves from left to right in FIG. 5, polymer, optionally mixed with one or more additives and/or modifiers, is deposited on web 302 with polymer applicator or dispersion means 310. Polymer applicator 310 can be a pump, a hose, or any available application device for applying polymer onto the surface of the web. Polymer applicator 310 is located directly in front of blade 311. The polymer is immediately shear thinned, placed into, and extracted from web 302 by the leading edge of blade 311, thus controlling the amount of polymer remaining in web 302. The bevel of blade 311 can effect entry angle α and the sharpness of the leading edge of blade 311. A sharper leading edge has a greater ability to push the weave or structural elements of web 302 longitudinally and traversely, increasing the size of the interstitial spaces. As the web passes the leading edge of blade 311, the interstitial spaces snap back or contract to their original size.

As web 302 moves from left to right in FIG. 5, the process of shear thinning and placing polymer into and extracting it out of web 302 is repeated at subsequent blades 315 and 317, thus controllably placing the polymer throughout web 302. Web 302 then passes over idler roll 319 and additives and/or modifiers are topically applied to web 302 by additive applicator or dispersion means 328. Additive applicator 328 can be a pump, or hose, or any application device for applying additives onto the surface of the web. Additive applicator 328 is located directly in front of the exit pull stand 322.

Web 302 then passes between driven exit pull stand 322 which consists of rolls 320 and 321. Pull roll 320 is a driven roll proportionally driven at a predetermined rate slower than entry roll 304. Pull roll 321 does not apply pressure so much as it achieves a high degree of surface area in which web 302 must come into contact with. The larger the surface area, the higher the degree of contact friction. Pull roll 321 can be adjusted to have sufficient downward force to eliminate any slippage between web 302 and pull roll 320.

After web 302 passes from exit stand 322, it then moves into an oven 323 for curing. Rolls 324, 325, and 326 provide a tension regulating means and also serve to provide a cooling pathway for web 302 as it emerges from oven 323 before passing onto take-up roll 327.

The cure temperature of oven 323 is thermostatically controlled to a predetermined temperature for web 302 and the polymers used. Machine runs of new webs are first tested with hand pulls to determine adhesion, cure temperature, potentials of performance values, drapability, aesthetics, etc. The effect on web 302 depends on the temperature of oven 323, dwell time and curing rate of the polymer. Web 302 may expand slightly from the heat.

Oven 323 functions to cure the polymer composition that is controllably placed into web 302. Oven 323 can be operated with gas or other energy sources. Furthermore, oven 323 could utilize radiant heat, induction heat, convection, microwave energy or other suitable means for effecting a cure. Oven 323 can extend from about 12 to 20 yards, with 15 yards long being convenient.

Curing temperatures from about 320° F. to about 500° F., applied for times of from about two minutes to about thirty seconds (depending on the temperature and the polymer composition) are desirable. If a curing accelerator is present in the polymer, curing temperatures can be dropped down to temperatures of about 265° F. or even lower (with times remaining in the range indicated).

The cure temperature of oven 323 and the source and type of cure energy, are controlled for a number of reasons. The cure temperature of oven 323 is controlled to achieve the desired crosslinked state; either partial or full. The source and type of energy can also affect the placement of the polymer and additives. In place of an oven, or in combination with an oven, a source of radiation can be employed (electron beams, ultraviolet light, or the like) to accomplish curing, if desired. For example, by using a high degree of specific infrared and some convection heat energy for cure, some additives can be staged to migrate and/or bloom to the polymer surfaces.

Oven cure dwell time is the duration of time the web is in oven 323. Oven cure dwell time is determined by the speed of the oven's conveyor and physical length of the oven. If the dwell time and temperature for a particular web is at maximum, then the oven conveyor speed would dictate the speed of the entire process line or the length of the oven would have to be extended in order to increase the dwell time to assure proper final curing of the web.

Take-up roll 327 is operated at approximately the same speed as supply roll 301. When the rotational speeds of take-up roll 327 are not synchronized with rotational speeds of supply roll 301, the tension roll combination of rolls 324, 325, and 326 can be used to reduce web slack.

Web speed is proportional to the variable speed of the motor which drives entrance pull stand 306 and exit pull stand 322. Web speed can effect the physics of the polymers as web 302 passes under blades 311, 315, and 317. Web transport speeds can vary widely; for example, from about two yards per minute to about ninety yards per minute.

FIG. 1 illustrates the phenomenon referred to herein as "thixotropic looping." This figure represents the viscosity changes of a polymer composition applied to a web by the apparatus shown in FIG. 5. For the purposes of demonstrating the general phenomenon, each blade is the same size and shape and each blade is positioned the same so that the shear rate at each blade is identical.

As the polymer composition comes in contact with the first blade, the shear stress reduces the viscosity of the polymer composition. Immediately after the first blade, the polymer begins to increase in viscosity, but never returns to its initial viscosity. As it comes in contact with the second blade, again the viscosity drops, but not as severe as with the first blade. Immediately after the second blade, the viscosity increases, but not to its initial viscosity. This phenomenon occurs again at the next blade and would continue at subsequent blades until the polymer reached its minimum viscosity.

A general process for making a porous web of this invention comprises the steps of: optionally pre-treating a flexible, porous web with a modifier by saturation methods known in the art; tensioning a flexible, porous web as above characterized; optionally mixing one or more additives and/or modifiers with a curable shear thinnable polymer composition; applying the mixed curable shear thinnable polymer composition, described above, to at least one web surface; and then moving over and against one surface of the tensioned web a uniformly applied localized shear force to: shear thin the optionally mixed polymer composition, uniformly place the composition within the web, at least partially individually encapsulate or envelop surface portions of at least some of said fibers through the web matrix or position said composition in a desired web internal region or some combination of both. Some additives and/or modifiers can then optionally be topically applied and pressed onto and into the web by the exit pull stand. Thereafter, the web is subjected to conditions sufficient to cure the composition in said web. Curing is accomplished by heat, by radiation, or both.

A presently preferred process for making a fluorochemical and silicone resin treated web having breathability, water resistance, rewashability, and one or more additives and/or modifiers, which is adapted for continuous operation comprises the successive steps of: impregnating the web with a fluorochemical, longitudinally tensioning the fluorochemical impregnated web while sequentially first applying to one surface thereof a curable silicone polymer composition with one or more additives and/or modifiers therein and concurrently applying a transversely exerted localized compressive force against said surface, and moving over said surface of the web substantially rigid shearing means which exerts transversely an applied, localized shear force against said surface to shear thin the polymer and wipe away exposed portions of silicone polymer composition on said surface, thereby forming an internal layer of silicone polymer and/or enveloping at least some of the fibers or passageways through the matrix, or both; optionally topically applying one or more additives and/or modifiers; and curing the silicone polymer composition in the web.

The additives and/or modifiers may also be selectively positioned during the final stage of the treatment process. When a diluent is incorporated into the polymer composition, the additives and/or modifiers may be moved by controlling the volatization of the diluent. As the diluent is driven to the air/polymer surface by heat, it carries the additives and/or modifiers with it to the surface. As the polymer composition cures, its viscosity increases thus fixing the additives and/or modifiers in position. Appropriate diluents include water and low molecular weight silicones and solvents such as aromatic solvents (e.g., toluene), low molecular weight ketones (e.g., acetone, methyl ethyl ketone, and the like. Positioning of the additive and/or modifier in this manner can be controlled by controlling among other variables, the amount of energy directed at the treating materials and substrate and the amount and type of diluent in the polymer composition. Positioning of additives and/or modifiers can also occur by the pressured application of additives and/or modifiers onto and into the web. Just prior to passing the treated web through the exit nip rolls, one or more additives and/or modifiers can be topically applied to the web, thereby forcing the additive(s) and/or modifier(s) onto and into one or more surfaces of the web. The additive and/or modifier can adhere to the web and/or the polymer composition in the web. Preferably the additive (s) and/or modifier(s) adheres to the polymer composition that encapsulates the individual fibers or filaments, that forms an internal layer, that fills some of the interstitial spaces of the web, or that produces some combination of the foregoing.

The following text concerns the theory of the invention as it is now understood; however, there is no intent herein to be bound by such theory.

The presently preferred polymer composition used in the treatment of webs by this invention is a non-Newtonian liquid exhibiting thixotropic, pseudoplastic behavior. Such a liquid is temporarily lowered in viscosity by high pressure shear forces.

One aspect of the invention is a recognition that when high forces or sufficient energy are applied to curable polymer compositions, the viscosities of these materials can be greatly reduced. When the viscosity is repeatedly reduced, the result is one of thixotropically looping or massaging the viscosity rheology crosslink opportunities and overall orientation of one or more additives and/or modifiers on and/or within the (a) thin film encapsulation of the individual fibers and filaments, (b) the controlled placement of the internal coating, and (c) some combination of (a) and (b). Thixotropic looping is illustratively and qualitatively shown in FIG. 1, for an apparatus containing three blades. Conversely, when subjected to curing, the same liquid composition sets to a solid form which can have a consistency comparable to that of a hard elastomeric rubber. The internal and external rheological control of polymer materials achieved by the present invention is believed to be of an extreme level, even for thixotropies. When subjected to shear force, the polymer composition is shear thinned and can flow more readily, perhaps comparably, for illustrative purposes, to water.

The invention preferably employs a combination of: (i) mechanical pressure to shear thin and place a polymer composition into a porous web; (ii) an optional porous web pretreatment with a water repellent chemical, such as a fluorochemical, which is theorized to reduce the surface tension characteristics of the web and create a favorable surface contact angle between the polymer composition and the treated web which subsequently allows, under pressure and shear force exerted upon an applied polymer composition, the production and creation of an internal coating or layer which envelopes fibers or lines cell walls in a localized region within the web as a result of polymer flow in the web or which encapsulates the fibers within the web; and (iii) a polymer composition impregnant preferably having favorable rheological and viscosity properties which responds to such working pressures and forces, and is controllably placed into, and distributed in a web. This combination produces a web having the capability for a high degree of performance. This product is achieved through pressure controlled placement and applied shear forces brought to bear upon a web so as to cause controlled movement and flow of a polymer composition and one or more additives and/or modifiers into and through a web. Preferably, repeated compressive applications of pressure or successive applications of localized shear forces upon the polymer in the web are employed.

By the preferred use of such combination, a relationship is established between the respective surface tensions of the polymer and the web, creating a specific contact angle. The polymer responds to a water repellent fluorochemical pretreatment of the substrate so as to permit enhanced flow characteristics of the polymer into the web. However, the boundary or edge of the polymer is moved, preferably repeatedly, in response to applied suitable forces into the interior region of a porous web so as to cause thin films of the polymer to develop on the fiber surfaces and to be placed where desired in the web.

Thixotropic behavior is preferably built into a polymer used in the invention by either polymer selection or design or additive/filler design. For example, it now appears that thixotropic behavior can be accentuated by introducing into a polymer composition certain additives that are believed to impart enhanced thixotropy to the resulting composition. A lower viscosity at high shear rates (during application to a web) is believed to facilitate polymer flow and application to a web, whereas a polymer with high viscosity, or applied at a low shear rate (before and/or after application) actually may retard or prevent structural element (including fiber) envelopment or encapsulation.

Illustratively, the practice of this invention can be considered to occur in stages:

In stage 1, a silicone polymer composition impregnant is prepared. It can be purchased commercially and comes in typically two parts designated as A and B. For example, in a silicone polymer composition, as taught in U.S. Pat. No. 4,472,470, a base vinyl terminated polysiloxane is the A part, while a liquid organohydrogensiloxane controlled crosslinking agent is the B part. Certain remaining components, such as a resinous organopolysiloxane copolymer and a platinum catalyst may (or can) apparently initially be in either part A or part B.

Stage 2 can be considered to involve the mixing of such a product's parts with or without additives. Changes in viscosity can be obtained and measured based on applied shear rates and shear stresses. Such changes can be experienced by a polymer with or without additives. Up to a 99% reduction in viscosity of a liquid silicone polymer composition is believed to be obtainable by the shear forces involved in the shear thinning and forcing of a silicone polymer composition impregnant into a web and almost simultaneously extracting the correct amounts out. Thereafter, a very substantial increase in polymer viscosity is believed to be obtainable taking into account these same factors. Normally, the most significant factor is now believed to be the shear gradient that typically reduces the viscosity of the polymer below the starting or rest viscosity.

Stage 3 can be considered to be the pressure introduction stage. Up to a 99% reduction of the polymer viscosity is believed to be obtainable due to the applied shear forces, elapsed time, temperature, radiation and/or chemical changes. Thereafter, a significant increase or even more in the resulting polymer viscosity is believed to be obtainable. In this stage, partial curing of the polymer may take place. Most commonly, polymer viscosity is substantially decreased during the pressure controlled placement Stage 3 by the application of shear forces.

Stage 4 can be considered to be the first stage internal matrix dispersing and reintroduction with metering, and also recovery and recycle of excess polymer. Typically, within this Stage 4, the shear forces cause a substantial but temporary lowering of polymer viscosity, causing it to flow upon and into the three-dimensional structure of the web. The initial viscoelastic character of the polymer is typically theorized to be recovered almost immediately after shear forces are removed.

Stage 5 can be considered to be a second stage internal matrix dispersing and reintroduction with metering and also recovery and recycling of excess polymer. The variations in the viscosity of the polymer are equivalent to Stage 4. The viscosity of the polymer is again lowered causing it to flow within the web. Because of the application of repeated shear force induced reductions in viscosity, the thixotropic behavior of a polymer may not undergo complete recovery, following each application of shear force and the viscosity of the polymer may not revert to its original placement values. The polymer composition is believed to have the capacity to form enveloping internal coating in a predetermined region wherein the interstices or open cells are substantially completely filled within the three-dimensional matrix constituting a web during the time intervals that the is caused to flow under pressure in and about matrix components. In between these times, the polymer may recover substantially all of its initial high viscosity, although perhaps slightly less so with each repeated application of shearing pressure or force.

Stage 6 can be considered the optional application of additives and/or modifiers. Some additives and/or modifiers, due to their physical and chemical properties, cannot be incorporated on and within a web by pre-treating the web or by mixing the additives and/or modifiers into the polymer composition. Such additives and/or modifiers can be topically applied to the web after the pressured, shear thinning stage described above, but before curing. Once topically applied, the additives and/or modifiers are forced into the web by passing through the exit nip rolls. The additives and/or modifier can adhere to the polymer composition or to the individual fibers of the web. Preferably, the additives and/or modifiers will adhere to the polymer composition that fills the warp filled interstitial spaces, forms encapsulated fibers, an internal layer, or some combination of the above.

Stage 7 can be considered to be occurring just as curing is begun, and just as heat or other radiation is introduced.

Stage 8 can be considered to be occurring with regard to the exertion of control of curing. Typically, at least a partial curing (including controlled cross-linking and/or polymerizing) is obtained by relatively low temperatures applied for relatively short times. For example, when light cotton, nylon, or similar fabrics are being treated, temperatures under about 350°, applied for under about 10 seconds, result in partial curing.

In one embodiment of the present invention, the curable, thixotropic material plus additives and/or modifiers form a porous film having an average pore size in the range of 0 to 10 microns (although not zero microns). Porous films are produced by the addition of pore-forming agents to the thixotropic material. Examples of pore-forming agents include low molecular weight polymers and oligomers that can be subsequently washed from the treated substrate using appropriate solvents and co-solvents that are known by those skilled in the art.

In preferred embodiments of the present invention, sufficient energy is used to selectively position the additives and/or modifiers at specific locations within the porous web. As employed herein, the phrase "selectively positioned" refers to the localization of additive and/or modifier materials at desired regions within the porous web. "Selective positioning" is achieved by controlling a phenomenon unique to thin films known as "migratory surface bloom." Migratory surface bloom refers to the ability of an additive and/or modifier to migrate to the surface and assume its multi-dimensional conformation.

The phenomena referred to as "surface blooming" is believed to be the result of several factors working in conjunction, such as the size and shape of the additive(s) and/or modifier(s), the thickness of the thin film, and the characteristics of polydimethylsiloxanes. The alternating silicon and oxygen (siloxane) bonds create a flexible backbone, and rotation is fairly free about the Si—O axis, especially with small substituents, e.g., methyl, on the silicon atoms. Rotation is also free about the Si—C axis in methylsilicon compounds. As a result of the freedom of motion, the intermolecular distances between methylsiloxane chains are greater than between hydrocarbons. and intermolecular forces are smaller. Polydimethylsiloxane (PDMS) contains a very surface active group, —CH$_3$, whose activity is presented to best effect by the unique flexibility of the backbone. A more complete description of the surface characteristics of polydimethylsiloxanes is available in *The Surface Activity of Silicones: A Short Review*, Michael J. Owen, Ind. Eng. Chem. Prod. Res. Dev., v. 19, p97 (1980); and the *Encyclopedia of Polymer Science and Engineering*, v. 15, Silicones, (Wiley 1987); all incorporated herein by reference. In the present invention, the extent of surface bloom is controlled by controlling the amount of energy directed at the treating materials and web.

In one embodiment of the present invention, the additive and/or modifier is selectively positioned substantially on the application surface of the porous web. In another embodiment of the present invention, the additive and/or modifier is selectively positioned substantially on the surface opposing the application surface of the porous web. Alternatively, where the porous web is derived from discrete elements such as fibers that are encapsulated, the additive and/or modifier can be selectively positioned substantially within the encapsulated material.

Figure 2:
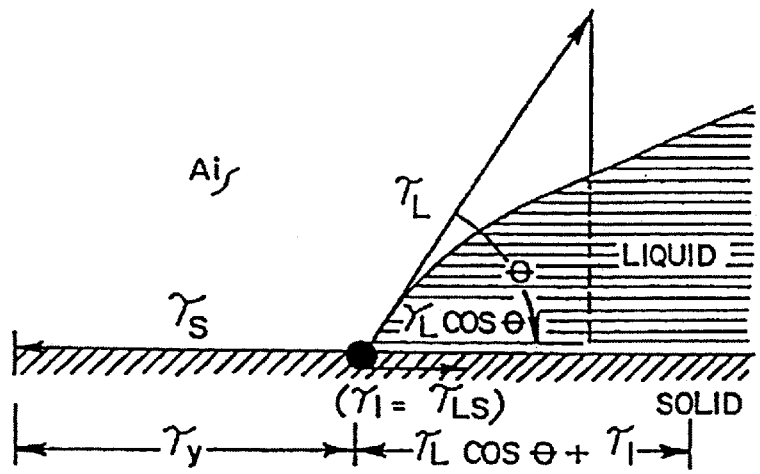
FIG. 2 is a schematic vector diagram illustrating surface tension forces.

FIG. 2 is a schematic vector diagram illustrating the surface tension forces acting at the vertex boundary line of a liquid contact angle on a planar solid surface. It illustrates how surface tension forces might be measured between a silicone polymer composition and a fiber of a web (or a fabric) as treated by the invention.

For the purposes of the present invention, the term "surface tension" can be considered to have reference to a single factor consisting of such variables as intermolecular, or secondary, bonding forces, such as permanent dipole forces, induced forces, dispersion or nonpolar van der Waals forces, and hydrogen bonding forces. The strong primary bonding forces at an interface due to a chemical reaction are theorized to be excluded from surface tension effects; however, it is noted that even a small degree of chemical reactivity can have a tremendous influence on wetting effects and behavior affected by surface tension.

The unique feature of poly-dimethylsiloxanes is their high surface activity. Pure poly-dimethylsiloxanes typically exhibit surface tension values of 21 dynes/cm, which is higher than only fluorocarbons. The prevailing explanation for this phenomenon is the dense packing of methyl groups at the surface of the poly-dimethylysiloxanes. The low surface tension of poly-dimethylsiloxanes gives them surface-active properties both in aqueous and organic solutions. This phenomenon is further described in David T. Floyd's article: *Organo-Modified Silicone Copolymers for Cosmetic Use*, Cosmetic and Pharmaceutical Applications of Polymers, p. 49–72, Plenum Press (New York 1991), herein incorporated by reference.

Surface tension is believed to induce wetting effects which can influence the behavior of a polymer composition impregnant relative to the formation of either a fiber enveloped layer therewith in a fibrous porous web, fiber encapsulation or both. For example, adhesion is theorized to be a wetting effect. Spontaneous adhesion always occurs for contact angles less than about 90°. However, for a combination of a rough surface and a contact angle over 90°, adhesion may or may not occur. In fact, roughness becomes antagonistic to adhesion, and adhesion becomes less probable as roughness increases.

Also, penetration is theorized to be a wetting effect. Spontaneous penetration occurs for contact angles less than about 90°, and does not occur for contact angles over about 90°. The roughness of a solid surface accentuates either the penetration or the repellency action, but has no influence on which type of wetting takes place.

Figure 3:
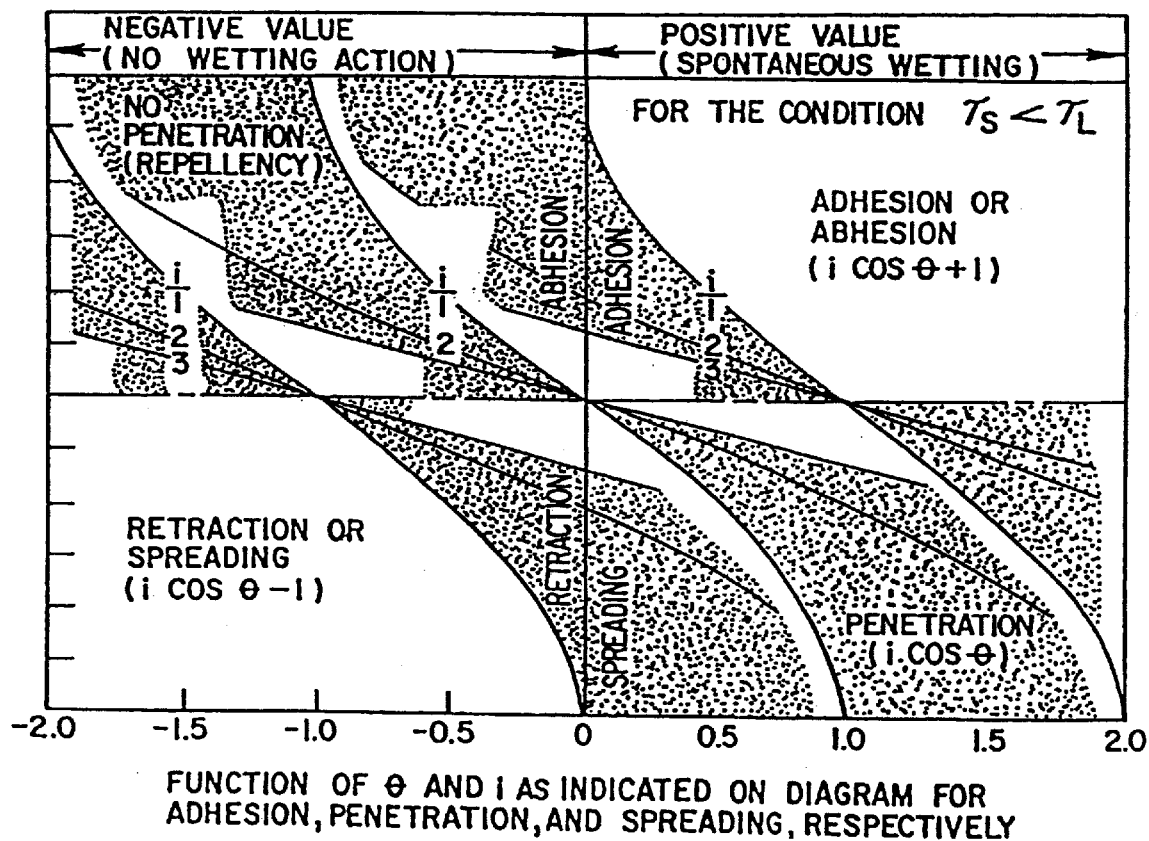
FIG. 3 is a graph relating contact angle over a smooth, solid surface.

In addition, spreading is theorized to be a wetting effect. Retraction occurs for contact angles over 90° or over planar surfaces for any contact angle. However, spontaneous spreading for contact angles less than 90°, especially for small contact angles, may be induced by surface roughness. FIG. 3 is a graph relating the contact angle over a smooth solid surface as a function of θ and i that apply respectively, to adhesion (I cos θ+1), penetration (i cos θ), and spreading (i cos θ−1).

Regions of adhesion versus abhesion, penetration versus repellency, and spreading versus retraction are shown by shaded areas. FIG. 3 illustrates what is theorized to be the relationship of a silicone polymer composition to silicone polymer composition solids in a treated web as regards such factors as adhesion, penetration, spreading, and retraction.

For purposes of this invention, the term "wetting" is used to designate such processes as adhesion, penetration, spreading, and cohesion. If wetting transpires as a spontaneous process, then adhesion and penetration are assured when the solid surface tension exceeds the liquid surface tension. Surface roughness promotes these spontaneous wetting actions. On the other hand, no such generalizations can be made when the solid surface tension is less than the liquid surface tension.

Surface tension is measured by S.T.L. units for liquid and by S.T.S. units for solids; both units are dyns/centimeter. When S.T.S. is less than S.T.L., then wetting is less ubiquitous and prediction of wetting behavior is more difficult. However, by taking advantage of the liquid/solid contact angle that forms when a liquid retracts over a solid, it is possible to calculate with reasonable accuracy the wetting behavior that can be expected. The reduction in liquid surface area can be computed in terms of the contact angle that the liquid makes with the solid surface. Contact angles are always measured in the liquid phase There is a point of equilibrium where the surface tension forces become balanced.

By measuring the contact angle of a liquid on a solid, the wetting behavior of the liquid polymer composition can be measured.

The present invention also includes a web comprising a web that has been treated with a curable thixotropic polymer composition, the web being adapted to be substantially impermeable to liquids, permeable to gases; and selectively impermeable or permeable to particles. The process of making the web selectively impermeable or permeable to particles or molecules is disclosed in copending U.S. patent application Ser. No. 08/487,004, filed on Jun. 7, 1995 which is incorporated herein by reference.

Products that can be manufactured from breathable barrier webs according to the present invention include, but are not limited to, foul weather garments, surgical gowns, protective webbing material that can be worn over hospital gowns, patient gowns, surgical scrub suits, sterilization wrappers (CSR wrap), cover gowns including protective webbing material, isolation gowns, hamper bags, jump suit, surgical masks, work aprons, surgical drapes laboratory coats, wound dressings, absorbent garments including, but not limited to, diapers, incontinent briefs, training pants, head bands, wrist bands, socks, underpants and the like.

Garments that can utilize barrier webs according to the present invention are described, for example, in U.S. Pat. No. 4,991,232 (hospital gown), U.S. Pat. No. 5,368,584 (disposable diaper and the like), U.S. Pat. No. 5,304,161 (incontinent pad and diaper), U.S. Pat. No. 5,318,554 (incontinent diaper), U.S. Pat. No. 5,342,335, (disposable absorbent products) U.S. Pat. No. 5,318,554 (absorbent articles), U.S. Pat. No. 5,304,161 (multilayer absorbent article), U.S. Pat. No. 5,290,269 (fabric for hygienic product), U.S. Pat. No. 5,147,345 (high efficiency diaper) U.S. Pat. No. 5,019,062 (bicomponent material for diapers), U.S. Pat. No. 4,828,556 (breathable barrier for incontinent garments) U.S. Pat. No. 4,758,239 (breathable barrier) U.S. Pat. No. 4,578,072 (leak resistant diaper) U.S. Pat. No. 4,560,380 (disposable therapy diaper) all of which are incorporated by reference.

Figure 7:
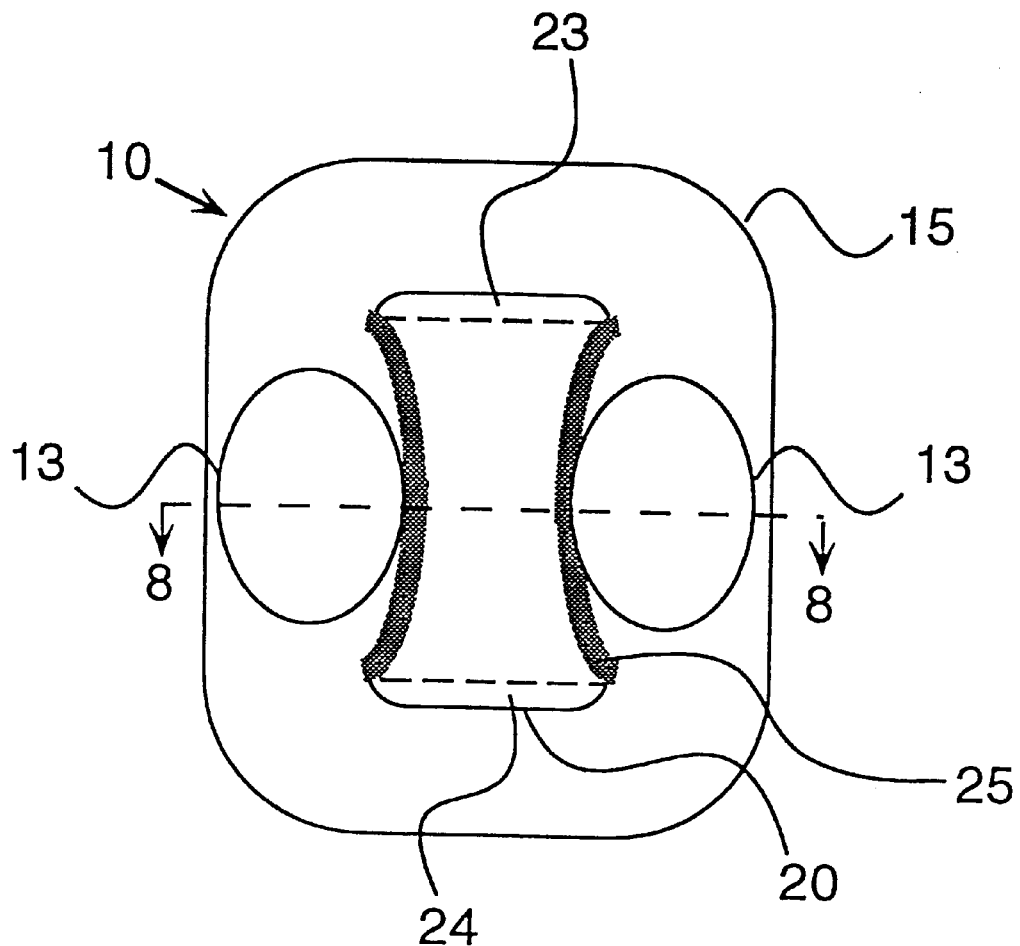
FIG. 7 is a top view of an incontinent brief.
Figure 8:
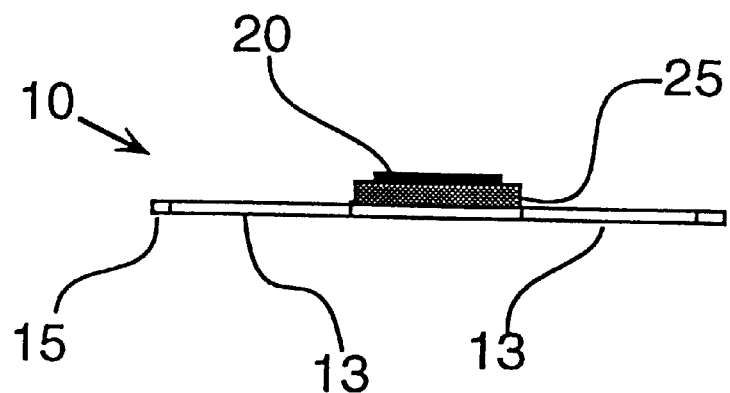
FIG. 8 is a cross-section view of the incontinent brief shown in FIG. 7 along section lines 8—8.

A particularly useful incontinent brief is shown in FIG. 7. The disposable or non-disposable, breathable incontinence brief 10 consists of four parts. An outer shell or pant 15, the barrier web made according to the present invention is a breathable or non-breathable shedding shield 20, a disposable or non-disposable absorbent pad 25. The outer shell or pant 15 is a barrier web made according to the present invention is breathable but void resistant. The incontinence brief has holes 13 for the legs of the wearer. The shedding shield 20 can be either breathable or non-breathable but is impermeable to bodily fluids and provides a dry patch that remains in contact with the skin. The shedding shield 20 can be fastened on one end 23 or both ends 23 and 24 to create either a pocket or a flap. The fastening means can be stitching or velcro. An absorbent pad 25 is enveloped in a foam or nonwoven wrapper which optionally can be treated with an antimicrobial agent such as iodine. (See Example 22) The pad can also optionally be treated with disinfectants and anti odor agents. The disposable absorbent pad 25 and wrapper are inserted under the shedding shield. 20 The shedding shield 20 allows the voided bodily fluids to be absorbed down, around and under the breathable shield while the shield remains dry. In this embodiment, the absorbent pad 25 is larger than the shedding shield 20 and overlaps the edges of the shedding shield 20. FIG. 8 is a cross-section view of the incontinence brief along section lines 8—8.

Figure 9:
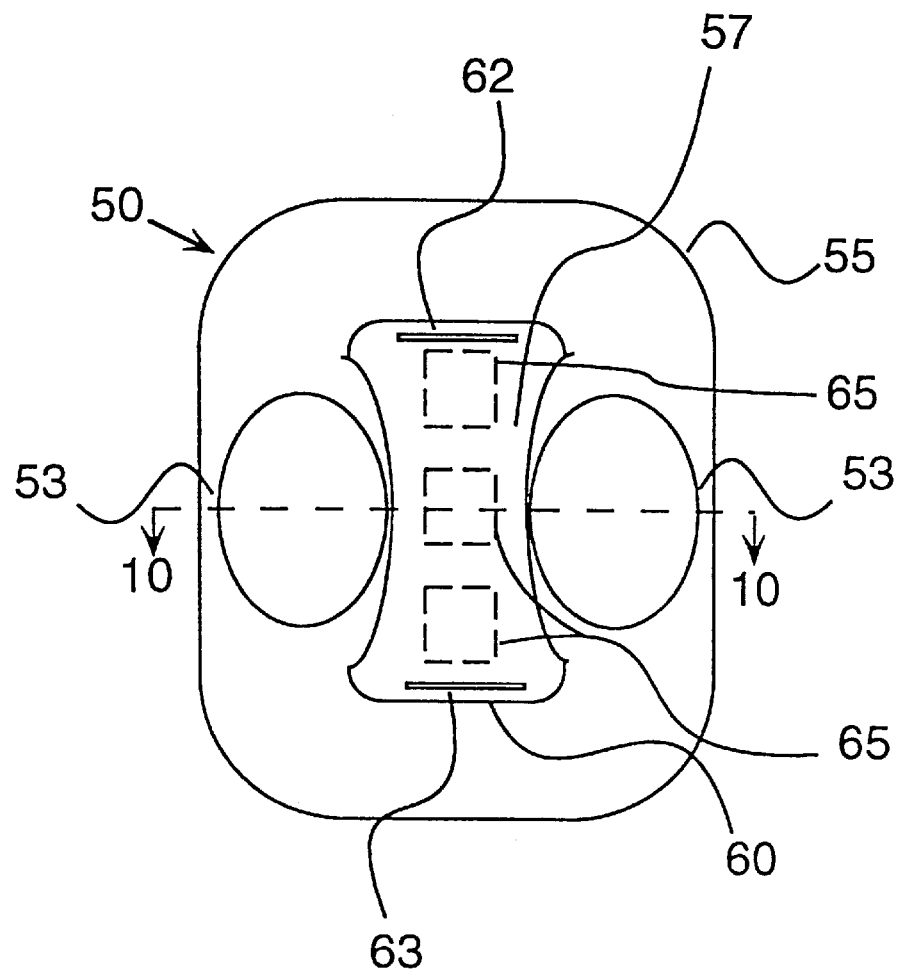
FIG. 9 is a top view of an incontinent brief.
Figure 10:
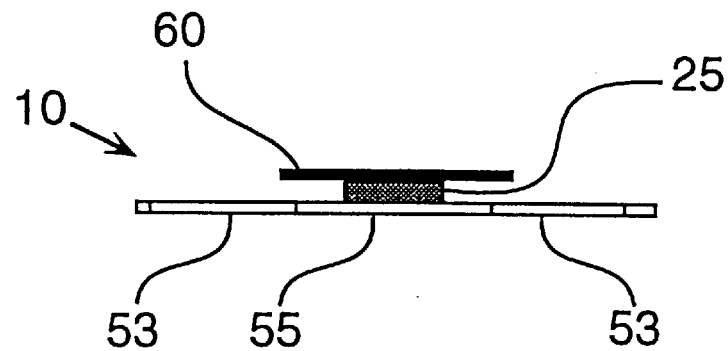
FIG. 10 is a cross-section view of the incontinent brief shown in FIG. 9 along section lines 10—10.

In another embodiment shown in FIG. 9, the disposable or non-disposable, breathable brief 50 consists of four parts. an outer shell or pant 55, a breathable or non-breathable shedding shield 60 and a plurality of disposable or non-disposable absorbent pads 65. The incontinence brief has holes 53 for the legs of the patient. In this embodiment, the outer shell or pant 55 is a barrier web made according to the present invention and is breathable but void resistant. The shedding shield 60 is fastened at one end 62 to create either a pocket or a flap and fastened at the opposite end 63 to create a pocket 57. At least one end is fastened by velcro or remains unfastened to allow access to the disposable absorbent pad or pads 65. The shedding shield can be permeable or impermeable to bodily fluids. One or more pockets 57 which contain the disposable absorbent pad or pads 65 are inserted or formed into the outer shell. The absorbent pads 65 optionally are enveloped in a foam or nonwoven wrapper which optionally can be treated with an antimicrobial agent such as iodine. (See Example 22) The pad can also optionally be treated with disinfectants and anti odor agents. FIG. 10 is a cross-section view of the incontinence brief along section lines 10—10.

With respect to bandages and surgical gauze, the present invention is particularly useful in that various wound healing agents can be incorporated into the polymer on the web and thereby aid in the healing of the wound which is physical contact with the bandage or surgical gauze prepared according to the present invention. These agents include, but are not limited to, various growth factors such basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors $\alpha$ and $\beta$ (TGF-$\alpha$ and TGF-$\beta$), interleukin-8 (IL-8); granulocytemacrophage colony stimulating factor (GM-CSF); the interleukins, and the interferons.

Other agents that can incorporated into the barrier webs of the present invention are acid mucopolysaccharides including, but are not limited to heparin, heparan sulfate, heparinoids, dermatan sulfate, pentosan polysulfate, chondroitin sulfate, hyaluronic acid, cellulose, agarose, chitin, dextran, and carrageenin.

Proteins that are especially useful as wound healing agents include, but are not limited to, collagen, cross-linked collagen, fibronectin, laminin, elastin, and cross-linked elastin and hyaluronic acid or combinations or fragments thereof.

The fabric is especially suited as a barrier to prevent or control the spread of infectious microorganisms, especially in career apparel for health care workers. The webs made according to the present invention are particularly useful in environments where there is a risk of blood contamination. The career apparel from webs made according to the present invention can be manufactured so that microbial transmission throughout the fabric is inhibited, but air flow is not blocked.

Another advantage of the barrier webs prepared according to the present invention is the capability of manufacturing webs that can selectively exclude microorganisms based on the size of the microorganisms. Accordingly, for those applications where only large microorganisms are a problem, such as certain bacteria, protozoa or fungi, the barrier web can be manufactured so that these larger microorganisms are excluded. The physical size comparison is shown in the following table:

| Organism | Size or Size Range (microns) |
|---|---|
| Effective Porosity of the Web | 0.025 to 100 |
| Viruses | |
| Foot & Mouth | 0.008–0.012 |
| Influenza | 0.070–0.080 |
| Rabies | 0.100–0.150 |
| HBV | 0.042–0.047 |
| HCV | 0.027–0.030 |
| HIV | 0.080–0.110 |
| Ebola | ≈0.970 |
| φX174 bacteriaphage | 0.025–0.027 |
| Bacteria | |
| *Escherichia coli* | 0.50–3.0 |
| *Staphylococcus aureus* | 0.80–1.0 |
| *Spirillum volutons* | 13–14 |
| Gas Molecules | 0.0004 |
| Water vapor | |

In addition, the webs made according to the present invention can be manufactured with antimicrobial or disinfecting agents incorporated into the polymer layer. Among the many chemicals (including nutrients such as $O_2$ and fatty acids) that are bacteriostatic and even bactericidal at sufficiently high concentrations, the term "disinfectant" is generally restricted to those chemicals that are rapidly microbiocidal at low concentrations. In contrast to most chemotherapeutic agents, which interact with various active metabolic systems, most disinfectants act either by dissolving lipids from the cell membrane (detergents, lipid solvents) or by damaging proteins or nucleic acids (denaturants, oxidants, alkylating agents, sulfhydryl reagents).

For example, a fabric can be treated according to the present invention with urethane and then exposed to a iodine/potassium iodine solution. Fabric treated in such a way exhibits a wide spectrum of antimicrobial activity. The iodine treated fabric has the further advantage of being "recharged" by exposing the fabric to an iodine solution. Thus, such an article, for example, a fabric insert in an incontinent brief, can be reused simply by washing the insert and then exposing the fabric insert to iodine. Thus, medical/surgical garments can be made into disposable, reusable, rechargeable, antimicrobial protective products. These products include crotch pads, bandages, surgical gowns and surgical gown webs, wound coverings, cast interliners, blankets wall coverings, upholstery, surgical drapes and patient gowns.

It is to be understood that the present invention includes the incorporation of other antimicrobial agents, including antifungal agents, antibacterial agents, anti viral agents and antiparasitic agents. Examples of antimicrobial agents that can be used in the present invention include, but are not limited to isoniazid, ethambutol, pyrazinamide, streptomycin, clofazimine, rifabutin, fluoroquinolones, ofloxacin, sparfloxacin, rifampin, azithromycin, clarithromycin, fluoroquinolones, dapsone, tetracycline, doxycyline, erythromycin, ciprofloxacin, doxycycline, ampicillin, amphotericin B, ketoconazole, fluconazole, pyrimethamine, sulfadiazine, clindamycin, lincomycin, azithromycin, clarithromycin, pentamidine, atovaquone, paromomycin, diclazaril, acyclovir, trifluorouridine, foscarnet, and ganciclovir.

It is to be understood that the antimicrobial agent can be incorporated into the polymer so that the agent is released over a period of time. In this way, the barrier web retains its ability to kill or inhibit microorganisms over a long period of time.

Webs manufactured according to the present invention that have antimicrobial molecules in the surfaces can be used to produce a wide variety of articles of manufacture. For example, garments made from the barrier webs can be made that fit over the clothes of a health care worker. These garments can be gowns or coats or can be wide mesh webs that are capable of preventing blood or other body fluids from splattering when they are splashed on the health care worker. If the garment or mesh has a disinfectant or an antimicrobial agent incorporated into the silicone surface, the garment will not only prevent the splattering of blood from a patient but, at the same time, kill or inhibit the growth of infectious organisms that might reside in the blood or body fluid of the patient.

Another product that can be manufactured using the barrier webs according to the present invention are sterile filtration masks. Using the enhanced surface chemistries described herein, masks can be made from the barrier webs that can be used by the worker that may be in contact with potentially dangerous microorganisms. These masks will prevent the transmission of the microorganism prior to contact with the skin or mouth and, if the polymer has an antimicrobial agent incorporated therein, the microorganisms will be inhibited or killed.

The present invention also includes webs with polymers applied thereto according to the present invention wherein the polymers have proteins incorporated into the polymer before application to the fabric. For example, a 10,000 Dalton β pleated sheet protein such as Crosilk (Croda, Inc., N.Y., N.Y.) The liquid silicone composition can be comprised of polysiloxane polymers containing reactive vinyl carbon to carbon double, along with a platinum catalyst, appropriate fillers and an organo silicone hydrogen compound. The crosslinking cure occurs by a platinum catalyzed hydrosilation reaction whereby the organosilicone hydrogen compound, which is difunctional, adds across the vinyl double bonds of two different polysiloxanes. The incorporation of "Crosilk" protein into the silicone composition is followed by the impregnation of a fabric with the mixture, and the silicone is heat cured to crosslink the system.

Although not wanting to be bound by the following hypothesis, it is believed that the protein is attached to the silicone by a reaction similar to the hydrosilation reaction which is also occurring. Addition of proteins with different tertiary or quaternary configurations will impart different physical characteristics to the fabric being treated.

Another aspect of the present invention is the use of the webs treated according to the present invention in the preparation of bioactive surfaces. This includes the incorporation of antibodies, antigens, enzymes, or other bioactive molecules into the polymer to be applied to the fabric, or other surface thereby forming a surface with the bioactive molecule attached thereto. A major advantage of this aspect of the present invention includes the fact that because the bioactive molecule is incorporated directly into the surface at a high concentration, more bioactive molecule can be exposed to the reactive medium. This results in a higher reaction rate. This would result in a much higher signal in, for example, a diagnostic kit utilizing specific antibodies. According to the present invention, the active site of the bioactive molecules can be oriented toward the surface of the fabric (or fiber comprising the fabric) thereby further increasing the binding activity or other reaction activity depending upon the bioactive molecule that is being incorporated into the film.

The present invention can be used to manufacture barrier webs that will not only provide a physical barrier to microorganisms, but will also provide surfaces that will specifically bind particularly dangerous microorganisms such as the human immunodefficiency virus (HIV) or Ebola virus. Combinations of additives or modifiers are also contemplated as part of the present invention. For example, antibodies that are specific for HIV can be incorporated into the polymer surface along with an antimicrobial or disinfectant agent thereby giving the surface the ability to specifically bind the HIV and, at the same time, neutralize the virus through the action of the antimicrobial or disinfectant agent. This is particularly important when working with patients which are known to be infected with the virus.

Because the present invention lends itself to the formation of bioactive surfaces, i.e., surfaces with biologically active agents thereon, the barrier webs are excellent supports for diagnostic applications.

Various assay methods, including but not limited to immunoassays, may be employed using the bioactive surfaces according to the present invention to measure the level of an analyte physically present in body fluids or other fluids by use of one or more binding agents such as antibodies. The following techniques can also be used to measure analytes in other fluids including industrial waste fluids and the like. The methods can also be adapted to isolate and purify particles from a suspension of different particles. For example, the present invention can be used to isolate and purify a specific cell population such as stem cells using the CD34 antibody incorporated into the barrier web. The following are illustrative, but not limiting, examples of such assay methods.

A first or direct method includes reacting a fluid sample thought to contain an analyte with a conjugate of a detectable marker or label and an antibody specific to an antigenic site on the analyte molecule to cause formation of antigen antibody complexes. The quantity of the analyte contained in the sample can be determined by measuring the extent of reactivity of the antibody to the analyte by standard signal detection techniques which would be dependent upon the type of label used, as discussed more fully below. In general the analyte-antibody complexes are separated from the unbound assay components and then the complexes are qualitatively and/or quantitatively analyzed.

As a variation of the first or direct assay method rather than conjugating the marker directly to the anti-analyte antibody, the marker can instead be conjugated to a suitable, specific binding partner of the anti-analyte antibody. The binding partner may be a monoclonal or polyclonal antibody directed at a unique determinant site on the anti-analyte antibody or an anti-immunoglobulin specific for the anti-analyte antibody. In this assay method, the secondary antibody advantageously may be of the type which is more readily conjugated to a label. Also, use of the secondary antibody avoids the possibility that conjugation of the marker to the anti-analyte antibody may adversely affect the affinity of the anti-analyte antibody. Further, the secondary antibody can be of a polyclonal nature, which generally is easier to isolate than are monoclonal antibodies. In addition, use of a secondary antibody directed to the anti-analyte antibody may result in larger complexes which are more easily separated from uncomplexed components of the assay.

Both the presence and quantity of the analyte in a sample also may be analyzed with a competitive immunoassay. In this type of assay, a known amount of a anti-analyte antibody and a known amount of labeled analyte are incubated with a sample to be assayed. Since the antibody does not favor either the labeled or unlabeled analyte, the antibody binds to the labeled and unlabeled analyte in proportion to their relative amounts present. Thereafter, the bound components of the assay, analyte-antibody and labeled analyte-antibody complexes, are removed from free or unreacted components and then the extent of binding measured by the standard techniques, discussed below. In this type of competitive assay system, a specific concentration of anti-analyte antibody is employed. Preferably, a dilution of analyte antibody is chosen so that the antibody binds to approximately 50% of the labeled antigen. This results in a bound-to-free ratio of the elements of approximately 1:1. It is to be understood, however, that other dilutions of anti-analyte antibody may be chosen without departing from the scope or spirit of the present invention.

In the foregoing competitive assay, prior to the assaying of a particular sample, varying amounts of unlabeled analyte are incubated with a fixed quantity of labeled analyte and a fixed quantity of the anti-analyte antibody. The extent to which the labeled analyte binds with the anti-analyte antibody is then measured for each sample containing the known amount of unlabeled analyte. From the results of these measurements, a standard curve may be prepared depicting the extent of binding between the labeled analyte and the antibody in the presence of a quantity of unlabeled analyte. Then, when a particular sample containing an unknown amount of unlabeled analyte is assayed, the concentration of the unlabeled analyte in the sample may be determined from the standard curve once the extent of which the labeled analyte binds to the anti-analyte antibody is measured.

The present invention also contemplates use of the novel bioactive surfaces on the barrier webs with the antibodies prepared and isolated in double determinant immunoassays for measuring the level of analyte in body fluid. In this type of assay, a first antibody reactive with a unique recognition site on the analyte molecule is placed in contact with the sample to be tested. If analyte is present in the sample, it binds specifically to the first antibody molecules. After the unbound analyte is separated from the bound analyte, for instance by washing, the first antibody-analyte complex is contacted with a second antibody reactive with a different recognition site on the trapped analyte molecule, which second antibody attaches to the bound analyte in a dose-dependent fashion. It will be appreciated that in the double determinant assay it is important that the two anti-analyte antibodies are reactive to unrelated epitopes on the analyte molecule thereby avoiding stereotypic effects caused by the binding of the two antibodies to the analyte molecule.

The second antibody may be labeled so that the extent of binding of the second antibody to the analyte can be measured by standard procedures. Rather than labeling the second antibody directly, a binding partner for the second antibody which is conjugated to a marker may be employed. The binding partner may be a secondary antibody that is specific for the second antibody. As noted above, by avoiding the necessity of labeling an anti-analyte antibody, the possibility that the labeling may cause a change in the affinity of the antibody is eliminated. Moreover, the antibody employed as the secondary antibody may be chosen on the basis of desirable characteristics, such as ease of labeling, ability to generate and ease of separating bound from unbound antibody. It will be appreciated that in the double determinant assay by using a first antibody to trap the analyte molecule and then a second antibody to detect the molecule, a very sensitive immunoassay results.

Although various types of immunoassays have been discussed above, it will be appreciated that numerous variations of the assays may be employed as well as other types of immunoassays. For instance, the labeled or unlabeled analyte protein could be replaced with a suitably labeled analyte specific peptide with which the antibody(ies) is (are) reactive.

The present invention contemplates the use of various types of insoluble separation barrier webs made according to the present invention in conjunction with the above immunoassays. For example, in the competitive assay, the anti-analyte antibody, may be covalently or noncovalently bound to the barrier web. The same is true for the anti-analyte antibody employed in the double determinant assay. The barrier web may be composed of the plastic or glass microtiter plate wells or other reaction vessels in which the assay itself is carried out. Alternatively, the support may be in the form of a plastic, cellulose or glass fiber disk, plate or strip which is dipped into or otherwise placed in contact with the analyte-containing fluid sample. Barrier web supports may be of various compositions, such as polyvinyl, polyacrylamnide, polystyrene, acrylamide, polypropylene or polycarbonate. Also, the support may be composed of matrices of various configurations, such as a mesh material or beads of spherical or other shapes which are contained in a reaction vessel. Various activating compounds may be employed to covalently bind the antibody to the barrier web, which is well known in the art. Such activating agents may include, for instance, cyanogen bromide (CNBr), carbodiimide, glutaraldehyde, polyethylenegycol and tannic acid.

Because the porosity of the barrier webs of the present invention can be controlled, the barrier webs are ideally suited as size exclusion filters. For example, if one desires to exclude microorganisms from a solution that are over a certain size, one can select a barrier web with pore sizes that are below the desired exclusion size. One can then pour or force the solution through the barrier web thereby trapping microorganisms that are greater than the pore size of the barrier web. One can optionally include a barrier web with a bioactive surface to further control what particles can pass through the web.

The assays of the present invention are preferably conducted in a liquid medium at moderate pH and temperature. The medium may be of an aqueous nature; however, ideally it is composed of a buffered salt solution media, such as 0.1 molar ("M") Tris buffered saline containing 3% of albumin (ovine. bovine or human). Preferably, the pH of the medium is in the range of about 5–10 and, more preferably. in the range of about 6–9, and ideally about 7.2. The pH is chosen to facilitate specific binding between the analyte and the antibody or antibodies, while avoiding any significant negative effect on the signal produced by the marker conjugated to the antibody. To achieve the desired pH and maintain it during the assay procedure various buffers may be employed. Examples of suitable buffers include, for example, N-2-hydroxy-ethylpiperazine-N-2-ethane-sulfonic acid ("HEPES"), Tris, borate, phosphate, carbonate and barbital.

As noted above, the present assay may include one or more incubation procedures. For example. in the double determinant assay method, the sample of interest is incubated with a first anti-analyte antibody which has been bound to an insoluble support. Thereafter, in a second procedure, the first antibody analyte complex is incubated with a second anti-analyte antibody. The length of the incubation period and the incubation temperature will depend, to a large extent, on the binding rate of the analyte to the antibody and on the type of label employed. The incubation periods may range from a few minutes to several hours, typically from about 5 minutes to up to 24 hours. The incubation temperatures will generally range from about 1° C. to 32° C., and ideally approximately 4° C.

In the present invention, the anti-analyte antibody itself or a separate, secondary antibody directed to the anti-analyte antibody may be conjugated with a detectable marker to produce a signal related to the presence of analyte. In the test sample, the detectable marker can be selected from among fluorophores, colored dyes, enzymes, chromophores, coenzymes, chemilluminescent materials, enzyme inhibitors, paramagnetic materials such as gadolinium, ferritins and radionuclides that are known in the art. Illustrative, but non-limiting examples of particular enzymes which might be employed include horseradish peroxidase, alkaline phosphatase, and β-galactosidase. Illustrative examples of colored dyes include, but are not limited to, amido black and eosin. Illustrative fluorescent compounds include, without limitation, fluorescein, isothiocyanate, dansyl, propidium iodine as well as phycophores, such as phycoerythrin.

The detectable marker may also be composed of a radioactive isotope. The technique used for labeling the antibody varies with the type of radioactive isotope employed. For instance, labeling can be accomplished by replacing one of the atoms of the antibody molecule with a corresponding radioactive isotope. As a specific example, a hydrogen atom could be replaced with tritium ($^3H$); a carbon atom could be replaced by carbon-14 ($^{14}C$); or, a strontium atom replaced with strontium-38 ($^{38}Sr$). In an alternative labeling process, rather than replacing the atoms of the antibody with a radioactive isotope, an isotope may be added to the antibody molecule. Such radioactive isotopes in common use include, but are not limited to, iodine-125 ($^{125}$I) and iron 59 ($^{59}$Fe).

It will be appreciated that the particular marker or label employed depends on various factors, such as the particular type of immunoassay being used and the biological and biochemical characteristics of the anti-analyte antibody or secondary antibody being labeled. Whatever type of marker is employed, it, of course, should not cause any significant change in the specificity between the labeled antibody and its specific recognition site.

After each of the various incubation steps in the assay of the present invention, the complexed or bound components of the assay typically are separated from the unbound components, noncomplex analyte, excess anti-analyte antibodies and secondary antibodies. The methods may include simply washing with, for instance, a saline solution alone or combined with centrifugation. The separation may include ultrafiltration, dialysis or salt precipitation. Other separation procedures may be based on differential biochemical migration, for instance, chromatography, electrophoresis, chromatoelectrophoresis and gel filtration. The particular type of separation method(s) employed will depend upon the specific immunoassay procedure used and the characteristics of the assay reagents.

Diagnostic Kit

The present invention also includes a diagnostic kit for carrying out the analyte assays disclosed above to detect the presence of an analyte. In its most basic form, the kit for measuring the analyte comprises a container and a web that has been treated with a curable thixotropic polymer composition with molecules that bind the analyte positioned therein.

The particular components of the kit can correspond to the particular assay procedure being employed. In perhaps its simplest embodiment, the diagnostic kit may include a polyclonal or monoclonal antibody directed against analyte which has been conjugated with a suitable marker capable of producing a detectable signal. To carry out the assay, the test sample is placed in contact with the antibody-marker conjugate. Thereafter, the complexed components are separated from free components of the assay and then the signal produced by the marker is detected and quantified in either the bound or free components of the immunoassay reaction. As noted above, the assay components include an insoluble matrix comprising the barrier web with the suitable binding agent incorporated therein, buffers to maintain the desired pH of the immunoassay reaction and binding media to dilute the fluid sample. The kit may also include reagents required for the marker to produce a detectable signal, such as an appropriate enzyme reagent for ELISA assay, or agents to enhance the detectable signal.

In another illustrative, but nonlimiting example, the diagnostic kit may include a polyclonal or monoclonal antibody directed against analyte and a secondary antibody directed against the anti-analyte antibody, which second antibody is conjugated to a suitable marker capable of producing a detectable signal. As in the embodiment of the assay kit discussed above, this kit embodiment also may include other additional components. To carry out the assay, a test sample is placed in contact with the anti-analyte antibody and then the complexed components separated from the free components using the barrier web of the present invention as a solid support with the appropriate binding agent thereon. Thereafter, the complex components are placed in contact with the labeled secondary antibody which specifically couples with the anti-analyte antibody bound to the analyte. After the unbound secondary antibody is separated from the complexed components of the assay, the signal produced by the label is measured in either the bound or free components of the assay reaction.

In a further illustrative embodiment of the present invention, the diagnostic kit may include the components necessary to carry out the double determinant assay procedure described above. This particular kit composition includes first and second antibodies directed against separate determinant sites on the analyte molecule. Preferably, the first antibody is covalently or noncovalently coupled to a barrier web made according to the present invention. The second anti-analyte antibody may be conjugated with a suitable marker capable of producing a detectable signal or alternatively a third labeled secondary antibody directed against the second anti-analyte antibody may be employed. Again, as noted above, the kit may include various additional components to optimize or facilitate the assay procedure.

The present invention also provides substrates for growing cells such a procaryote or eucaryote cells. The substrates comprise webs that have various growth factors incorporated into the polymer surface as defined herein and in copending patent applications. These webs can be placed in containers, such as conventional fermenters with the appropriate nutrient solutions thereon. Cells can be seeded on the webs and allowed to grow at the appropriate temperature. The cells or the products produced by the cells can be easily harvested from the fermentors.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLE 1

Liquid Silicone Polymer Preparation 100 parts by weight of the curable liquid silicone polymer available commercially from Mobay as "Silopren® LSR 2530" was mixed in a 1:1 ratio, as recommended by the manufacturer. A Hockmayer F dispersion blade at low torque and high shear was used to do the mixing. To this mixture were added 5 parts by weight of BSF "Uvinul 400" and 5/10 parts by weight Dow Corning 7127 accelerator, believed to be a polysiloxane but containing an undisclosed active accelerated ingredient.

EXAMPLES 2–19

Liquid Silicone Polymer Preparation with One or More Modifiers

The procedure of Example 1 was repeated with various other commercially available curable viscous liquid silicone polymer compositions. To this product system a substituted benzophenone and other additives are optionally added, the results of which are shown in Table III. These examples illustrate that more than one additive can be combined in the practice of this invention. All parts are by weight.

TABLE III

Illustrative Silicone Resin Compositions

| EXAMPLE NO. | STARTING SILICONE RESIN | MIXTURE RATIO OF PACKAGED COMPONENTS[1] | SUBSTITUTED BENZOPHENONE NAME | PARTS | OTHER ADDITIVES NAME | PARTS |
|---|---|---|---|---|---|---|
| 1 | Silopren ® LSR 2530 | 1:1 | Univul 400 | 5 | 7127 Accelerator | 5/10 |
| 2 | Silastic ® 595 LSR | 1:1 | Uvinul 400 | 5 | Syl-Off ® 7611[2] | 50 |
| 3 | SLE 5100 | 10:1 | Uvinul 400 | 5 | Sylox ® 2[3] | 8 |
|   | Liquid BC-10 | 1:1 |  |  |  |  |
| 4 | Silopren ® LSR 2530 | 1:1 | Uvinul 400 | 5 | Hydral ® 710[4] | 10 |
| 5 | Silopren ® LSR 2530 | 1:1 | Uvinul 400 | 5 | Silopren ® LSR Z3042[5] | 1 |
| 6 | SLE 5500 | 10:1 | Uvinul 400 | 5 |  |  |
| 7 | Silopren ® LSR 2540 | 1:1 | Uvinul 400 | 5 |  |  |
| 8 | SLE 5300 | 10:1 | Uvinul 400 | 5 |  |  |
| 9 | SLE 5106 | 10:1 | Uvinul 400 | 5 |  |  |
| 10 | Silopren ® LSR 2530 | 1:1 | Uvinul 400 | 5 | Flattening Agent OK412 ® [6] | 4 |
| 11 | Silopren ® LSR 2530 | 1:1 | Uvinul 400 | 5 | Nalco[5] 1SJ-612 Colloidal Silica[7] | 50 |
| 12 | Silopren ® LSR 2530 | 1:1 | Uvinul 400 | 5 | Nalco ® 1SJ-614 Colloidal Alumina[8] |  |
| 13 | Silastic ® 595 LSR | 1:1 | Uvinul 400 | 5 | 200 Fluid[7] | 7 |
| 14 | Silopren ® LSR 2530 | 1:1 | Uvinul 400 | 5 |  |  |
| 15 | Silastic ® 595 LSR | 1:1 | Uvinul 400 | 5 | Zepel ® 7040[10] | 3 |
| 16 | Silastic ® 595 LSR | 1:1 | Uvinul 400 | 5 | Zonyl ® UR[11] | 1/10 |
| 17 | Silastic ® 595 LSR | 1:1 | Uvinul 400 | 5 | Zonyl ® FSN-100[12] | 1/10 |
| 18 | Silopren ® LSR 2530 | 1:1 | Uvinul 400 | 5 | DLX-600 ® [13] | 5 |
| 19 | Silopren ® LSR 2530 | 1:1 | Uvinul 400 | 5 | TE-3608 ® [14] | 5 |

Table II Footnotes:
[1] Ratio listed is that recommended by the manufacturer.
[2] Syl-off ® (registered trademark of Dow Corning) is a crosslinker.
[3] Sylox ® 2 (registered trademark of W. R. Grace Co.) is a synthetic amorphous silica.
[4] Hydral ® 710 (registered trademark of Alcoa) is hydrated aluminum oxide.
[5] Silopren ® LSR Z/3042 (registered trademark of Mobay) is a silicone primer (bonding agent) mixture.
[6] Flattening Agent OK412 ® (registered Trademark of Degussa Corp.) is a wax coated silicon dioxide.
[7] Nalco ® 1SJ-612 Colloidal Silica (registered trademark of Nalco Chemical Company) is an aqueous solution of silica and alumina.
[8] Nalco ® 1SJ-614 Colloidal Alumina (registered trademark of Nalco Chemical Company) is an aqueous solution of silica and alumina.
[9] 200 Fluid (registered trademark of Dow Corning) is a 100 centistoke viscosity dimethylpolysiloxane.
[10] Zepel ® 7040 (registered trademark of duPont) is a nonionic fluoropolymer.
[11] Zonyl ® UR (registered trademark of duPont) is an anionic fluorosurfactant.
[12] Zonyl ® FSN-100 (registered trademark of duPont) is a nonionic fluorosurfactant.
[13] DLX-6000 ® (registered trademark of duPont) is polytetrafluoroethylene micropowder.
[14] TE-3608 ® (registered trademark of duPont) is a polytetrafluoroethylene micropowder.

EXAMPLE 20

Internally Coated Fiber Encapsulated, Interstice Filled Fabric Preparation

A complete, stepwise, application of the inventive method in the production of an encapsulated fiber fabric was as follows.

The selected base fabric was TACTEL® (gold color) #612071 available from ICI Americas, Inc. This fabric was 100% woven nylon. If desired, this and other fabrics may be calendered to modify surface texture, geometry and porosity. The fabric was weighed and measured. Its initial weight is 3.1 ounces per square yard. Its thickness equals 9 mils. The fabric was next washed with detergent, rinsed thoroughly, and hung to air dry. The fabric was soaked in water, wrung dry, and weighed. The water retained was equal to 0.8 g water/g fabric. The fabric was then treated with a water repellent fluorochemical, a 2% solution by weight of Zepel® 7040. In order to do so the fabric must be soaked in a 2.5% solution of Zepel® water-repellent chemical in distilled water. This was because:

$$\frac{(1 \ g \ fabric)(0.02)}{0.8 \ g \ water} = 0.025$$

The treated fabric was then run through a wringer and air dried. Next, the fabric was heated in an oven for 1 minute at 350°. This heating sinters the water repellent fluorochemical. The fabric with its fluorochemical residue is then run as in the FIG. 7 embodiment. The silicone polymer composition is applied at 1.0 oz./sq. yd. The polymer composition is GE 6108 A/B in a 1:1 ratio and can be considered to be a viscoelastic liquid that flows only under the shear forces resulting from the pressured controlled placement. The polymer composition is believed to return very substantially to its original viscous condition almost immediately upon release of the pressure. The polymer composition was believed to flow a short distance within the matrix of the fabric during the short time that it was, because of pressure shearing forces, of lowered viscosity. Therefore, a number of "flows" may be usefully generated with multiple blades in order to properly distribute the polymer composition in its preferred position substantially encapsulating the surfaces of the fabric's fibers.

Finally, the treated fabric was run through a line oven, of approximately 10 yards in length, at 4–6 yards per minute, and was cured at 325–350° F. It then passed through a series of idler rollers and is rolled up on a take-up roll, completing the tension zone. The resultant fabric has a non-tacky thin film of silicone that was internally coated to form a fiber encapsulated, interstice-filled layer in the fabric.

EXAMPLE 21
Evaluation of Fiber Encapsulated Fabric Properties

The test results of the original versus the produced fiber encapsulated fabric of Example 20 were as follows:

TABLE IV

| FABRIC | ORIGINAL FABRIC | ENCAPSULATED |
|---|---|---|
| Spray Rating (1) | 20 | 100 (reverse = 100) |
| Rain Test (2) | Fail | Pass |
| Abrasion Test (cycles) (3) | 1,800 | 3,200 |
| Moisture Penetration (4) | Saturated | 0.0 g |
| Hydrostatic Resistance (psi) (5) | 1 | 2 |
| MVTR (g/M$^2$/day)* (6) | 4,414 | 2,362 |
| Weight (oz/yd$^2$) | 3.1 | 4.1 |

Amount Impregnated = 1.4 oz/yd$^2$
*Environmental chamber at 104° F. and 74% humidity.

TABLE V

| LAUNDERING TEST (7) | TIMES WASHED | | | |
|---|---|---|---|---|
| (Spray Ratings) | Initial | 5× | 10× | 15× |
| Impregnated Side | 100 | 90 | 90 | 90 |
| Reverse Side | 100 | 90 | 90 | 90 |
| Unimpregnated Treated Fabric | 100 | 80 | 80 | 40 |

Accelerated Weathering Test (8)
Samples placed in QUV weatherometer for 72 hours.
Original=7
Impregnated Side=9
Reverse Side=8

(1) The spray test was conducted in accordance with AATCC 22-1974. It measures water repellency of a fabric sample on a scale of 0–100, with a reading of 100 designating a completely water repellent fabric.
(2) The rain test was conducted in accordance with AATCC 35-1985. It measures resistance of a fabric sample to penetration of water under static pressure from a shower head of 3 feet/5 minutes. A fabric is stormproof when less than 1.0 gram of water is absorbed by a standardized blotter used in the test.
(3) The abrasion test was conducted in accordance with Federal Test Method Standard 191 A, Method 5306. Abrasion resistance is measured by mounting a fabric sample on a Taber Abraser Model 174 and measuring the number of cycles before the fabric begins tearing apart.
(4) The moisture penetration test was conducted in accordance with AATCC 70-1994. It measures the resistance of fabrics to wetting by water, by measuring the penetration of water into, but not through, the fabric.
(5) The hydrostatic resistance test was conducted in accord with Federal Test Method Standard 191A, Method 5512. The test measures a fabric samples' resistance to water under pressure using the Mullen's Burst Test methods and apparatus. Test results are expressed in pounds per square inch at which water beads penetrate the fabric.
(6) The moisture vapor transmission (MVTR) test was conducted in accordance with ASTM E96-B. The test measures the amount of moisture vapor passing through a fabric sample in a controlled environment during a 24 hour period. The obtained MVTR figure is expressed in grams of water/square meter of surface/24 hour day. The environmental chamber was held at 104° F. and 47% humidity.
(7) A laundering test of the conventional household type was performed. Fabric samples were washed with Tide® detergent. There was no drying. A spray test was subsequently carried out after each wash to determine the effect of the washing.
(8) The accelerated weathering test was conducted in accordance with ASTM G-53. Samples of original and impregnated fabrics were placed in the weatherometer of QUV Company and results were compared. (All readings were based on a graduated color scale of 0–20; 10 designated the original color, while 0 designated a white out.)

EXAMPLE 22
Iodine As A Biocidal And Antimicrobial Agent with Polyurethane as a Reactive Site This example demonstrates the preparation of a biocidal or self-sterilizing web. Polyurethane, Sancor® 898 in a latex form, was mixed with silicone polymer, Dow Corning 2962 (Parts A & B 50:50) in the ratios of 0%, 5%, 10%, 15% and 100%, by weight respectively. Various fabric webs such as Burlington 4040, 4045 and Versatec, were treated with 15–20% weight addon of the above polymer mixtures in accordance with the practice of this invention. The fabrics were cured at 350° F. (176° C.) for 26 seconds. The treated fabrics were dipped in an iodine solution bath containing 2% iodine in a 2.4% KI solution or 2% iodine in an ethanol solution for 10–30 seconds at room temperature and rinsed in a freshly-distilled water bath until no free iodine came off. The iodine/silicone/urethane-treated fabrics were then air dried and observed to be yellowish on the silicone/urethane treated side, indicating the presence of iodine.

A culture of XL Blue *E. Coli* was prepared in a refrigerated LB Agar and grown for 9 hours. Two drops of cultured XL Blue *E. Coli* were added to four streaked LB Agar plates and spread with a bent sterile 1 mL pipette. The iodine/silicone/urethane-treated fabric web samples were placed (treated side down) on the LB Agar plates and grown in an incubator at 37° C. After 24 hours, an area of growth inhibition was observed for all samples, which is indicative of the active killing sites for each piece of treated fabric. The treated fabric was then washed, charged with free iodine and then re-tested for antimicrobial activity. The growth of bacteria was inhibited both under and around the treated fabric samples.

A latex web, instead of a fabric web, when treated with silicone/polyurethane, also shows the ability to bind free iodine. After dipping in 2% iodine ethanol solution, the iodine/silicone/urethane-treated latex web samples were placed on LB Agar plates. Again, bacteria growth inhibition was observed both under and around the samples.

EXAMPLE 23
Protein Additives As Hand Altering Agents, Surface Chemistry Modifiers And Antibody Binding Sites The proteins used in the practice of this invention were "Silk-Like-Protein 3 (SLP-3)," produced by Protein Polymers, Inc. (San Diego, Calif.) and "Crosilk," produced by Croda, Inc. (New York, N.Y.). Crosilk is a 10,000 molecular weight protein made by hydrolyzing silk, and is comprised of 17 different amino acid segments, ranging in percent weight of 0.1% to 20.3%. The silicones used herein are Mobay Silopren® LSP 2530 and Dow Corning Silastic® LSR 2303. The webs used herein are Eggplant Supplex, Black Cordura, and a 48% Nylon/52% Cotton blend.

Prior to mixing the protein with the silicone polymer, the dimensions of the protein particles need to be adjusted to a suitable particle size such as 0–2 microns in length and 0–2 microns in diameter. This can be accomplished by grinding the protein particles with a small amount of silicone polymer, in a ball mill in a solvent such as xylene. The solvent is used to lower the viscosity of the silicone polymer composition in the ball mill. Generally, the mixture in the ball mill is composed of about 5% SLP-3, 50% silicone polymer composition and about 45% of xylene. The grinding of protein can also be done without a solvent. After grinding, additional silicone polymer composition was added to the protein/silicone mixture to produce a mixture containing about 2.5% by weight protein. The xylene solvent evaporates during this process. The final protein/silicone mixture was then applied to the webs in accordance with the practice of this invention. The treated web was cured at 320° F. for 2 minutes. Any xylene residue remaining evaporates during the final curing stage. The resulting webs showed improved hand feel (tactility), moisture vapor permeability, and surface exposure as shown by further binding tests with antibodies. The permeability test results are summarized in the following table.

TABLE VI

MVTR Results of Webs Treated with SLP-3 Protein Additive

| Materials | MVTR ($g/m^2 \cdot day$) | Breathability |
|---|---|---|
| Eggplant | 964 | — |
| LSP 2530 w/SLP-3 | 1504 | 156% |
| Eggplant + DWR | 2089 | — |
| LSP 2530 w/SLP-3 | 2718 | 130% |
| Black Cordura | 3387 | — |
| LSP 2303 w/SLP-3 | 4115 | 122% |
| Black Cordura | 2823 | — |
| LSP 2530 w/SLP-3 | 9799 | 347% |
| 48% Nylon/52% Cotton | 4076 | — |
| LSP 2530 w/1% SLP-3 | 4203 | 103% |
| LSP 2530 w/5% SLP-3 | 7133 | 175% |

DWR - Durable Water Repellent such as a fluorochemical composition.

Each row shows both the control sample (without polymer and without SLP-3 protein) and a treated web sample with the polymer and the SLP-3 protein additive. The moisture vapor transport rate increased with the SLP-3 protein. This shows that the protein assists in the transport of moisture vapor.

Samples of webs treated with the SLP-3 protein additive were exposed to the anti-SLP-3 antibody, washed, then exposed to radioactively labelled "protein A." The sample then was washed, and analyzed for the radioactively labeled "protein A." Protein A is a bacterial protein which specifically binds to antibodies. The tested samples contained 1% and 5% by weight SLP-3 protein and then antibodies were allowed to bind. The control samples contained the same amount of SLP-3 protein but no anti-SLP-3 antibodies. The samples containing more SLP-3 protein showed larger amounts of bound antibodies. This result shows that the SLP-3 protein was surface exposed and created a binding site for antibodies.

Crosilk was used as an additive in Mobay LSP 1530 silicone polymer. This mixture was applied to webs such as Arthur Kahn Blue Cotton, Arthur Kahn White Tactal and Patagonia Red Supplex. All webs were cured two minutes in an oven at 320° F. The presence of the hydrolyzed silk did not inhibit the cure of the silicone polymer. The treated webs showed a slightly improved feel and no real appreciable difference in the MVTR results of the fabric. This result shows that although various proteins can be utilized, the same functionality does not appear. Some proteins can be used specifically for binding antibodies, some for altering the "feel" of the fabric, some for modifying the surface characteristics of the polymer and/or web, and some for altering the moisture vapor transport rate.

EXAMPLE 24

Pigments, Dyes and Proteins on Fibers

This example illustrates the addition of pigments, dyes, and proteins to polymers and the application of the polymer compositions onto fibers. The following is a preferred procedure for processing fibers, particularly for use in carpets.

1. Tension a single bundle of fibers across a lab encapsulator. This set-up presents a knife-over-air process condition on the carpet fiber.
2. Comb the fibers using a very fine comb to individually isolate the filaments to prevent them from sticking or spot welding together.
3. Apply the polymer composition with the dye, pigment, or protein mixed into it, onto the surface of the tensioned fibers.
4. Take semi-dull encapsulating applicator, such as a flex knife, and shear the polymer composition to get a uniform, fully encapsulated fabric.
5. Once again, comb fibers to individually separate and prevent them from sticking together.
6. Pin the comb to one end of the lab encapsulating frame and cure the polymer composition.

The above process was used to apply a red pigment onto Nylon 6 CF carpet fibers. The polymer composition used was a 50/50 DG2303 mixed with A-50 red pigment. Twenty lbs. of tension was applied across the fibers. The flex knife was pulled across the fibers ten times to shear thin the polymer composition. The treated fibers were cured for five minutes at 320° F. The red pigment appeared uniformly around the fibers when examined under a microscope.

The above process was also used to apply a polymer composition and a red pigment onto BASF 70/32 Bright Tri-Lobal Nylon 6 yarn. Seven 14 inch strands were tensioned at about 10 lbs. The polymer composition was SLC 5106 A&B in a 10:1 ratio mixed with 30% weight add-on of silicone red (8010.94 40% pyrazalone-VT). The composition was shear thinned and then cured at 320° F. for five minutes. The red pigment appeared uniformly around the fibers when examined under a microscope. This shows the encapsulating aspect of the polymer composition and the ability to introduce red dyes and pigments around individual fibers.

The above process was also used to apply the SLP-3 Beta silk protein to individual fibers. The polymer composition used was DC-2303 A&B in a 1:1 ratio mixed with 10% by weight of SLP-3 Beta silk protein. The protein was ground up in a mill grinder before addition to the polymer composition. Ten lbs. of tension was applied. The fibers were washed with warm water and then dried. Six shears were applied with the shearing means on the top and bottom of the fibers. Between shears, the excess was wiped off. The composition was cured at 320° F. for five minutes. The presence of the SLP-3 protein was seen uniformly around the fibers under a microscope.

Additional samples were run using the same procedure, and the results are shown in the table below:

TABLE VII

| Company | Product Description | Obstacles | Solution | Process | Successes |
|---|---|---|---|---|---|
| Shaw Industries | 1800 Denier Bulked Polypropylene Beige | Sensitive to heat | Add platinum Reduce cure heat | Heat set 5/5/ shear Appears to be encapsulated | Addition of Red Dye in polymer Ran SLC 5106 Tried platinum accelerator |
| Shaw Industries | 2600 Denier Dull Polypropylene Blue | Sensitive to heat Colored Fiber | Add platinum Reduce cure Use DC2303 | Heat Set Reduce heat cure Appears to be encapsulated | Addition of Red Dye Ran SLC 5106 Success with accelerator Appears to encapsulate |
| Shaw Industries | 3050 Denier Nylon 6 Fiber Bulked Multicolor | Multiple Fibers Fiber Welding Bulked Tri-Lobal Fiber | Use all polymers High shear Cure relaxed High speed shear | Heat set 5/5 shears Add accelerators Appears to be encapsulated | Reduces shrinking Tried all polymers Isolated best process 35 mm picture taken Tired ceramic acrylic |
| BASF Corp. | 70/32 Brt. Tri-Lobal Nylon 6 for Textiles | Small Filament Tightly spun Residual Tri-Lobal | High tension High shear Water clean High speed | 6/6 shear Appears to be encapsulated | Tried SLC5106 Tried Red Dye in polymer |
| BASF Corp. | Nylon 6 Unbulked 8800 Denier CF Yarn White | 8800 Denier Fiber Welding Residuals | Alt. Process Splitting up fiber Water wash Solvent wash | 6/6 shears Appears to encapsulate Tried all polymer Curing process | Tried all polymers Red Dye in polymer Picture taken Added accelerators Trying to process all fiber |
| DuPont | Antron Nylon Bulked Fibers | Bulked Faceted Fiber Residuals Fiber Welding | High Tension High shear 6/6 shears Heat set Cure relax state | Heat set 6/6 shears Appears to encapsulate Add Red Dye Cure relaxed | Red Dye in polymer Tried SLC5106 Add accelerators Need better flow character Try different polymer |
| DuPont | Bulked Twisted Finished Antron Carpet Yarn | Thick Yarn Multi-Twist Residuals Entanglement | High Tension High speed High shear Alt. polymer | 10/10 shear Shear blade Add accelerator Tried SLC5106 Red Dye | Shear thinning Increased bulk Fiber welding Higher speed needed |

EXAMPLE 25

A Flattening Agent as an Additive

In this example, the look of the treat web was flattened by adding an amorphous silica compound labeled OK 412, produced by Degussa, Inc. (Frankfurt, Germany), available through its pigment division in Teterboro, N.J., to the silicone polymer prior to application to the web. The introduction of this material into the silicone polymer reduced the glossy look of the final cured silicone composition, allowing the web to maintain its cotton-like look and hand. The silicone polymer used herein is Mobay Silopren® LSR 2530. The flattening agent OK 412 was mixed in the ratio of 80% by weight LSR 2530 A/B, 17% by weight OK 412, and 3% by weight White mineral spirits. The mixture was then applied in accordance with the practice of this invention, to Milliken Poplin (65% polyester/35% cotton) and Arthur Kahn Dune (100% cotton), respectively. The webs were pre-treated with a 3.5% fluorochemical solution of F31X durable water repellant (DWR). The silicon/OK 412 treated webs were cured in an oven at 350° F. for 1.5 minutes. All webs treated with the silicone/OK 412 mixture showed significant improvement in abrasion resistance while flattening the glossy look and maintaining the feel of the web. The test results of the above samples are summarized in the following table:

TABLE VIII

Test Results of OK 412 Treated Webs

| Fabric Materials | Spray Test | Rain Test | Abrasion Test |
|---|---|---|---|
| Milliken Poplin (65% polyester/35% cotton) LSR 2530 w/OK412 + DWR | 0 90 | saturated 0 g | 75 cycles 125 cycles |
| Aurthur Kahn Dune (100% cotton) LSR 2530 w/OK412 + DWR | 0 90 | saturated 0 g | 75 cycles 150 cycles |

DWR - Durable Water Repellent such as a fluorochemical composition.

Each row shows both the control sample (without polymer and without additives) and a treated web sample with the polymer and the OK 412 additive.

EXAMPLE 26

Topical Application of a Flattening Agent

In this example, the look of the treat web was flattened by topically applying an amorphous silica compound labeled OK 412, produced by Degussa, Inc. (Frankfurt, Germany), available through its pigment division in Teterboro, N.J., to the silicone polymer treated web prior to curing. The introduction of this material upon the silicone polymer treated fabric reduced the glossy look and altered the feel of the fabric after curing. The silicone polymer used herein is GE 6108 A:B (1:1).

The fabric was a Navy Blue 3-ply Supplex (100% Nylon). The fabric was stretched to a tension of 15 Newtons. The polymer was applied and shear thinned into the fabric using a shearing knife. The polymer weight add-on was approximately 29%. The samples were then sprinkled with OK412. This was done with a fine screen that dispersed the powder upon shaking. The sample was then passed under a nip to force the additive into the fabric and into the polymer composition. The sample was cured for 30 seconds at 350° F. A sutter test was run on the sample and the sample was rinsed with water and dried.

Upon rinsing the fabric the white spots on the navy blue supplex dissappeared. After drying, the spots reappeared, indicating that the additive adhered to the polymer composition in the fabric. This shows that a topically applied additive will adhere to the polymer composition and will retain its functionality.

EXAMPLE 27
Copper Particles as an Additive

This example demonstrates the preparation of a web containing sub micron copper particles. Sub micron copper particles were mixed with silicone polymer, Dow Corning 2303 (Parts A&B 50:50) in the ratios of 0%, 5%, 10%, and 20% by weight respectively. Various fabric webs such as Burlington 4040, 4045 and Versatec, were treated with 15–20% weight add-on of the above polymer mixtures in accordance with the practice of this invention. The fabrics were cured at 350° F. (176° C.) for 26 seconds. The samples were then examined with scattering electron microscopy (SEM). The results appear in FIG. 6f and are discussed in the following examples explaining the SEM figures.

Figure 6A:
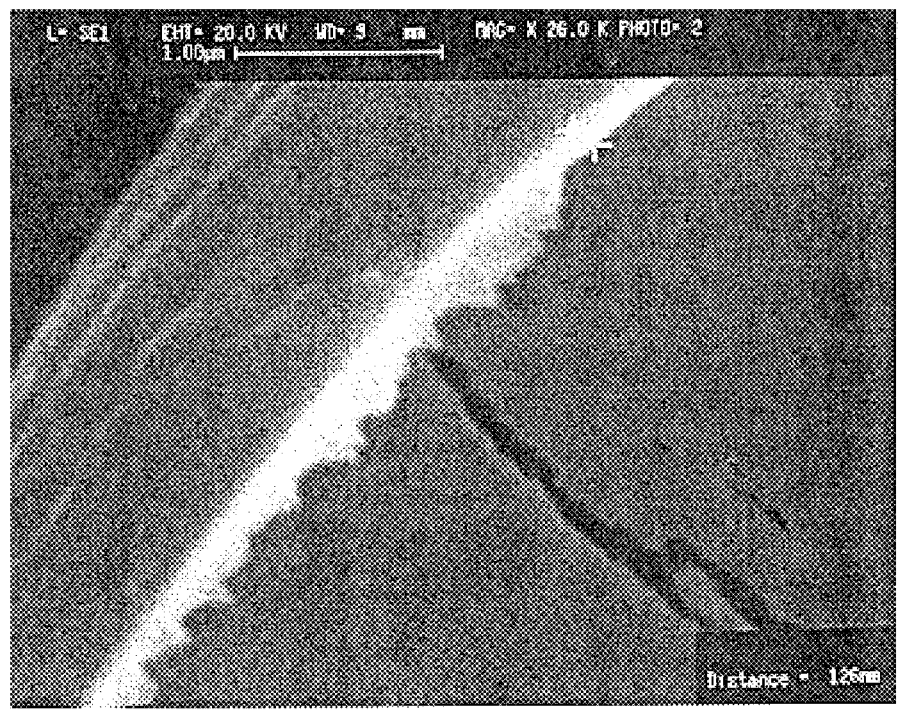
FIGS. 6a through 6g are scanning electron microscopy (SEM) photomicrographs and elemental analyses which depict various results in fabrics, fibers and filaments from back scatter evaluation tests.

EXAMPLE 28
Description of Fabric Controlled Placement Through Scanning Electron Microscope (SEM) Photomicrographs FIG. 6a depicts a cut end of a filament illustrating a thin film encapsulation in white. A crack was created in the filament with a high temperature electron beam. This crack continues under the surface of the thin film The filament has been cut and the thin film has been stretched or elasticized by the cutting of the filament. The two arrows in the upper right corner show the thickness or distance represented by the black box in the lower right corner as 126 nm.

Figure 6B:
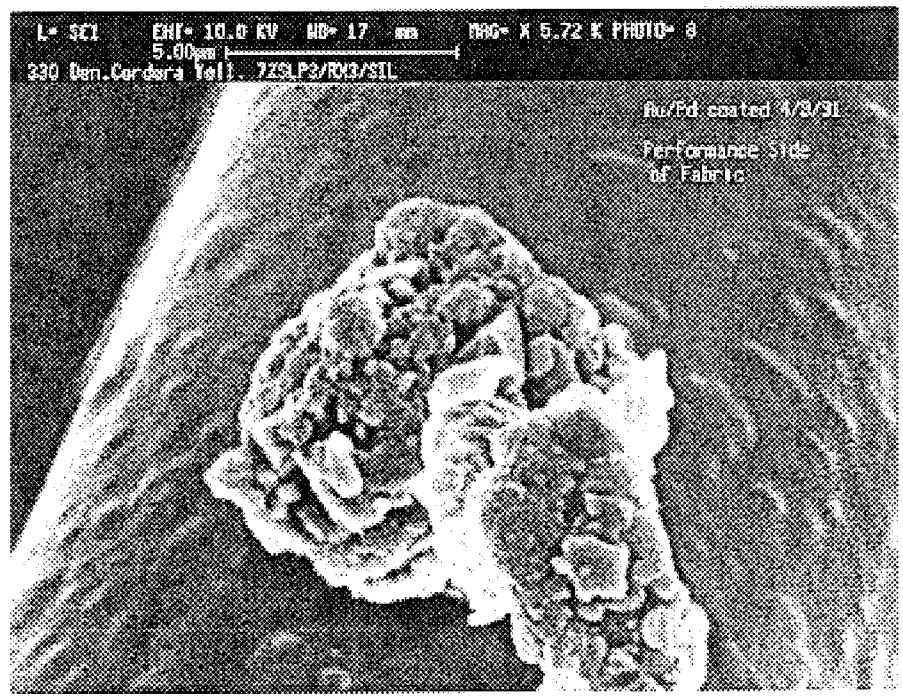

FIG. 6b depicts an isolated image on 330 Denier Cordura single filament fiber processed with the micro-finish fiber coating technology, magnified 5,720 times. The Bioengineered Comfort™ polymer containing engineered protein and solid silicone was used in the process with a moderate degree of shear. The image on top of the fiber is an undispensed protein polymer which clearly illustrates the presence of the protein after the micro-finish fiber coating process. The surface morphology has very small protein polymer particles encapsulated in the solid silicone polymer and is homogeneously dispersed throughout the film system on the fiber.

Figure 6C:
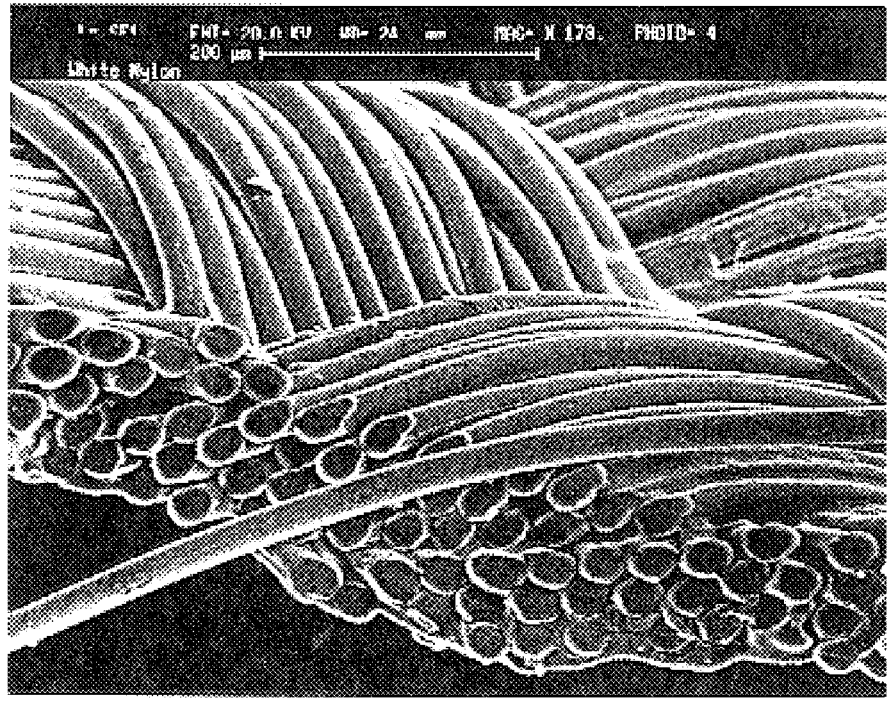

FIG. 6c is an image of a white nylon magnified 178 times. The application side is shown at the bottom left hand comer of the image. The upper portion of the image is the non-application side. At the upper right corner is the intersection of the warp and fill fiber bundles, where the polymer presence can clearly be seen on the fibers. The internal layer of polymer that creates the liquid barrier or resistant property can be seen along the bottom right corner of the picture. This internal layer is a combination of polymer filling some interstitial spaces and polymer "glueing" together the fibers and filaments of the web.

Figure 6D:
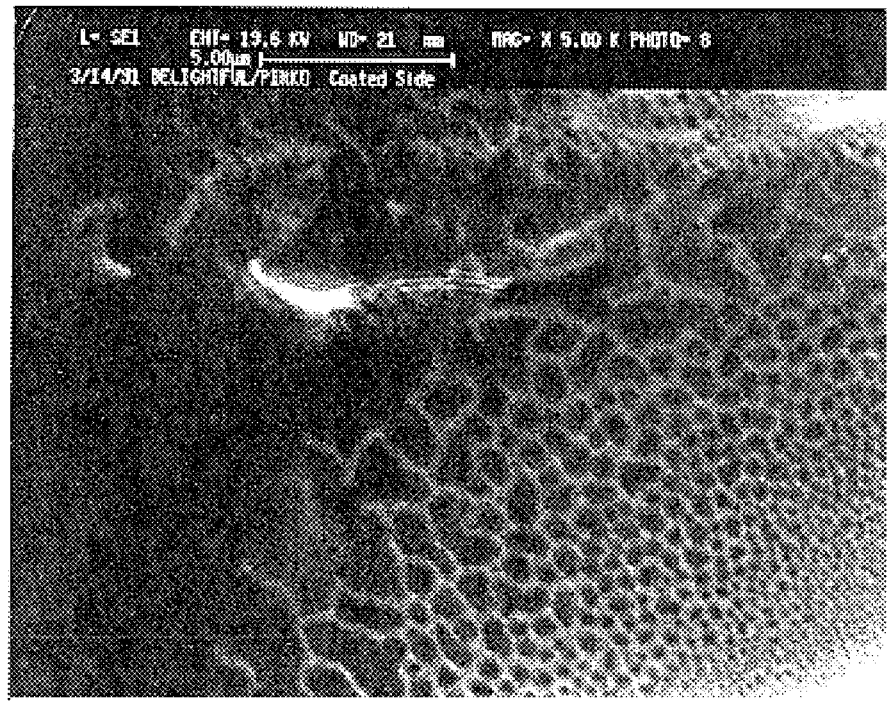

FIG. 6d depicts the surface of a circular fiber that has had a defracted broad electron beam of approximately 2000 degree centigrade defracted across the image area. The imaging shows a destructive burn pattern of a fluorochemical package on the surface of the siloxane film. On the surface of the filament the image depicts the surface migration of the fluorochemical from the fiber through the thin film and oriented on the surface of the silicone.

Figure 6E:
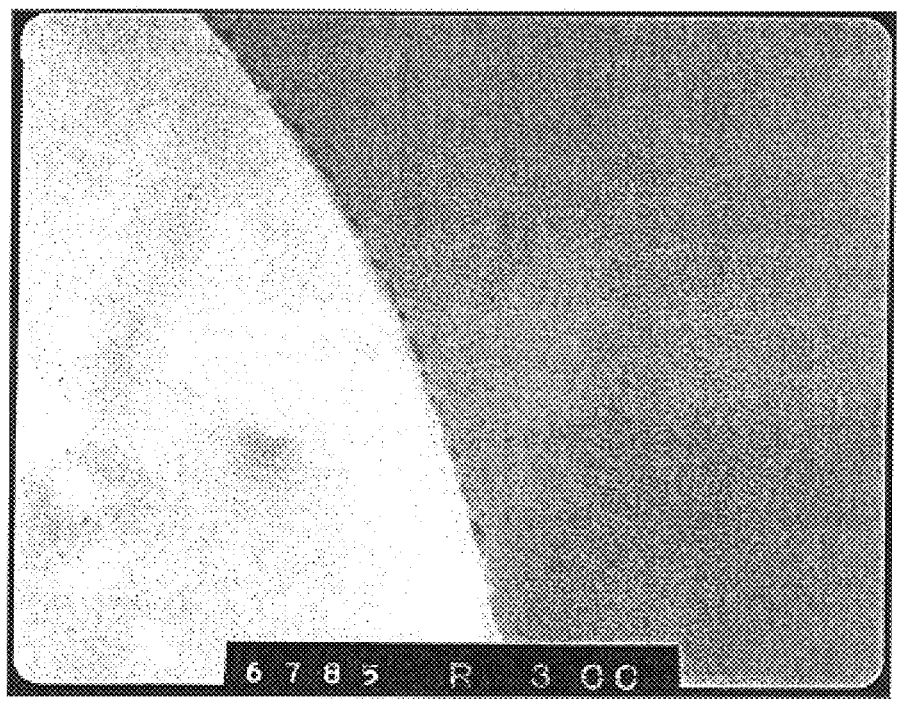

FIG. 6e is a Tunneling Electron Microscopy (TEM) image of a thin cross section of a filament encapsulated with polymer. The lighter image on the lower side of the frame is a polyester filament. The black spherical dots on the outer edge of the fiber are extremely dense processed material. In this imaging technique, the darker the image, the denser that specific material.

Figure 6F:
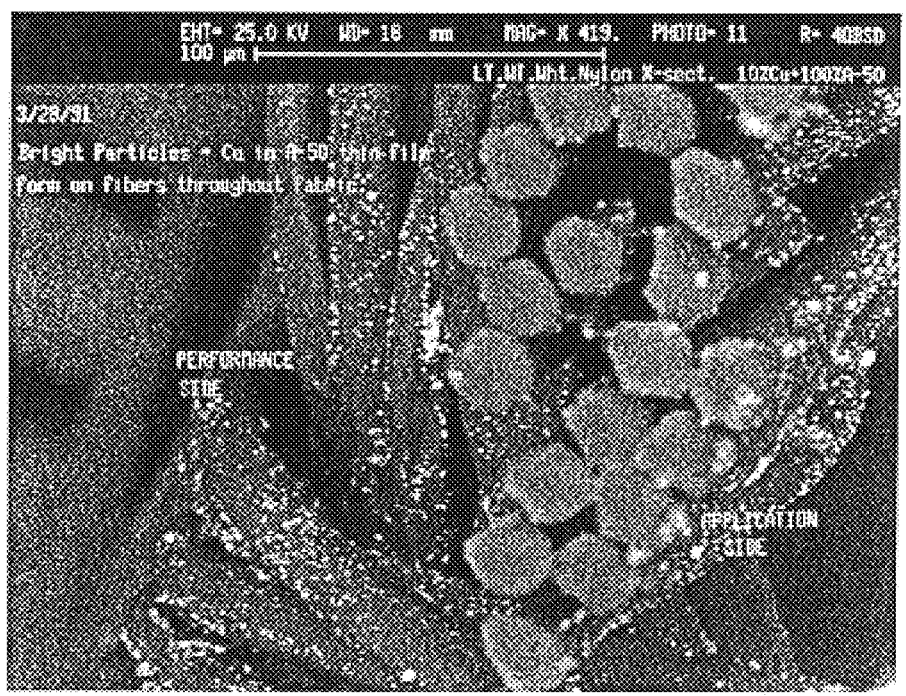
Figure 6G:
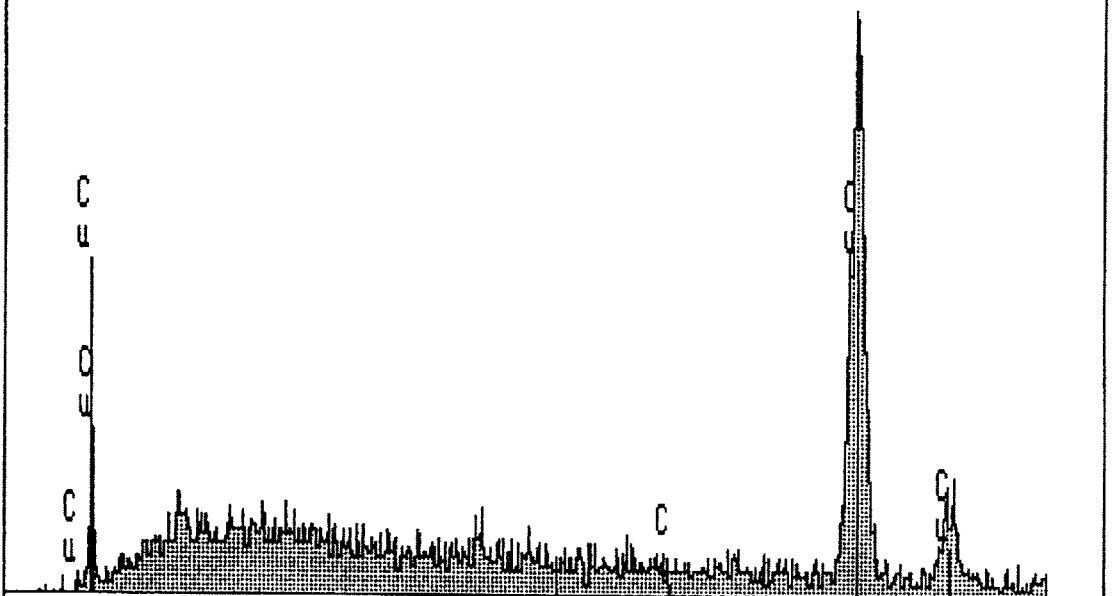

FIG. 6f depicts a nylon fabric magnified 419 times with bright particle tracer images and a cross sectional image of a nylon fabric. These bright particles are submicron metal particles dispersed throughout the fabric in the processed film. The addition of bright copper submicron particles in the polymer allows secondary back scatter mode to illustrate the complete encapsulation ability of the controlled placement technology. The left side of the image is the performance side of the fabric which is the non-application side of the polymer, but it is clear, with the presence of the glowing brightness of the copper submicron particles throughout the performance side of the fabric, that controlled placement technology successfully encapsulates completely around the fibers throughout the fabric structure. The other clear unique feature of the controlled placement technology is that each fiber is still independent. This differentiation allows the controlled placement technology's processed fabrics to retain exceptional hand and tactile quality, while still imparting performance characteristics. On the left side of the fabric, directly underneath the printed text "performance side", an elemental analysis was conducted and the outcome of that analysis is depicted in FIG. 6g. The result clearly shows a strong presence of submicron copper particles.

In the next examples that involve accelerated weathering, abrasion, water repellency, moisture penetration, and rain testing, data is provided for a Tactel fabric identified as Deva Blue. The fabric is 100% nylon, available from Arthur Kahn and identical in composition, preparation, and enveloping specification to that of the Hot Coral presented in previous examples.

EXAMPLE 29
Accelerated Weathering Test

The results of weathering upon a treated web of this invention are shown in actual tested sample pieces comparing original fabrics with embodiments of the enveloped fiber fabrics of this invention.

In every case, the enveloped fiber fabric samples were found to have significantly better weathering characteristics than the original untreated fabrics as determined by accelerated weathering tests. Even the reverse side (compared to the treated side) of an enveloped fiber nylon fabric of the Tactel® type was improved over the original fabric. In addition, the excellent "hand" of the enveloped fiber fabric was found to have been maintained after the accelerated weathering test.

The test performed conforms to each of the following performance standards:
  ASTM G-53 light/water exposure materials
  ASTM D-4329 light/water exposure-plastics
  General Motors Test spec TM-58-10
  ISO 4892 Plastics exposure to lab light The procedure used for the accelerated weathering testing involved subjecting fabric samples to four hours of high-intensity ultraviolet light, alternating continuously with four hours of water condensation, wetting the fabric in the dark. This alternating exposure (four hours on, four hours off) to high-intensity ultraviolet light and water wetting, simulates outdoor environmental conditions in a vastly accelerated manner, quickly degrading unprotected dyes and fibers. The methods and apparatus used for this test was a QUV Accelerated Weathering Tester from The Q-Panel Company, 26200 First Street, Cleveland, Ohio 44145.

The results obtained on some sample fabrics are expressed in Table VII. In this Table, results are expressed in the form of "A/B" where A and B are numbers. The number "A" is the color rating on a graduated scale from 0 to 10. The number 10 equals perfect (original) condition where 0 equals a white color and a completely faded fabric. The number "B" is the number of hours of weathering transpiring when the number "A" rating was obtained.

grain of the specimen. Comparisons of the enveloped fiber fabric to the untreated fabric were based upon a scale 0 through 10, where 0 was a completely torn specimen, and 10 was the new (or starting) sample.

Each test procedure used a single 7 inch diameter fiber enveloped fabric specimen, and a single 7 inch diameter original (untreated) fabric specimen. The procedure used was as follows:

1. A test specimen of the fiber enveloped fabric with a 7 inch diameter was cut.
2. An equally-sized specimen of control (untreated) fabric was cut.
3. The fabric specimen was mounted on the rotating wheel securely and the clamps were screwed down.
4. The counter was set.
5. The vacuum power adjustment was set. (For this experiment, vacuum was set at 80.)

TABLE IX

Accelerated Weathering Testing

| ORIGINAL FABRIC | ORIGINAL FABRIC WEATHERED | ENVELOPED FABRIC WEATHERED | REVERSE SIDE WEATHERED | COLOR RATING (rating/hours) 10 = Perfect 0 = white color fades out |
|---|---|---|---|---|
| TACTEL ® Deva Blue 9-420-6-1 10/0 | 3/159 | 8/159 | | After 159 hrs., enveloped fabric significantly less weathered than original; original nearly white; enveloped fabric still light blue. |
| TACTEL_ Hot Coral 9-420-6-2 (AKA 18) 10/0 | 5/24 | 10/24 | 9/24 | After 24 hrs., enveloped fabric is significantly less weathered than original, as was reverse side. |

EXAMPLE 30

Abrasion Resistance Testing

The results of abrasion resisting testing clearly show that enveloped fiber fabrics of this invention have superior wear characteristics compared to the untreated original (starting) fabrics. In most cases, the enveloped fiber fabric samples underwent twice as many cycles as the untreated samples without evidencing tearing in the samples. Such results can be explained by theorizing that the envelopment with silicone polymer of the yarns and fibers comprising a fabric, provides such treated yarns and fibers with a lubricity agent so that abrasive action was minimized and the integrity of the fabric was preserved significantly longer. The anti-abrasion characteristics also applied to the minimized effects of one fiber rubbing against another fiber, or of one yarn against another yarn.

This experiment compared the abrasion resistance of embodiments of the enveloped fiber fabrics of this invention with untreated fabrics. The durability of each fabric test specimen was determined by the Taber Abraser. Each specimen is abraded for the number of cycles indicated. Comparisons were then made between the enveloped fiber fabrics of the invention and untreated fabrics. Specifically, this test method utilizes the Taber Abraser No. 174. An important feature of this abrader was that its wheels traverse a complete circle on the test specimen surface. Thus, the surface was abraded at all possible angles relative to the weave or 6. The abraser was started.
7. At the procedurally specified number of revolutions, the abraser was stopped and each fabric sample was rated at a value between 0 and 10.

Illustrative results of the test on some sample fabrics are shown in Table X.

Abrasion Testing

Numeric Grade of Abrasion 0–10

0—Total failure of fabric specimen. Fibers are torn apart
5—Fabric specimen is starting to tear. Fabric is noticeably thinner
10—Original unabraded fabric specimen

TABLE X

| SPECIMENS | UNTREATED FABRIC | ENCAPSULATED FABRIC | COMMENTS |
|---|---|---|---|
| Hot Coral Tactel | 5 1,000 cyc. | 7 1,000 cyc. | Untreated sample is starting to tear, and enveloped sample was still intact. |

TABLE X-continued

| SPECIMENS | UNTREATED FABRIC | ENCAPSULATED FABRIC | COMMENTS |
|---|---|---|---|
| Deva Blue Tactel | 4 1,000 cyc. | 7 1,000 cyc. | Visible rips in untreated sample. Enveloped sample fibers were frayed. |

EXAMPLE 31

Breathability Testing

This test procedure followed the Modified ASTM E96-8 test. As shown by the results of this testing in the following Table, the fiber enveloped fabrics of this invention were found to have high breathability. This breathability was in excess of that needed to remove the average value of several thousand grams of perspiration generated daily by the human body. The results for the fiber enveloped fabrics of this invention were generally superior to the corresponding results measured under the same conditions for prior art treated fabrics, such as the Gore-Tex® brand fabric.

Breathability of a fabric sample was determined by accurately weighing the amount of water passing through such fabric sample under carefully controlled temperature and relative humidity conditions in an environmental chamber. The water weight loss from a cup whose mouth is sealed with a fabric sample was expressed as grams of water vapor per square meter of fabric per 24 hour day.

In an attempt to more realistically simulate what is actually occurring inside the apparel during exercise, a specially designed test was performed to measure outward water vapor transport (MVTR) in a "Bellows" effect. The test simulates the high volumes of moisture and air that mix within a garment that pass outward through it as air is drawn in resultant from activity. The enveloped fabrics of this invention were found to provide increased performance at a higher activity, or air exchange level than is achievable with corresponding untreated fabrics.

The "Bellows" MVTR breathability test was run inside of a controlled temperature/humidity chamber similar to the foregoing cup test. However, instead of a standard cup, each fabric sample was sealed over the open top of a special cup which was provided with an air inlet aperture in its bottom, thereby allowing air to be bubbled up through the sealed container at a controlled rate. A check valve at the air inlet operation prevents backup or loss of water from the container. The air bubbles passed upwardly through the water and out through the fabric sample mounted sealingly across the cup top along with the water vapor. Table XI illustrates some representation results obtained.

TABLE XI

Moisture Vapor Transport (MVTR)

| FABRIC | MVTR[1] |
|---|---|
| Made by a Method of the Invention Enveloped fiber fabric, Hot Coral Tactel ® | 13,600 |
| Commercial Products Gore-Tex\3-Ply Fabric | 10,711 |

Table Footnote:
[1]MVTR here references moisture vapor transport through a fabric sample as measured by the "Bellows" test with air delivered to the bubbler at 2 to 4 psi air pressure, in an Environmental Chamber at 100 to 102° F. and 38–42% relative humidity. MVTR is expressed as grams of water per square meter of surface per 24 hour day.

The MVTR data shown below is an example of a web where the fluorochemical is blooming from the fibers through the silicone thin film and re-orienting on the surface of the thin film. This data shows no significant reduction in moisture vapor transport rate with a fluorochemical additive on the surface of the silicone. The silicone polymer composition used was GE 6108 A:B (1:1), with 19.51% weight add-on, and the durable water repellent (DWR) was a fluorochemical composition that was added to the web as a pre-treatment.

TABLE XII

MVTR Results of Web Treated with a Fluorochemical Additive

| FABRIC | MVTR (g/m$^2$ · day) |
|---|---|
| Untreated Versatec, Passion Fruit (M032195A1E) | 1681.67 |
| Treated Versatec + GE 6108 + DWR | 1444.99 |

EXAMPLE 32

Water Repellency: Spray Testing

Water repellency spray testing is carried out according to AATCC Test Method 22-1974. The results of such testing show that the fiber enveloped Tactel®-type fabrics of the invention show excellent initial spray ratings initially, as do the original untreated fabrics which have been treated with water repellent chemicals such as fluorochemicals. Specifically, as the results shown below demonstrate, after ten machine washes, the treated side of a fiber enveloped fabric of the invention was found to remain highly water repellent, while, on the reverse side thereof, the original water repellency rating was found to have fallen significantly. The water repellency spray rating on the untreated fabric fell even more drastically. Excellent "hand" was retained after the test. It is believed that pretreatment with a fluorochemical having good water repellent properties can augment and even synergistically coact with the silicone resin used to produce fiber enveloped fabrics of this invention to produce superior spray ratings in such a fiber. The results are shown in Table XIII.

This test method is believed to be applicable to any textile fabric, whether or not it has been given a water resistant or water-repellent finish. The purpose of the test is to measure the resistance of fabrics to wetting by measuring the water-repellent efficiency of finishes applied to fabrics, particularly to plain woven fabrics. The portability and simplicity of the instrument, and the shortness and simplicity of the test procedure, make this method of test especially suitable for mill production control work. This test method is not intended, however, for use in predicting the probable rain penetration resistance of fabrics, since it does not measure penetration of water through the fabric.

The results obtained with this test method are believed to depend primarily on the resistance to wetting, or the water repellency, of the fibers and yarns comprising a fabric, and not upon the construction of the fabric. This test involves spraying water against the taut surface of a test fabric specimen under controlled conditions which produce a wetted pattern whose size depends on the relative water repellency of the fabric. Evaluation is accomplished by comparing the wetted pattern with pictures on a standard chart. The methods and apparatus and materials employed for this test were an AATCC Spray Tester, a beaker, distilled water, and the specimen fabrics.

The procedure followed for this test was as follows: a test specimen, which had been conditioned as procedurally directed, was fastened securely in a 15.2 cm (6") metal hoop so that it presented a smooth wrinklefree surface. The hoop was then placed on the stand of the tester so that the fabric was uppermost in such a position that the center of the spray pattern coincided with the center of the hoop. In the case of twills, gabardines, piques or fabrics of similar ribbed construction, the hoop was placed on the stand in such a way that the ribs were diagonal to the flow of water running off the fabric specimen.

250 milliliters (ml) of distilled water at 27° C. ±1° C. (80° F. ±2° F.) was poured into the funnel of the tester and allowed to spray onto the test specimen, which took approximately 25 to 30 seconds. Upon completion of the spraying period, the hoop was taken by one edge and the opposite edge tapped smartly once against a solid object, with the fabric facing the object. The hoop was then rotated 180 degrees and then tapped once more on the location previously held.

The procedure and methods and apparatus of this test were slightly modified from the specifications, as follows:

1. The spray nozzle holes were slightly larger than specified, but the flow rate of the nozzle was 250 ml/30 sec., as required.
2. The number of taps of the hoop was two instead of one.

For each wash test, a fabric sample was washed using a warm wash/cold rinse cycle with one cup of Tide® detergent and dried at a hot/dry cycle in a dryer, unless otherwise indicated. The test results were evaluated by comparing the wet or spotted pattern on the fabric sample after tapping the hoop with the standard rating chart. Results produced surface wetting, with no water completely soaking through the test fabric sample. The numbers were ratings based upon the standard chart. Such values are thus subjective deductions by an experienced experimenter.

EXAMPLE 33

Moisture Penetration Test

The results shown in the Table below demonstrate that all of the fiber enveloped fabrics of this invention test were significantly better than the original untreated fabrics with regard to resisting the penetration of water under the test conditions used. After the test, the "hand" of the tested fabric samples remained excellent.

The purpose of this test was to evaluate how well a fabric stands up to wetness under continuous pressure, such as kneeling on the ground, or sitting in a wet chairlift, for a period of 30 minutes. This test involves placing both a fabric sample and a standard blotter sample on top of a water container which contains 700 ml of tap water. The fabric sample and the blotter sample are each then subjected to a continuous pressure of 87 lbs. distributed evenly over 100 square inches of surface area for a period of 30 minutes. After this time, a visual inspection of the fabric is made for any water penetration, and the paper blotter is weighed to detect water gain or penetration.

The methods and apparatus employed for each such test was one 20 inch diameter aluminum pan, one 87 lbs. weight distributed evenly over 100 square inches of fabric, one paper blotter, 700 ml water, miscellaneous fabric scraps for cushioning and the test fabric sample pieces.

| | |
|---|---|
| Paper blotter dry weight: | 4.7 gm |
| Total weight applied to fabric: | 87 lbs. |
| Pressure evenly distributed over surface area of: | 100 sq. in. |
| Pressure: | 0.87 lbs./sq. in |

The procedure observed for this test was as follows:

1. 700 ml tap water was placed in the round pan.
2. The fabric sample was placed with one side facing the water.
3. One piece of dry blotter paper was placed over the fabric to cover the pan.
4. Scrap fabric was placed over the blotter paper to cushion the weight.
5. The 87 lb. weight was distributed evenly over the 100-square-inch area.
6. This assembly was left undisturbed for 30 minutes.
7. After this time period, the visual results were recorded.

TABLE XIII

Spray Test Results

| ORIGINAL FABRIC | | TREATED WEBS OF THE INVENTION | | | |
|---|---|---|---|---|---|
| | | Initial | | After 100 Washes | |
| Web Type & Number | Initial | Application Side | Non-Application Side | Application Side | Non-Application Side |
| Supplex H053194C | 100 | 100 | 100 | 70 | 80 |
| Med Blue 4040 M082994B-1E | 100 | 100 | 100 | 90 | 90 |
| Yellow 4040 M083094B-1B | 100 | 100 | 100 | 90 | 90 |

TABLE XIV

Fiber Enveloped Fabric of the Invention

| FABRIC SAMPLE AND THICKNESS | ENVELOPED SIDE OF FABRIC FACING WATER | NON-ENVELOPED SIDE OF FABRIC FACING WATER | CONTROL FABRIC |
|---|---|---|---|
| Deva Blue Tactel ® 0.009 microns | No water penetration through the fabric. No visible water spots. Paper weight = 4.7 gm Water gain = 0.0 gm | No water penetration through the fabric. No visible water spots. Paper weight = 4.7 gm Water gain = 0.0 gm | Failure - total saturation of fabric and blotter. |

EXAMPLE 34

Rain Test

In this testing, the rain test procedure of AATCC Method 35-1985 was followed.

The rain test results obtained demonstrate the clear superiority of the fiber enveloped fabric of the present invention as compared to the original untreated fabric. The data in the Table below shows that fiber enveloped fabrics pass this test by allowing virtually no water to pass therethrough. This result is comparable to the results obtained with higher cost so-called breathable waterproof fabrics currently commercially available in the market. In contrast, the original, untreated fabrics fail to pass this test because they demonstrate complete saturation. The fiber enveloped fabric samples retain excellent "hand" after the test.

The purpose and scope of this ASTM test is to evaluate resistance of a fiber enveloped fabric to water under simulated storm conditions. The test specifies that a test fabric is stormproof if less than one gram of water is absorbed by blotter paper with a shower head pressure of 3 feet exerted for 5 minutes. This test method is applicable to any textile fabric, whether or not it has a water repellent finish. It measures the resistance of a fabric to the penetration of water by impact, and thus can be used to predict the probably rain penetration resistance of a fabric. The results obtained with this method of test depend on the water repellency of the fibers and yarns in the fabric tested, and on the construction of the fabric.

This test involves a test specimen backed by a pre-weighed standard blotter. The assembly is sprayed with water for 5 minutes under controlled conditions. The blotter then is separated and weighted to determine the amount of water, if any, which has leaked through the specimen fabric during the test and has been absorbed by the blotter.

The methods and apparatus and materials employed in each test were a modified rain tester, blotter paper, water at 80° F. ±2° F., a laboratory balance, 8"×8" fabric specimens which had been pre-conditioned in an atmosphere of 65% (±2%) relative humidity and 70° F. (±2° F.) for four hours before testing, and tape.

The procedure followed for this test was as follows:
1. A 6"×6" paper blotter was weighted to the nearest 0.1 gm and placed behind the test specimen.
2. The test fabric with the paper blotter in registration therewith was taped on the specimen holder.
3. A tube in the rain tester was filled with water up to the 3 foot level. It was confirmed that water was flowing out of the overflow tube which maintains the 3 foot column of water.
4. The water spray distance from the tip of the nozzle to the specimen holder was measured and adjusted to 12 inches.
5. The specimen holder was left in place and the rain tester was turned on for five minutes.
6. After the test period, the paper blotter was removed and reweighed to the nearest 0.1 gm.

The results of the test selected fabric samples are shown in Table XV.

TABLE XV

Rain Test: Grams of Water Penetrating the Fabric

| FABRIC SAMPLE | ORIGINAL NOT WASHED | AFTER 5 MACHINE WASHES | AFTER 10 MACHINE WASHES |
|---|---|---|---|
| Hot Coral Tactel ® | 0 | 0 | 0 |
| Deva Blue Tactel ® | 0 | 0 | 0 |
| Prior Art Treated Fabrics | | | |
| Ultrex ® | 0 | — | 0.1 |
| Gore-Tex ® | 0 | 0 | — |

Original Fabrics—Water Repellant Chemicals Only, No Encapsulation
Hot Coral Tactel/Failed-saturated
Deva Blue Tactel/Failed-saturated

EXAMPLE 35

Viral Penetration Tests (ASTM ES22)

This example demonstrates the ability of the barrier webs of the present invention to prevent the penetration of blood-borne pathogens. The treated web samples are tested according to ASTM ES 22 (1995). The pathogenic viruses that are of particular concern are the hepatitus B virus (HBV), hepatitus C (HCV) and the human immunodeficiency virus and related viruses (HIV). In the assay used in this example, $\phi$x174 bacteriophage was used as the viral particle. An ASTM F903 Chemical Penetration Cell apparatus was used to measure the penetration of the $\phi$x174 bacteriophage through the barrier web.

Sterile test samples are placed in the Penetration Cell apparatus and challenged with the $\phi$x174 bacteriophage under various pressures and penetration of the viral particle was measured. At the conclusion of the test, the observed side of the article is rinsed with a sterile medium and then tested for the presence of $\phi$x174 bacteriophage.

HBV, HCV, and HIV range in size from 27 nm to approximately 110 nm. HCV is the smallest at 27 nm to 30 nm, HBV is 42–47 nm and HIV is 80 to 110 nm. All the viruses have a spherical or icosahedral structure. The $\phi$x174 bacteriophage has a diameter of between approximately 25 to 27 nm and is also icosahedral or nearly spherical. $\phi$x174 bacteriophage grows rapidly and can be grown to very high titers.

The surface tension of blood and body fluid is between approximately 42 to 60 dynes/cm. To provide for a similar wetting characteristic, the surface tension of the φx174 bacteriophage suspension is adjusted to approximately 40 to 44 dynes/cm using the surfactant Tween 80.

The web samples were treated to minimize viral penetration. Thicker internal layers or encapsulating films result in better viral barrier test results, but lower breatability. However, the treated webs showed breatability when worn all day by lab technicians. The results are shown in the following table:

TABLE XVI

| Sample | Challenge Concentration (Plaque forming units/ml | ES22 Result |
|---|---|---|
| 4040 + GE6108 polymer (53.3% wt. add on | $7 \times 10^8$ | Pass |
| 4040 + LIM 6060 polymer (87.6% wt. add on | $7 \times 10^8$ | Pass |
| $C^3$ fabric + polymer (22–35% wt add on | $1.5 \times 10^8$ | Pass |
| Lot #8253 (Nelson Labs | $1.36 \times 10^8$ | Pass |

"LIM" is the acronym for Liquid Injected Molding. All ES22 tests were performed by either MO Bio Laboratories, Solana Beach, Calif. or Nelson Laboratories, Inc., Salt Lake City, Utah. Sample materials were tested in triplicate using the ES22 barrier test as defined by ASTM. For a material to be considered a viral barrier, all three of the triplicate samples must pass. Tween 80

EXAMPLE 36

Bacteria Penetration Tests (Modified ASTM ES 22)

This example demonstrates the ability of webs treated in accordance with this invention to prevent the penetration of bacteria Bacteria is generally larger in size than viruses. A modified ASTM ES 22 test described in the previous example was used to test for bacteria penetration. The test was modified to use Escherichia coli (*E. coli*) ATCC number 25922 bacteria and a different agar solution as the nutrient broth. The media used consisted of the following:

| Nutrient Broth: | |
|---|---|
| Beef Extract | 3.0 g |
| Pancreatic digest of gelatin | 5.0 g |
| Potassium Chloride | 5.0 g |
| Calcium Chloride | 0.2 g |
| Distilled water to | 1000 ml |
| Adjust pH to 7.2–7.4 with 2.5 N Sodium Hydroxide and sterilize (40 μl/liter) | |

Nutrient Broth with 0.01% Tween® 80:

Same formula as above with 0.1 ml of Tween® 80 and 45 μl/liter of NaOH added.

Nutrient Broth with 0.1% Tween® 80:

Same formula as above with 1.0 ml of Tween® 80 and 45 μl/liter of NaOH added.

*E. coli* ATCC 25922 is MUG positive. The organism will fluoresce when grown on MacConkey Agar plate with MUG (Methylmbelliferyl β-D-Galactoside). The fluoresence provided a measure of selectivity for the assay. The fabric was challenged with *E. coli* ATCC strain 25922. Following the challenge, the unchallenged side was assayed for penetration of the *E. coli*. *E. coli* ranges in size from 0.5 to 3.0 microns. The results of the tests are shown below.

TABLE XVII

Bacterial Penetration Test Results

| Sample | Challenge Concentration | Modified ES22 Result |
|---|---|---|
| Burlington 40/40 fabric + 23.45% wt. add on GE 6108 polymer (sample H051995-N) | $6 \times 10^8$ | Pass |
| Burlington 40/40 fabric + 28.11% wt. add on GE 6108 polymer (sample H051995-I) | $6 \times 10^8$ | Pass |

MO BIO Laboratories, Solana Beach, Calif., performed all of the bacterial barrier tests.

EXAMPLE 37

Synthetic Blood Barrier Test

This example demonstrates the ability of webs treated in accordance with this invention to prevent the penetration of a blood-like fluid (synthetic blood). The treated web samples were tested according to a modified ASTM ES 21 Synthetic Blood Direct Pressure Draft Test Method (ASTM F23, 40, 04). Fabric samples of $C^3$ fabric were treated according to the practice of this invention to yield a fabric with 22–35% polymer weight add-on. The synthetic blood came from Jamar Health Products (Phil Johnson), Lot 220. The surface tension of the synthetic blood is 40 dynes/cm. According to the test procedure, synthetic blood is pressed against a fabric sample at increasing pressures at one spot until wicking of the fabric occurs. The final pressure is determined by over pressuring to create failure and then backing off at different sites until a pass occurs as per ASTM protocol F23, 40, 04 draft test method. This particular treated fabric (Sample #111193B) passed at 80 psi. No wicking occurred after one hour of elapsed time.

EXAMPLE 38

Cell Growth Promotion

This example shows the ability to bind growth factors to the polymer composition incorporated into webs of according to the present invention. The growth factor used in this example is ProNectin F, produced by Protein Polymer Technologies, Inc. (PPT), San Diego, Calif. ProNectin F is a substrate for receptor-specific cell attachment and is a protein polymer produced by bacterial fermentation. ProNectin F consists of 10% solids and 90% ProNectin F diluent. ProNectin F provides increased cell growth compared to traditional growth factors such as fibronectin.

Four 6"×6" samples were prepared:

1. A control sample containing no polymer and no growth factors, a control sample containing polymer but no growth factors
2. a sample containing polymer and Fibronectin
3. a sample containing polymer and ProNectin F Each of the samples containing a growth factor were prepared in the following manner:

1. Dow Corning 2303 silicone polymer plus an accelerator were mixed with the growth factor in a sufficient quantity to produce a final web having 17% weight add on polymer and 3% weight add on growth factor.
2. The web was a 3.2 oz. nylon web and was stretched.
3. The polymer mixture was applied to the surface of the web and a shearing knife was pulled across the web to shear thin the polymer mixture, place it into the web, and extract some of it out of the web. This procedure is commonly referred to as a "hand pull."

4. The treated webs were then cured in an oven for 20 seconds at 220° F. (a temperature and time small enough to ensure that the growth factors were not damaged).

5. The cured samples were then put aside for 2 hours.

The samples produced by the procedure above were then rinsed with serum-free growth medium to promote cell growth without other contaminants. The samples were then challenged with seed cells of HeLa which is a human cervical mammalian cell. The cells grown were then dislodged by standard trypsinization protocols and counted.

The end result was that webs treated in accordance with this invention, where PRONECTIN F was added, showed a 60–100% increase in cell growth over traditional fibronectin cell growth promoters and a much larger growth increase over samples containing no growth factors.

It should be understood, of course, that the foregoing relates only to preferred embodiments of the present invention and that numerous modifications or alterations may be made therein without departing from the spirit and the scope of the invention as set forth in the appended claims.

What is claimed is:

1. An incontinent garment comprising:

a shedding shield positioned next to the skin of the wearer which is substantially impermeable to liquids, wherein the shedding shield is a barrier web comprising a web that has been treated with a curable shear thinned thixotropic polymer composition;

one or more absorbent pads positioned under the shedding shield; and an outer layer which is breathable and substantially impermeable to liquids, wherein the shedding shield is shaped to direct liquids toward the absorbent pad.

2. The incontinent garment of claim 1, wherein the absorbent pad is larger than the shedding shield.

3. The incontinent garment of claim 1, wherein the absorbent pad is smaller than the shedding shield.

4. The incontinent garment of claim 1, wherein the absorbent pad is disposable.

5. The incontinent garment of claim 4, wherein the shedding shield has one or more openings formed therein allowing some liquid to pass through to the absorbent pad.

* * * * *